US006855805B2

(12) United States Patent
Olivera et al.

(10) Patent No.: US 6,855,805 B2
(45) Date of Patent: Feb. 15, 2005

(54) α-CONOTOXIN PEPTIDES

(75) Inventors: Baldomero M. Olivera, Salt Lake City, UT (US); Richard T. Layer, Sandy, UT (US); J. Michael McIntosh, Salt Lake City, UT (US); Jacob Scott Nielsen, Brigham City, UT (US); Robert M. Jones, Salt Lake City, UT (US)

(73) Assignees: University of Utah Research Foundation, Salt Lake City, UT (US); Cognetix, Inc., Salt Lake City, UT (US)

( * ) Notice: Subject to any disclaimer, the term of this patent is extended or adjusted under 35 U.S.C. 154(b) by 92 days.

(21) Appl. No.: 09/908,741

(22) Filed: Jul. 20, 2001

(65) Prior Publication Data

US 2003/0050435 A1 Mar. 13, 2003

Related U.S. Application Data

(63) Continuation-in-part of application No. 09/488,799, filed on Jan. 21, 2001, now Pat. No. 6,268,473.
(60) Provisional application No. 60/116,881, filed on Jan. 22, 1999, provisional application No. 60/116,882, filed on Jan. 22, 1999, provisional application No. 60/219,407, filed on Jul. 20, 2000, and provisional application No. 60/221,557, filed on Jul. 28, 2000.

(51) Int. Cl.⁷ .................. A61K 38/00; A61K 38/04
(52) U.S. Cl. .................................. 530/325; 530/327
(58) Field of Search ................. 530/325, 327, 530/324, 326; 514/2, 12, 13; 536/23.5

(56) References Cited

U.S. PATENT DOCUMENTS

| 4,447,356 A | 5/1984 | Olivera et al. |
| 5,231,011 A | 7/1993 | Hillyard et al. |
| 5,432,155 A | 7/1995 | Olivera et al. |
| 5,514,774 A | 5/1996 | Olivera et al. |
| 5,969,096 A | 10/1999 | Shon et al. |

FOREIGN PATENT DOCUMENTS

| EP | 0 593 450 | 4/1994 | | |
| EP | 0 625 162 | 11/1994 | | |
| JP | 60226899 A | * 11/1985 | ............ | C07K/7/08 |
| JP | 61005095 A | * 1/1986 | ............ | C07K/7/08 |
| WO | WO 91/07980 | 6/1991 | | |
| WO | WO 93/10145 | 5/1993 | | |
| WO | WO 93/13128 | 7/1993 | | |
| WO | WO 99/54350 | 10/1999 | | |
| WO | WO 00/15654 | 3/2000 | | |

OTHER PUBLICATIONS

Dictionary of Biochemistry and Molecular Biology 97 (John Wiley & Sons, 2 ed. 1989).*
Bai–Song, L. et al. (1999). *Peptides* 20:1139–1144.
Favreau, P. et al. (1999). *Biochem* 38:6317–6326.
McIntosh, J.M. et al. (1999). *Ann Rev Biochem* 68:59–88.

Protein Sequence Database, PIR Entry NTKNAG (2000).
Protein Sequence Database, PIR Entry NTKN2G (2000).
Protein Sequence Database, PIR Entry NTKN1M (2000).
Protein Sequence Database, PIR Entry NTKNAS (2000).
Protein Sequence Database, PIR Entry A58589 (2000).
Protein Sequence Database, PIR Entry A53709 (2000).
Protein Sequence Database, PIR Entry A28953 (2000).
Protein Sequence Database, PIR Entry A44379 (2000).
Protein Sequence Database, PIR Entry A58963 (2000).
Protein Sequence Database, PIR Entry A59046 (2000).
Richard M. Hann, et al., "The α–Conotoxins GI and MI Distinguish between the Nicotinic Acetylcholine Receptor Agonist Sites while SI Does Not", Biochemistry vol. 33, No. 47, 1994, pp. 14058–14063.
Duncan R. Groebe, et al., "Determinants Involved in the Affinity of α–Conotoxins GI and SI for the Muscle Subtype of Nicotinic Acetylcholine Receptors", Biochemistry, vol. 36, No. 21, 1997, pp. 6469–6474.
Duncan R. Groebe, et al., "α–Conotoxins Selectively Inhibit One of the Two Acetylcholine Binding Sites of Nicotinic Receptors", Molecular Pharmacology, vol. 48, 1995, pp. 105–111.
Ronald G. Almquist, et al., "Paralytic activity of des–Glu¹)conotoxin GI analogs in the mouse diaphragm", Int. J. Peptide Protein Res., vol. 34, 1989, pp. 455–462.
Richard M. Hann, et al., "The 9–Arginine Residue of α–Conotoxin GI Is Responsible for Its Selective High Affinity for the αγ Agonist Site on the Electric Organ Acetylcholine Receptor", Biochemistry, vol. 36, No. 29, 1997, pp. 9051–9056.
Richard B. Jacobsen, et al., "Critical Residues Influence the Affinity and Selectivity of α–Conotoxin MI for Nicotinic Acetylcholine Receptors", Biochemistry, vol. 38, No. 40, 1999, pp. 13310–13315.
Nina Bren, et al., "Hydrophobic Pairwise Interactions Stabilize α–Conotoxin MI In the Muscle Acetylcholine Receptor Binding Site", The Journal of Biological Chemistry, vol. 275, No. 17, Apr. 28, 2000, pp. 12692–12700.
Letter to the Editor, "Development of New Neuromuscular Blocking Drugs", Asia Pacific Journal of Pharmacology, vol. 12, 1997, pp. 57–64.
David R. Bevan, et al. "Neuromuscular Blocking Drugs: Onset and Intubation", Journal of Clinical Anesthesia, vol. 9, Sep. 1997, pp. 383–396.

(List continued on next page.)

*Primary Examiner*—Karen Cochrane Carlson
(74) *Attorney, Agent, or Firm*—Rothwell, Figg, Ernst & Manbeck, p.c.

(57) ABSTRACT

The invention relates to relatively short peptides (termed α-conotoxins herein), about 10-25 residues in length, which are naturally available in minute amounts in the venom of the cone snails or analogous to the naturally available peptides, and which preferably include two disulfide bonds. The α-conotoxins, as described herein, are useful for as neuromuscular blocking agents, such as muscle relaxants.

4 Claims, 5 Drawing Sheets

OTHER PUBLICATIONS

M. McIntosh, et al., "Isolation and Structure of a Peptide Toxin from the Marin Snal *Conus magus*", Archives of Biochemistry and Biophysics, vol. 218, No. 1, Oct. 1, 1982, pp. 329–334.
Craig S. Walker, et al., "The T–Superfamily of Conotoxins", The Journal of Biological Chemistry, vol. 274, No. 43, Oct. 22, 1999, pp. 30664–30671.
Baldomero M. Olivera, et al., "Generating molecular diversity in Conus venoms", Abstract.
Alan C. Rigby, et al. "A conotoxin from *Conus textile* with unusual posttranslational modifications reduces presynaptic $Ca^{2+}$ influx", Proc. Natl. Acad. Sci. USA, vol. 96, May 1999, pp. 5758–5763.
Internal Scientific Report, Metabolic Stability of CGX–1079 (α–Conopeptide GI), May 4, 2000.
Alan C. Rigby, et al., "Gamma–carboxyglutamic acid–containing conotoxins in the venom from *Conus textile*", Abstract.
Problem Solving Report Question No.—1026746.044, Neurex—Conot xin, Calcium Channel Patents, May 3, 2000, Tech. Spec.—John Leavitt.
Protein Sequence Database, PIR Entry B59045 (2000).
Protein Sequence Database, PIR Entry C59045 (2000).
Protein Sequence Database, PIR Entry A59042 (2000).
Protein Sequence Database, PIR Entry A59045 (2000).
Protein Sequence Database, PIR Entry A54877 (2000).
Protein Sequence Database, PIR Entry B54877 (2000).
Olivera et al. (1985). *Science* 230:1338–1343.
Olivera et al. (1990). *Science* 249:257–263.
Myers et al. (1993). *Chem. Rev.* 93:1923–1936.
Blount et al. (1992). *Toxicon.* 30(8):835–842.
Gray et al. (1981). *J. Biol. Chem.* 256(10):4734–4740.
Hashimoto et al. (1985). *Eur. J. Pharmacol.* 118:351–354.
Marshall et al. (1990). *Toxicon.* 28(2):231–234.
McManus et al. (1985). *J. Neurosci.* 5(1):110–116.
McManus et al. (1981). *Neurosci. Letts.* 24:57–82.
Smythies (1981). *Medical Hypotheses* 7:1457–1460.
Bevan (1997). *J. Clin. Anesthesia* 9:365, 375, 385, 395.
Bowman (1997). *Asia Pacific J. Pharmacol.* 12:57–64.
Bren et al. (2000). *J. Biol. Chem.*275(17):12692–12700.
Jacobsen et al. (1999). *Biochem.* 38:13310–13315.
Hann et al. (1994). *Biochem.* 33:14058–14063.
Groebe et al. (1997). *Biochem.* 36:6469–6474.
Groebe et al. (1995). *Mol. Pharmacol.* 48:105–111.
Hann et al. (1997). *Biochem.* 36:9051–9056.
Almquist et al. (1989) *Int. J. Peptide Protein Res.* 34:455–462.
McIntosh et al. (1982). *Arch. Biochem. & Biophys.* 218(1):329–334.
"Conus Peptides Targeted to Specific Nicotinic Acetylcholine Receptor Subtypes," J. Michael McIntosh et al., Annu. Rev. Biochem. 1999 68:59–88.
"Conus peptides—Combinatorial chemistry at a cone snail's pace," Robert M. Jones et al., Current Opinion in Drug Discovery & Development 2000 3(2):141–154.

* cited by examiner

α-CONOTOXIN PEPTIDES

CROSS-REFERENCE TO RELATED APPLICATIONS

The present application is a continuation-in-part of patent application Ser. No. 09/488,799 filed on 21 Jan. 2001 now U.S. Pat. No. 6,268,473 and claims benefit thereto. The present application also claims benefit under 35 USC §119(e) to U.S. provisional patent applications Ser. No. 60/116,881 filed on 22 Jan. 1999, Ser. No. U.S. 60/116,882 filed on 22 Jan. 1999, 60/219,407 filed on 20 Jul. 2000 and Ser. No. 60/221,557 filed on 28 Jul. 2000. Each of these applications is incorporated herein by reference.

This invention was made with Government support under Grant No. PO1 GM48677 awarded by the National Institute of General Medical Sciences, National Institutes of Health, Bethesda, Md. and under SBIR grant No. 1 R43 GM62064-01. The United States Government has certain rights in the invention.

BACKGROUND OF THE INVENTION

The invention relates to relatively short peptides (termed α-conotoxins herein), about 10–25 residues in length, which are naturally available in minute amounts in the venom of the cone snails or analogous to the naturally available peptides, and which preferably include two disulfide bonds. The α-conotoxins, as described herein, are useful for as neuromuscular blocking agents, such as muscle relaxants.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these peptides are a large genus of venomous gastropods comprising approximately 500 species. All cone snail species are predators that inject venom to capture prey, and the spectrum of animals that the genus as a whole can envenomate is broad. A wide variety of hunting strategies are used, however, every Conus species uses fundamentally the same basic pattern of envenomation.

Several peptides isolated from Conus venoms have been characterized. These include the α-, μ-, ω- and co-conotoxins which target nicotinic acetylcholine receptors, muscle sodium channels, and neuronal calcium channels, respectively (Olivera et al., 1985). Conopressins, which are vasopressin analogs, have also been identified (Cruz et al. 1987). In addition, peptides named conantokins have been isolated from Conus geographus and Conus tulipa (Mena et al., 1990; Haack et al., 1990).

The α-conotoxins are small peptides highly specific for neuromuscular junction nicotinic acetylcholine receptors (Gray et al., 1981; Marshall and Harvey, 1990; Blount et al., 1992). The α-conotoxin peptides MI and GI are selective for the α/δ subunit interface of the neuromuscular junction nicotinic receptor over the α/γ subunit interface by >10,000 fold, while the α-conotoxin peptides EI and EIA bind both sites with equal affinity. However, none of these peptides show siginificant affinity for neuronal nicotinic receptors.

Various compounds having muscle relaxant properties are set forth in U.S. Pat. Nos. 4,190,674; 4,508,715; 4,761,418; 4,701,460; 4,179,507; 4,923,898; 5,015,741; and 5,260,337; as well as in Goodman and Gilman's *The Pharmacological Basis of Therapeutics*, Section II, especially Chapter 11, 7th Ed. (1985) and *Physicians Desk Reference*, 48 Ed., pp. 689, 758, 1362 and 1648 (1994).

Compounds having musculoskeletal relaxing properties include (1) agents acting in the central nervous system which are used to relieve pain associated with muscle contraction (e.g., 5-chlorobenzoxazolinone available as Parafon Forte DSC from McNeil Pharmaceutical), and (2) agents acting in the peripheral nervous system used primarily to induce muscle relaxation and hence reduce muscle contraction during anesthesia. The second group of muscle relaxants is subdivided into two groups: (i) non-depolarizing agents which inhibit the activation of muscle receptors (e.g., metocurarine iodide, d-tubocurarine, tubocurarine chloride, pancuronium, gallamine, diallytoiferine, toxiferine, atracurium besylate which is available as Tracrium from Burroughs-Wellcome Co., and vecuronium bromide which is available as Norcuron from Organon Inc.) and (ii) depolarizing agents which transiently activate muscle receptors and result in their blockade (e.g., decamethonium iodide, and succinylcholine chloride which is available as Anectine from Burroughs-Wellcome Co.). The effects of the depolarizing agents are manifested as fasciculations and flaccid paralysis which are observed to occur rapidly after their injection.

The effects of depolarizing agents (DA) and non-depolarizing agents (NDA) are separated based on their duration of action from ultrashort acting (e.g. for a depolarizing agent such as succinylcholine chloride) to intermediate (e.g. for a non-depolarizing agent such as atracurium besylate). Certain types of muscle relaxants are useful as neuromuscular blocking agents in clinical applications, and have found use as adjuvants to surgical anesthesia, in orthopedic surgical procedures and in facilitating endotracheal intubation procedures. Some of these compounds (e.g., succinylcholine chloride) are routinely used to provide muscle relaxation during Cesarean section procedures.

It is desirable for neuromuscular blocking agents to be locally acting and highly selective for binding to muscle nicotinic acetylcholine receptor sites. As such, when a patient is treated with anesthesia, the muscle relaxant is applied (e.g., intravenously or by injection), in order to cause the muscle to relax and hence minimize muscle contraction.

In anesthesia, neuromuscular blocking agents are used to provide skeletal muscular relaxation during surgery and during intubation of the trachea. All of the conventional nondepolarizing agents when used for producing skeletal muscle relaxation in surgery have a long duration of action e.g., 60 to 180 minutes in man. The depolarizing agents on the other hand provide muscle relaxation at dosages normally used for surgery which is less than the duration of action of nondepolarizing agents. For example, succinylcholine provides a short duration of action of about 5 to 15 minutes whereas decamethonium provides about 20 to 40 minutes duration of muscle relaxation. The long duration of action of nondepolarizing agents is unacceptable in many surgical procedures which take less than one hour because the patient is not generally filly recovered from their effects e.g., the patient may be unable to breathe adequately on his or her own.

Each nondepolarizing agent has inherent side-effects. For example, gallamine and pancuronium may cause tachycardia, d-tubocurarine and diallyltoxiferine may cause hypotension, and succinylcholine may cause fasciculations, myalgia, potassium release, cardiovascular effects, immunological reactions and malignant hyperthermia. While such drugs can be pharmacologically antagonized with anticholinesterase agents, this obviously necessitates the administration of a second drug which itself may have its own side effects e.g., bradycardia, gut spasm and bronchorrhea. Thus to overcome the aforementioned side-effects of the anticholinesterase agents, a third drug, an anticholinergic drug e.g., atropine must also be given.

With the use of depolarizing agents, there is no need to reverse the effects of the depolarizing agents, in certain patients the effects are much prolonged because of abnormal metabolism of the agent by the patient. The polarizing agents due to the mode of action which initially causes skeletal muscle contraction and stimulation of smooth muscles are also known to cause the following side-effects in certain instances; increased intraocular, and intragastric tension, cardiac arrhythmias, potassium release, and muscle pain. These side-effects caused by the depolarizing agents are not caused by the nondepolarizing agents. It is therefore clearly evident that a new neuromuscular blocking agent having the relatively few side-effects and the reversibility of the nondepolarizing agents yet being of considerably shorter i.e., intermediate, duration of action is needed.

It is desired to provide a compound useful as a muscle relaxant. In particular, it is desired to provide an antagonist which has activity at relatively low concentrations as a neuromuscular blocking agent. It is also desired to achieve muscle relaxation at concentrations of agonist that are devoid of any ganglionic effects (e.g., so as to not exhibit side effects such as those associated with interaction with cardiovascular sites). As such, it is desired to provide muscle relaxant compositions and methods for providing muscle relaxation. Finally, it is desired to identify additional α-conotoxin peptides for use as neuromuscular blocking agents.

SUMMARY OF THE INVENTION

The invention relates to relatively short peptides (termed α-conotoxins herein), about 10–25 residues in length, which are naturally available in minute amounts in the venom of the cone snails or analogous to the naturally available peptides, and which preferably include two disulfide bonds. The α-conotoxins, as described herein, are useful for as neuromuscular blocking agents, such as muscle relaxants, for treating benign essential blepharospasm and other forms of focal dystonia and for anti-wrinkle use.

More specifically, the present invention is directed to the neuromuscular blocking use of α-conotoxin peptides of two classes, namely, (a) α3/5 or α3/6 and (b) α4/7, as described herein. The first class of α-conotoxin peptides has the general formula I:

$Xaa_1$-$Xaa_2$-$Xaa_3$-$Xaa_4$-Cys-Cys-$Xaa_5$-$Xaa_6$-$Xaa_7$-Cys-$Xaa_8$-$Xaa_9$-$Xaa_{10}$-$Xaa_{11}$-$Xaa_{12}$-$Xaa_{13}$-Cys-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$ (SEQ ID NO: 1), wherein $Xaa_1$ is des-$Xaa_1$ or Gly; $Xaa_2$ is des-$Xaa_2$, Asn, Arg, Asp, Ser, Thr, Lys, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_3$ is des-$Xaa_3$, Gly, Glu or γ-carboxy-Glu (Gla); $Xaa_4$, is des-$Xaa_4$, Glu, Gla, Gln, pyro-Glu, Arg, Ile Tyr, mono-halo-Tyr, di-halo-Tyr, O-sulpho-Tyr, O-phospho-Tyr, nitro-Tyr, Cys, His, halo-His, any unnatural hydroxy containing amino acid (such as 4-hydroxymethyl-Phe, 4-hydroxyphenyl-Gly, 2,6-dimethyl-Tyr and 5-amino-Tyr), Lys, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_5$ is His, Asn or halo-His; $Xaa_6$ is Pro or hyroxy-Pro; $Xaa_7$ is Ala, Gly, Ser or Thr; $Xaa_8$ is Gly or Ala; $Xaa_9$ is Arg, Lys, Pro, hydroxy-Pro, Gly, Gln, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{10}$ is His, halo-His, Asn, Lys, Tyr, mono-halo-Tyr, di-halo-Tyr, O-sulpho-Tyr, O-phospho-Tyr, nitro-Tyr, N-methy-Lys, N,N-dimethyl-Lys, N,N,N-trimethyl-Lys, Arg, homoarginine, ornithine or any unnatural basic amino acid (such as N-1-(2-pyrazolinyl)-Arg); $Xaa_{11}$ is Tyr, Phe, mono-halo-Tyr, di-halo-Tyr, O-sulpho-Tyr, O-phospho-Tyr, nitro-Tyr, any unnatural hydroxy containing amino acid (such as 4-hydroxymethyl-Phe, 4-hydroxyphenyl-Gly, 2,6-dimethyl-Tyr and 5-amino-Tyr), Trp (D or L), halo-Trp, neo-Trp, or any unnatural aromatic amino acid (such as nitro-Phe, 4-substituted-Phe wherein the substituent is $C_1$–$C_3$ alkyl, carboxyl, hyrdroxymethyl, sulphomethyl, halo, phenyl, —CHO, —CN, —$SO_3$H and —NHAc); $Xaa_{12}$ is Ile, Ser, Thr, Asp, Gly, Asn, Glu, Gla or Val; $Xaa_{13}$ is des-$Xaa_{13}$, Lys, Arg, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{14}$ is des-$Xaa_{14}$, Gly, Lys, Arg, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{15}$ is des-$Xaa_{15}$, Gly, Thr, Ser, His, halo-His, Lys, Arg, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{16}$ is des-$Xaa_{16}$, Ser or Thr; $Xaa_{17}$ is des-$Xaa_{17}$ or Cys; $Xaa_{18}$ is des-$Xaa_{18}$, Ser or Thr; $Xaa_{19}$ is des-$Xaa_{19}$, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_{20}$ is des-$Xaa_{20}$, Thr, Ser, Pro or hydroxy-Pro; $Xaa_{21}$ is des-$Xaa_{21}$, Leu, Ser or Thr; $Xaa_{21}$ is des-$Xaa_{22}$, Glu or Gla); $Xaa_{23}$ is des-$Xaa_{23}$, Pro or hydroxy-Pro; $Xaa_{24}$ is des-$Xaa_{24}$, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg); and $Xaa_{25}$ is des-$Xaa_{25}$, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg). The C-terminus may contain a free carboxyl group or an amide group, preferably an amide group. The halo is chlorine, bromine or iodine, preferably iodine for Tyr and bromine for Trp. The Cys residues may be in D or L configuration and may optionally be substituted with homocysteine.

Useful peptides include GI (Gray et al., 1981), GIA (Gray et al., 1981), GII (Gray et al., 1981), MI (McIntosh et al., 1982), SI (Zafaralla et al., 1988), SIA (Myers et al., 1991), SIB (same as SI, except further contains Glu at N-terminus), SII (Olivera et al., 1996), SIIA (Olivera et al., 1996), R1 (same as G1, except Tyr for Lys), R1.3 (below), R1.4 (below), Sm1.1 (below), S11 (below), S2 (below); GIB (same as R1); MnII (below); A1.2 (below); A1.3 (below);

A1.7 (below); A1.8 (below); Ay1.1 (below); Ay1.1a (below); M1.1 (below); M1.3 (below); M1.4 (below); M1.5 (below); O1.3 (below); S1.3 (below); Sa (below). Additional useful peptides are analogs of MI and GI as described below.

The second class of α-conotoxin peptides has the general formula II:

$Xaa_1$-$Xaa_2$-$Xaa_3$-Cys-Cys-$Xaa_4$-$Xaa_5$-$Xaa_6$-$Xaa_7$-Cys-$Xaa_8$-$Xaa_9$-$Xaa_{10}$-$Xaa_{11}$-$Xaa_6$-$Xaa_{12}$-Ile Cys-$Xaa_{13}$-$Xaa_{14}$-$Xaa_{15}$ (SEQ ID NO:2), wherein, $Xaa_1$ is des-$Xaa_1$, Arg, Ser, Thr, Lys, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_2$ is des-$Xaa_2$, Asp, Gly, Leu, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_3$ is des-$Xaa_3$, Pro, hydroxy-Pro, Ala, Gly or Leu; $Xaa_4$ is Tyr, Ser, Thr, mono-halo-Tyr, di-halo-Tyr, O-sulpho-Tyr, O-phospho-Tyr, nitro-Tyr or any unnatural hydroxy containing amino acid (such as 4-hydroxymethyl-Phe, 4-hydroxyphenyl-Gly, 2,6-dimethyl-Tyr and 5-amino-Tyr); $Xaa_5$ is His, Asn, Ile, Tyr, halo-His, mono-halo-Tyr, di-halo-Tyr, O-sulpho-Tyr, O-phospho-Tyr or nitro-Tyr; $Xaa_6$ is Pro or hydroxy-Pro; $Xaa_7$ is Thr, Ala, Val, Ser, Pro or hydroxy-Pro; $Xaa_8$ is Asn, Thr, Ser, Lys, Arg, ornithine, homoargine, N-methy-Lys, N,N-dimethyl-Lys, N,N,N-trimethyl-Lys or any unnatural basic amino acid (such as N-1-(2-pyrazolinyl)-Arg); $Xaa_9$ is Met, Val, Ala, Leu or Ile; $Xaa_{10}$ is Ser, Thr, Asn, His or halo-His; $Xaa_{11}$ is Asn, Tyr, mono-halo-Tyr, di-halo-Tyr, O-sulpho-Tyr, O-phospho-Tyr, nitro-Tyr, or any unnatural hydroxy containing amino acid (such as 4-hydroxymethyl-Phe, 4-hydroxyphenyl-Gly, 2,6-dimethyl-Tyr and 5-amino-Tyr); $Xaa_{12}$ is Glu, γ-carboxy-Glu (Gla), Gln or Asp; $Xaa_{13}$ is des-$Xaa_{13}$ or Gly; $Xaa_{14}$ is des-$Xaa_{14}$ or Gly; and $Xaa_{15}$ is des-$Xaa_{15}$, Arg, Lys, ornithine, homoargine, N-methy-Lys, N,N-dimethyl-Lys, N,N,N-trimethyl-Lys or any unnatural basic amino acid (such as N-1-(2-pyrazolinyl)-Arg). The C-terminus may contain a free carboxyl group or an amide group, preferably an amide group. The halo is preferably chlorine or iodine, more preferably iodine. The Cys residues may be in D or L configuration and may optionally be substituted with homocysteine.

Useful peptides include E1 (U007; Olivera et al., 1996), EIA (U008; Olivera et al., 1996), P1.2 (below), P1.3 (below), Sl1.4 (below), Sl1.4A (below); Sl1.8 (below) and Ta (below).

The present invention is also directed to novel specific α-conotoxin peptides of class I having the formulas:

$Xaa_1$-Cys-Cys-Asn-$Xaa_2$-Ala-Cys-Gly-Arg-His-$Xaa_3$-Ser-Cys-$Xaa_4$-Gly (SEQ ID NO:3);

Asn-Gly-Arg-Cys-Cys-His-$Xaa_2$-Ala-Cys-Gly-$Xaa_4$-His-Phe-Ser-Cys (SEQ ID NO:4);

Gly-Arg-Gly-Arg-Cys-Cys-His-$Xaa_2$-Ala-Cys-Gly-$Xaa_2$-Asn-$Xaa_3$-Ser-Cys (SEQ ID NO:5);

Cys-Cys-His-$Xaa_2$-Ala-Cys-Gly-Arg-$Xaa_4$-$Xaa_3$-Asn-Cys (SEQ ID NO:6);

Cys-Cys-Cys-Asn-$Xaa_2$-Ala-Cys-Gly-$Xaa_2$-Asn-$Xaa_3$-Gly-Cys-Gly-Thr-Ser-Cys-Ser-Arg-$Xaa_2$-Ser-$Xaa_1$-$Xaa_2$-Arg-Arg (SEQ ID NO:7);

Asn-Gly-His-Cys-Cys-His-$Xaa_2$-Ala-Cys-Gly-Gly-$Xaa_4$-$Xaa_3$-Val-$Xaa_4$-Cys (SEQ ID NO:8);

Asn-Gly-Arg-Cys-Cys-His-$Xaa_2$-Ala-Cys-Gly-Gly-$Xaa_4$-$Xaa_3$-Val-$Xaa_4$-Cys (SEQ ID NO:9);

Asn-Gly-Arg-Cys-Cys-His-$Xaa_2$-Ala-Cys-Gly-$Xaa_4$-His-Phe-Ile-Cys (SEQ ID NO:10);

Asn-Gly-Arg-Cys-Cys-His-$Xaa_2$-Ala-Cys-Gly-$Xaa_4$-His-Phe-Ser-Cys (SEQ ID NO:11);

Asn-Gly-Arg-Cys-Cys-His-$Xaa_2$-Ser-Cys-Gly-Arg-$Xaa_4$-$Xaa_3$-Asn-Cys (SEQ ID NO:12);

Asn-Gly-Arg-Cys-Cys-His-$Xaa_2$-Ala-Cys-Ala-Arg-$Xaa_4$-$Xaa_3$-Asn-Cys (SEQ ID NO:13);

Asn-$Xaa_1$-Arg-Cys-Cys-His-$Xaa_2$-Ala-Cys-Ala-Arg-$Xaa_4$-$Xaa_3$-Asn-Cys (SEQ ID NO:14);

Asp-Gly-Arg-Cys-Cys-His-$Xaa_2$-Ala-Cys-Gly-Gln-Asn-$Xaa_3$-Ser-Cys (SEQ ID NO:15);

Asp-Gly-Arg-Cys-Cys-His-$Xaa_2$-Ala-Cys-Ala-$Xaa_4$-His-Phe-Asn-Cys (SEQ ID NO:16);

Asn-Gly-Arg-Cys-Cys-His-$Xaa_2$-Ala-Cys-Ala-$Xaa_4$-Asn-$Xaa_3$-Ser-Cys (SEQ ID NO:17);

Asn-Gly-Arg-Cys-Cys-His-$Xaa_2$-Ala-Cys-Ala-Arg-$Xaa_4$-$Xaa_3$-Ser-Cys (SEQ ID NO:18);

$Xaa_5$-Cys-Cys-Asn-$Xaa_2$-Ala-Cys-Gly-$Xaa_2$-$Xaa_4$-$Xaa_3$-Ser-Cys (SEQ ID NO:19);

$Xaa_5$-Cys-Cys-His-$Xaa_2$-Ala-Cys-Gly-$Xaa_4$-$Xaa_4$-$Xaa_3$-Asn-Cys (SEQ ID NO:20); and Ser-Gly-Arg-Cys-Cys-His-$Xaa_2$-Ala-Cys-Gly-Arg-$Xaa_4$-$Xaa_3$-Asn-Cys (SEQ ID NO:21), wherein $Xaa_1$ is Glu or γ-carboxy-glutamate (Gla); $Xaa_2$ is Pro or hydroxy-Pro; $Xaa_3$ is Tyr, mono-halo-Tyr, di-halo-Tyr, O-sulpho-Tyr, O-phospho-Tyr or nitro-Tyr; $Xaa_4$ is Lys, N-methyl-Lys, N,N-dimethyl-Lys or N,N,N-trimethyl-Lys; $Xaa_5$ is Gln or pyro-Glu; and the C-terminus contains a carboxyl or amide group, preferably an amide group. The halo is preferably chlorine or iodine, more preferably iodine. In addition, the His residues may be substituted with halo-His; the Arg residues may be substituted by Lys, ornithine, homoargine, N-methy-Lys, N,N-dimethyl-Lys, N,N,N-trimethyl-Lys or any unnatural basic amino acid (such as N-1-(2-pyrazolinyl)-Arg); the Lys residues may be substituted by Arg, ornithine, homoargine, N-methy-Lys, N,N-dimethyl-Lys, N,N,N-trimethyl-Lys or any unnatural basic amino acid (such as N-1-(2-pyrazolinyl)-Arg); the Tyr residues may be substituted with $^{125}$I-Tyr or any unnatural hydroxy containing amino acid (such as 4-hydroxymethyl-Phe, 4-hydroxyphenyl-Gly, 2,6-dimethyl-Tyr and 5-amino-Tyr); the Ser residues may be substituted with Thr; the Thr residues may be substituted with Ser; and the Phe residues may be substituted with any unnatural aromatic amino acid (such as nitro-Phe, 4-substituted-Phe wherein the substituent is $C_1$–$C_3$ alkyl, carboxyl, hyrdroxymethyl, sulphomethyl, halo, phenyl, —CHO, —CN, —$SO_3$H and —NHAc).

More specifically, the present invention is directed to the following α-conotoxin peptides of class I:

R1.3: SEQ ID NO:3, wherein $Xaa_1$ is Glu, $Xaa_2$ is Pro, $Xaa_3$ is Tyr and $Xaa_4$ is Lys;

R1.4: SEQ ID NO:4, wherein $Xaa_2$ is Pro and $Xaa_4$ is Lys;

Sm1.1: SEQ ID NO:5, wherein $Xaa_2$ is Pro and $Xaa_3$ is Tyr;

S11: SEQ ID NO:6, wherein $Xaa_2$ is Pro, $Xaa_3$ is Tyr and $Xaa_4$ is Lys;

S2: SEQ ID NO:7, wherein $Xaa_1$ is Glu, $Xaa_2$ is Pro and $Xaa_3$ is Tyr;

MnII: SEQ ID NO:8, wherein $Xaa_2$ is Pro, $Xaa_3$ is Tyr and $Xaa_4$ is Lys;

A1.2: SEQ ID NO:9, wherein $Xaa_2$ is Pro, $Xaa_3$ is Tyr and $Xaa_4$ is Lys;

A1.3: SEQ ID NO:10, wherein $Xaa_2$ is Pro and $Xaa_4$ is Lys;

A1.7: SEQ ID NO:11, wherein $Xaa_2$ is Pro and $Xaa_4$ is Lys;

A1.8: SEQ ID NO:12, wherein $Xaa_2$ is Pro and $Xaa_4$ is Lys;

Ay1.1: SEQ ID NO:13, wherein $Xaa_2$ is Pro, $Xaa_3$ is Tyr and $Xaa_4$ is Lys;

Ay1.1a: SEQ ID NO:14, wherein Xaa$_1$ is Glu, Xaa$_2$ is Pro, Xaa$_3$ is Tyr and Xaa$_4$ is Lys;

M1.1: SEQ ID NO:15, wherein Xaa$_2$ is Pro and Xaa$_3$ is Tyr;

M1.3: SEQ ID NO:16, wherein Xaa$_2$ is Pro and Xaa$_4$ is Lys;

M1.4: SEQ ID NO:17, wherein Xaa$_2$ is Pro, Xaa$_3$ is Tyr and Xaa$_4$ is Lys;

M1.5: SEQ ID NO:18, wherein Xaa$_2$ is Pro, Xaa$_3$ is Tyr and Xaa$_4$ is Lys;

O1.3: SEQ ID NO:19, wherein Xaa$_2$ is Pro, Xaa$_3$ is Tyr, Xaa$_4$ is Lys and Xaa$_5$ is Gln;

S1.3: SEQ ID NO:20, wherein Xaa$_2$ is Pro, Xaa$_3$ is Tyr, Xaa$_4$ is Lys and Xaa$_5$ is Gln; and Sa: SEQ ID NO:21, wherein Xaa$_2$ is Pro, Xaa$_3$ is Tyr and Xaa$_4$ is Lys.

The C-terminus is preferably amidated in each of these specific peptides.

The present invention is further directed to MI and GI analogs having the formulas:

MI[K10Q]: Gly-Arg-Cys-Cys-His-Pro-Ala-Cys-Gly-Gln-Asn-Tyr-Ser-Cys (SEQ ID NO:102);

MI[K10E]: Gly-Arg-Cys-Cys-His-Pro-Ala-Cys-Gly-Glu-Asn-Tyr-Ser-Cys (SEQ ID NO:103);

MI[K10Q, N11Q]: Gly-Arg-Cys-Cys-His-Pro-Ala-Cys-Gly-Gln-Gln-Tyr-Ser-Cys (SEQ ID NO:104);

MI[H5N, K10Q]: Gly-Arg-Cys-Cys-Asn-Pro-Ala-Cys-Gly-Gln-Asn-Tyr-Ser-Cys (SEQ ID NO:105);

MI[K10N]: Gly-Arg-Cys-Cys-His-Pro-Ala-Cys-Gly-Asn-Asn-Tyr-Ser-Cys (SEQ ID NO:106);

desG1-MI[K10Q, N11Q]: Arg-Cys-Cys-His-Pro-Ala-Cys-Gly-Gln-Gln-Tyr-Ser-Cys (SEQ ID NO:107);

MI[K10Q, S13D]: Gly-Arg-Cys-Cys-His-Pro-Ala-Cys-Gly-Gln-Asn-Tyr-Asp-Cys (SEQ ID NO:108);

MI[K10homoSer]: Gly-Arg-Cys-Cys-His-Pro-Ala-Cys-Gly-Xaa-Asn-Tyr-Ser-Cys (SEQ ID NO:109), where Xaa is homoserine;

desG1-MI[R2E, K10Q]: Glu-Cys-Cys-His-Pro-Ala-Cys-Gly-Gln-Asn-Tyr-Ser-Cys (SEQ ID NO:110);

desG1/R2-MI[K10Q]: Cys-Cys-His-Pro-Ala-Cys-Gly-Gln-Asn-Tyr-Ser-Cys (SEQ ID NO:111);

MI[K10Q, Y12F]: Gly-Arg-Cys-Cys-His-Pro-Ala-Cys-Gly-Gln-Asn-Phe-Ser-Cys (SEQ ID NO:112);

MI[K10Q, S13K]: Gly-Arg-Cys-Cys-His-Pro-Ala-Cys-Gly-Gln-Asn-Tyr-Lys-Cys (SEQ ID NO:113);

MI[R2E, K10Q]: Gly-Glu-Cys-Cys-His-Pro-Ala-Cys-Gly-Gln-Asn-Tyr-Ser-Cys (SEQ ID NO:114);

MI[C4E, K10Q, C14K]: Gly-Arg-Cys-Glu-His-Pro-Ala-Cys-Gly-Gln-Asn-Tyr-Ser-Lys (SEQ ID NO:115), wherein Glu4 and Lys14 form a lactam bridge in place of the disulfide bridge in the native MI;

MI[C4E, K10N, C14K]: Gly-Arg-Cys-Glu-His-Pro-Ala-Cys-Gly-Asn-Asn-Tyr-Ser-Lys (SEQ ID NO:116), wherein Glu4 and Lys 14 farm a lactam bridge in place of the disulfide bridge in the native MI;

MI[C4D, K10Q, C14K]: Gly-Arg-Cys-Asp-His-Pro-Ala-Cys-Gly-Gln-Asn-Tyr-Ser-Lys (SEQ ID NO:117), wherein Asp4 and Lys14 form a lactam bridge in place of the disulfide bridge in the native MI;

MI[C4D, K10N, C14K]: Gly-Arg-Cys-Asp-His-Pro-Ala-Cys-Gly-Asn-Asn-Tyr-Ser-Lys (SEQ ID NO:118), wherein Asp4 and Lys14 form a lactam bridge in place of the disulfide bridge in the native MI;

GI[R9Q]: Glu-Cys-Cys-Asn-Pro-Ala-Cys-Gly-Gln-His-Tyr-Ser-Cys (SEQ ID NO:119);

GI[R9N]: Glu-Cys-Cys-Asn-Pro-Ala-Cys-Gly-Asn-His-Tyr-Ser-Cys (SEQ ID NO:120);

GI[C3E, C13K]: Glu-Cys-Glu-Asn-Pro-Ala-Cys-Gly-Arg-His-Tyr-Ser-Lys (SEQ ID NO:121), wherein Glu3 and Lys13 form a lactam bridge in place of the disulfide bridge in the native GI;

GI[C3E, R9Q, C13K]: Glu-Cys-Glu-Asn-Pro-Ala-Cys-Gly-Gln-His-Tyr-Ser-Lys (SEQ ID NO:122), wherein Glu3 and Lys13 form a lactam bridge in place of the disulfide bridge in the native GI;

GI[C3E, R9N, C13K]: Glu-Cys-Glu-Asn-Pro-Ala-Cys-Gly-Asn-His-Tyr-Ser-Lys (SEQ ID NO:123), wherein Glu3 and Lys13 form a lactam bridge in place of the disulfide bridge in the native GI;

GI[C3D, R9Q, C13K]: Glu-Cys-Asp-Asn-Pro-Ala-Cys-Gly-Gln-His-Tyr-Ser-Lys (SEQ ID NO:124), wherein Asp3 and Lys13 form a lactam bridge in place of the disulfide bridge in the native GI; and GI[C3D, R9N, C13K]: Glu-Cys-Asp-Asn-Pro-Ala-Cys-Gly-Asn-His-Tyr-Ser-Lys (SEQ ID NO:125), wherein Asp3 and Lys13 form a lactani bridge in place of the disulfide bridge in the native GI.

The C-terminus is preferably amidated in each of these specific peptides.

The present invention is also directed to novel specific α-conotoxin peptides of class II having the formulas:

Arg-Asp-Xaa$_2$-Cys-Cys-Ser-Asn-Xaa$_2$-Val-Cys-Thr-Val-His-Asn-Xaa$_2$-Gln-Ile-Cys (SEQ ID NO:22);

Arg-Ala-Cys-Cys-Ser-Xaa$_3$-Xaa$_2$-Xaa$_2$-Cys-Asn-Val-Asn-Xaa$_3$-Xaa$_2$-Xaa$_1$-Ile-Cys (SEQ ID NO:23);

Gly-Gly-Cys-Cys-Ser-Xaa$_3$-Xaa$_2$-Xaa$_2$-Cys-Asn-Val-Ser-Xaa$_3$-Xaa$_2$-Xaa$_1$-Ile-Cys (SEQ ID NO:24);

Cys-Cys-Ser-Xaa$_3$-Xaa$_2$-Xaa$_2$-Cys-Asn-Val-Ser-Xaa$_3$-Xaa$_2$-Xaa$_1$-Ile-Cys (SEQ ID NO:25);

Ala-Cys-Cys-Ser-Xaa$_3$-Xaa$_2$-Xaa$_2$-Cys-Asn-Val-Asn-Xaa$_3$-Xaa$_2$-Xaa$_1$-Ile-Cys-Gly-Gly-Arg (SEQ ID NO:26); and Ser-Leu-Leu-Cys-Cys-Thr-Ile-Xaa$_2$-Ser-Cys-Xaa$_4$-Ala-Ser-Xaa$_3$-Xaa$_2$-Asp-Ile-Cys (SEQ ID NO:27), wherein Xaa$_1$ is Glu or γ-carboxy-Glu (Gla); Xaa$_2$ is Pro or hydroxy-Pro; Xaa$_3$ is Tyr, mono-halo-Tyr, di-halo-Tyr, O-sulpho-Tyr, O-phospho-Tyr or nitro-Tyr; Xaa$_4$ is Lys, N-methyl-Lys, N,N-dimethyl-Lys or N,N,N-trimethyl-Lys; and the C-terminus contains a carboxyl or amide group, preferably an amide group. The halo is preferably chlorine or iodine, more preferably iodine. In addition, the His residues may be substituted with halo-His; the Arg residues may be substituted by Lys, ornithine, homoargine, N-methy-Lys, N,N-dimethyl-Lys, N,N,N-trimethyl-Lys or any unnatural basic amino acid (such as N-1-(2-pyrazolinyl)-Arg); the Lys residues may be substituted by Arg, ornithine, homoargine, N-methy-Lys, N,N-dimethyl-Lys, N,N,N-trimethyl-Lys or any unnatural basic amino acid (such as N-1-(2-pyrazolinyl)-Arg); and the Tyr residues may be substituted with $^{125}$I-Tyr or any unnatural hydroxy containing amino acid (such as 4-hydroxymethyl-Phe, 4-hydroxyphenyl-Gly, 2,6-dimethyl-Tyr and 5-amino-Tyr).

More specifically, the present invention is directed to the following α-conotoxin peptides of class II:

P1.2: SEQ ID NO:22, wherein Xaa$_2$ is Pro;

P1.3: SEQ ID NO:23, wherein Xaa$_1$ is Glu, Xaa$_2$ is Pro and Xaa$_3$ is Tyr;

Sl1.4: SEQ ID NO:24, wherein Xaa$_1$ is Glu, Xaa$_2$ is Pro and Xaa$_3$ is Tyr;

Sl1.4A: SEQ ID NO:25, wherein Xaa$_1$ is Glu, Xaa$_2$ is Pro and Xaa$_3$ is Tyr;

Sl1.8: SEQ ID NO:26, wherein Xaa$_1$ is Glu, Xaa$_2$ is Pro and Xaa$_3$ is Tyr; and Ta: SEQ ID NO:27, wherein Xaa$_2$ is Pro, Xaa$_3$ is Tyr and Xaa$_4$ is Lys.

The C-terminus is preferably amidated in each of these specific peptides.

Examples of synthetic aromatic amino acid include, but are not limited to, such as nitro-Phe, 4-substituted-Phe wherein the substituent is $C_1$–$C_3$ alkyl, carboxyl, hyrdroxymethyl, sulphomethyl, halo, phenyl, —CHO, —CN, —$SO_3H$ and —NHAc. Examples of synthetic hydroxy containing amino acid, include, but are not limited to, such as 4-hydroxymethyl-Phe, 4-hydroxyphenyl-Gly, 2,6-dimethyl-Tyr and 5-amino-Tyr. Examples of synthetic basic amino acids include, but are not limited to, N-1-(2-pyrazolinyl)-Arg, 2-(4-piperinyl)-Gly, 2-(4-piperinyl)-Ala, 2-[3-(2S)pyrrolininyl]-Gly and 2-[3-(2S)pyrrolininyl]-Ala. These and other synthetic basic amino acids, synthetic hydroxy containing amino acids or synthetic aromatic amino acids are described in Building Block Index, Version 3.0 (1999 Catalog, pages 4–47 for hydroxy containing amino acids and aromatic amino acids and pages 66–87 for basic amino acids; see also http://www.amino-acids.com), incorporated herein by reference, by and available from RSP Amino Acid Analogues, Inc., Worcester, Mass. Examples of synthetic acid amino acids include those derivatives bearing acidic functionality, including carboxyl, phosphate, sulfonate and synthetic tetrazolyl derivatives such as described by Ornstein et al. (1993) and in U.S. Pat. No. 5,331,001, each incorporated herein by reference.

Optionally, in the peptides of general formulas I and II and the specific peptides and analogs described above, the Asn residues may be modified to contain an N-glycan and the Ser and Thr residues may be modified to contain an O-glycan. In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The gylcan may also include similar polyhydroxy groups, such as D-penicillamine 2,5 and halogenated derivatives thereof or polypropylene glycol derivatives. The glycosidic linkage is beta and 1-4 or 1-3, preferably 1-3. The linkage between the glycan and the amino acid may be alpha or beta, preferably alpha and is 1-.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. Ser. No. 09/420, 797, filed 19 Oct. 1999 and in PCT Application No. PCT/US99/24380, filed 19 Oct. 1999 (PCT Published Application No. WO 00/23092), each incorporated herein by reference. A preferred glycan is Gal($\beta$1→3)GalNAc($\alpha$1→).

Optionally, in the above peptides, pairs of Cys residues may be replaced pairwise with isoteric lactam or ester-thioether replacements, such as Ser/(Glu or Asp), Lys/(Glu or Asp) or Cys/Ala combinations. Sequential coupling by known methods (Barnay et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analogues.

The present invention is further directed to derivatives of the above peptides and peptide derivatives which are acylic permutations in which the cyclic permutants retain the native bridging pattern of native toxin. See Craik et al. (2001).

The present invention is further directed to propeptides and nucleic acid sequences encoding the propeptides or peptides as described in further detail herein.

DETAILED DESCRIPTION OF THE PREFERRED EMBODIMENT

Figure 1:
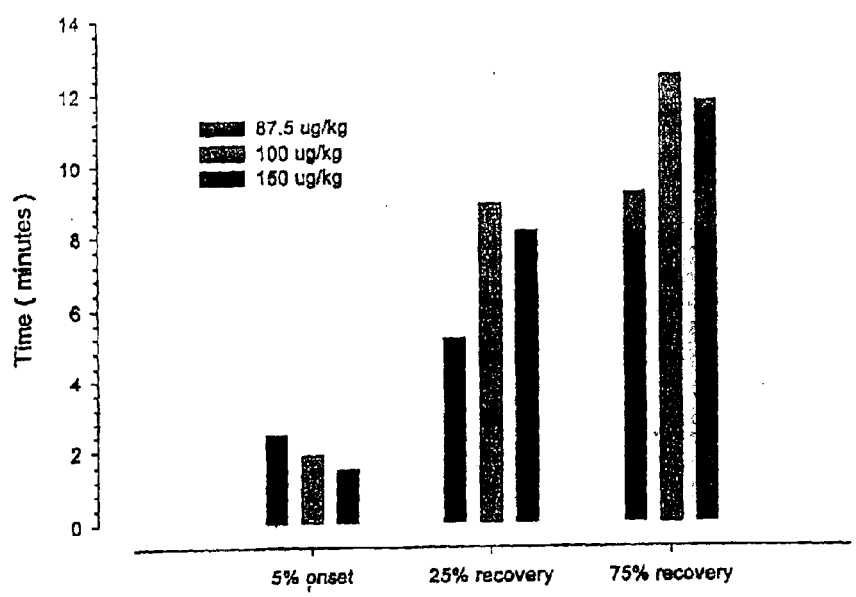
FIG. 1 shows onset and recovery time of neuromuscular block for different doses (87, 100 or 150 µg/kg) of the α-conotoxin peptide MI.

The invention relates to relatively short peptides (termed α-conotoxins herein), about 10–25 residues in length, which are naturally available in minute amounts in the venom of the cone snails or analogous to the naturally available peptides, and which preferably include two disulfide bonds. The α-conotoxins, as described herein, are useful for as neuromuscular blocking agents, such as muscle relaxants, for treating benign essential blepharospasm and other forms of focal dystonia and for anti-wrinkle use.

In one aspect, the present invention relates to a method for providing relaxation of muscle. The method involves administering to a patient an effective amount of an α-conotoxin peptide having the general formula set forth above. Exemplary methods involve administering to a patient an effective amount of MI, GI, EI, mono-iodo-MI ($Tyr_{12}$ of MI having an iodine) or di-iodo-MI ($Tyr_{12}$ of MI having two iodines).

The present invention, in another aspect, relates to a pharmaceutical composition comprising an effective amount of an α-conotoxin peptide having the general formula set forth above. Such a pharmaceutical composition has the capability of acting as a neuromuscular non-depolarizing agent, and hence has the capability of acting as a muscle relaxant. Exemplary pharmaceutical compositions acting as neuromuscular non-depolarizing muscle relaxants include as an active ingredient MI, GI, EI, mono-iodo-MI or di-iodo-MI.

The α-conotoxin peptides described herein are sufficiently small to be chemically synthesized. General chemical syntheses for preparing the foregoing α-conotoxin peptides are described hereinafter. Various ones of the α-conotoxin peptides can also be obtained by isolation and purification from specific *Conus* species using the technique described in U.S. Pat. No. 4,447,356 (Olivera et al., 1984), the disclosure of which is incorporated herein by reference.

Although the α-conotoxin peptides of the present invention can be obtained by purification from cone snails, because the amounts of α-conotoxin peptides obtainable from individual snails are very small, the desired substantially pure α-conotoxin peptides are best practically obtained in commercially valuable amounts by chemical synthesis using solid-phase strategy. For example, the yield from a single cone snail may be about 10 micrograms or less of α-conotoxin peptide. By "substantially pure" is meant that the peptide is present in the substantial absence of other biological molecules of the same type; it is preferably present in an amount of at least about 85% purity and preferably at least about 95% purity. Chemical synthesis of biologically active α-conotoxin peptides depends of course upon correct determination of the amino acid sequence.

The α-conotoxin peptides can also be produced by recombinant DNA techniques well known in the art. Such techniques are described by Sambrook et al. (1989). The peptides produced in this manner are isolated, reduced if necessary, and oxidized to form the correct disulfide bonds.

One method of forming disulfide bonds in the conantokin peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. Nos. 3,842,067 (1974) and 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or param-ethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the a-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodiimide in N-methylpyrrolidinone (NMP) or by 2-(1H-benzotriazole-1-yl)-1,1,3,3-tetramethyluronium hexafluorophosphate (HBTU) and diethylisopropylethylamine (DIEA). The FMOC protecting group is removed by treatment with a 20% solution of piperidine in dimethylformamide(DMF). Resins are subsequently washed with DMF (twice), followed by methanol and NMP.

The compounds described herein are used as neurmuscular blocking agents in conjunction with surgery or for intubation of the trachea by conventional parenteral administration e.g., intramuscular or intravenous administration in solution. Thus, the present invention relates to a method for treating a patient during surgical procedures requiring anesthesia and musculoskeletal relaxation. In particular, the method comprises administering to the patient an amount of a compound effective for providing relaxation of muscle. The method involves administering an effective amount of a compound selected from the general formulae which are set forth hereinbefore. The present invention relates to a pharmaceutical composition incorporating a compound described herein or its pharmaceutically acceptable salts.

The manner in which the compounds are administered can vary. Although it is possible to administer the compound in the form of a bulk active chemical, it is preferred to present the compound in the form of a pharmaceutical composition or formulation for parenteral administration. Pharmaceutical compositions containing a compound of the present invention as the active ingredient can be prepared according to conventional pharmaceutical compounding techniques. See, for example, *Remington's Pharmaceutical Sciences,* 18th Ed. (1990, Mack Publishing Co., Easton, Pa.). Typically, an amount of active ingredient effective to provide muscle relaxation will be admixed with a pharmaceutically acceptable carrier.

The pharmaceutical composition also can include various other components as additives or adjuncts. Exemplary pharmaceutically acceptable components or adjuncts include anesthetics, preservatives, antioxidants, bacteriostatic agents, buffering agents, analgesics, anti-inflammatory agents, anti-pyretics, stabilizing agents, thickening agents and suspending agents. Such components can provide additional therapeutic benefit, or act towards preventing any potential side effects which may be posed as a result of administration of the pharmaceutical composition.

Typically, the pharmaceutical composition is administered as an aqueous or non-aqueous solution, as a suspension, or as an emulsion in a pharmaceutically acceptable liquid or mixture of liquids. The compound within the pharmaceutical composition is administered internally by injection or intravenously. For example, the pharmaceutical composition can be administered intravenously as an infusion (e.g., within aqueous dextrose or saline solutions).

Exemplary methods for administering such muscle relaxant compounds (e.g., so as to achieve sterile or aseptic conditions) will be apparent to the skilled artisan. Certain methods suitable for administering compounds useful according to the present invention are set forth in Goodman and Gilman's *The Pharmacological Basis of Therapeutics,* 7th Ed. (1985). The administration to the patient can be intermittent; or at a gradual, continuous, constant or controlled rate. Administration can be to a warm-blooded animal (e.g. a mammal, such as a mouse, rat, cat, rabbit, dog, pig, cow or monkey); but advantageously is administered to a human being. Administration occurs after general anesthesia is administered. The frequency of administration normally is determined by an anesthesiologist, and typically varies from patient to patient.

The dose of the compound is that amount effective to provide a desired effect for a desired time frame. By "effective amount" or "effective dose" is meant that amount parenterally administered (e.g., injected intravenously) sufficient to bind to relevant receptor sites on the musculoskeletal fiber of the patient, and to elicit neuropharmacological effects (e.g., elicit brief depolarization, thus resulting in effective short duration relaxation of skeletal muscle). Short duration typically ranges from about 5 to about 60 minutes.

An effective amount of the compound administered to a patient provides rapid onset and short-lived muscle relaxation. For adult human patients undergoing short surgical procedures, the effective dose of typical compounds injected intravenously generally is from about 0.001 mg/kg to about 0.8 mg/kg body weight, preferably from about 0.05 mg/kg to about 0.5 mg/kg, and more preferably from about 0.05 mg/kg to about 0.3 mg/kg. Following administration of typical compounds in such a concentration range, the onset of paralysis normally develops within 1 to 2 minutes, and is reversible (i.e., muscle tone returns within a short period of time). The compounds of this invention would normally be readministered every 15 to 30 minutes after initial administration or given as a slow continuous infusion depending upon the length of time a muscular block is desired, and as determined by the anesthetist and surgeon in charge of the patient. For adult human patients undergoing long surgical procedures, the effective dose of typical compounds is administered through continuous or intermittent intravenous perfusion at a rate from about 0.001 mg/min to about 0.8 mg/min, preferably from about 0.01 mg/min to about 0.5 mg/min, and more preferably from about 0.01 to about 0.25 mg/min. Following administration of typical compounds in the specified amounts, the onset of paralysis typically develops within 1 to 2 minutes and persists for the duration of the superfusion.

For human patients in the pediatric population undergoing short surgical procedures, the effective dose of typical compounds injected intravenously generally is from about 0.001 mg/kg to about 0.5 mg/kg body weight, preferably from about 0.01 mg/kg to about 0.4 mg/kg, and more preferably from about 0.01 mg/kg to about 0.25 mg/kg. Following administration of typical compounds in such a concentration range, the onset of paralysis normally develops within 1 to 2 minutes, and persists for a short period of time before recovery is achieved. For infants and children undergoing long surgical procedures, the effective dose of typical compounds is administered through continuous or intermittent intravenous perfusion at a rate from about 0.001 mg/min to about 0.5 mg/min, preferably from about 0.005 mg/min to about 0.3 mg/min, and more preferably from about 0.005 mg/min to about 0.2 mg/min. The total amount of drug administered using such a parenteral route of administration generally does not exceed a total of 10 mg, often does not exceed 5 mg and frequently does not exceed 2 mg. Following administration of typical compounds in the specified amounts, the onset of paralysis typically develops within 1 to 2 minutes and persists for the duration of the superfusion.

Such formulations are normally presented in unit dosage forms such as ampoules or disposable injection devices, or in multidose forms such as a bottle from which the appropriate dose may be withdrawn. All such formulations should be rendered sterile.

The compounds of this invention may be presented as a powder e.g., as a unit dose in a sealed vial to which sterile water may be added by a needle, e.g., through a seal thereof (such as rubber). A suitable unit dose to obtain a neuromuscular block for mammals is about 1 mg to 100 mg and most preferably 3 to 50 mg. Thus a suitable pharmaceutical parenteral preparation will preferably contain 20 to 100 mg of the compounds described herein in solution. A pharmaceutical formulation may conventional contain 5 to 400 mg, or 10 to 400 mg, and most preferably 5 to 200 mg of the compounds of this invention. A simple and preferred formulation is a solution of a compound described herein in water which may be prepared by simply dissolving the compound into previously sterilized pure, i. e., pyrogen free water under aseptic conditions and sterilizing the solution. The compounds described herein may also be administered as an infusion of a dextrose solution or a saline solution e.g., Ringers' Solution.

EXAMPLES

The present invention is described by reference to the following Examples, which are offered by way of illustration and are not intended to limit the invention in any manner. Standard techniques well known in the art or the techniques specifically described below were utilized.

Example 1

Dose-Effect Study for MI and GI

This study was an open label, dose-ranging, single center investigation. A total of 14 rats were studied (10 in each of five groups). All animals were anesthetized with pentobarbital (60 mg/kg) given by intraperitoneal administration and maintained with supplemental doses as determined by physiological monitoring variables. A tracheotomy was performed and the rats were ventilated with room air keeping $P_{CO2}$ near 35 torr. The carotid artery was cannulated to measure blood pressure and arterial blood gases. The right jugular vein was cannulated for intravenous infusion and further drug administration. Body temperature was maintained at 36°–38° C. during the entire experiment. The sciatic nerve was exposed in the popliteal space and stimulated with train-of-four stimulation using a Digistim nerve stimulator. The tivialis anterior muscle contractoin was measured by attaching the rat hind limb to an isometric force transducer to record the evoked response. Prior to administration of the study drug, baseline measurements of blood pressure, heart rate and muscle contraction force were measured for a five-minute period and at five minute intervals for the duration of the study.

The initial dose for analysis was based on biologically effective doses determined in mice. Based on the onset, maximum effect and duration of effect from the first animal studied, the dose for the next animal was either doubled or halved. If the relaxation level was maintained at a maximal level for greater than 20 minutes from this initial dose, then the subsequent dose studied was doubled. this progression continued until the dose that produced near maximal muscle relaxation was found.

The conopeptide derivatives MI and GI were studied in the initial study. For each compound studied, the onset of muacle relaxation, duration of relaxation and an estimate of the $ED_{50}$ was determined from evoked force transducer response. Onset of relaxation is defined as the time for the evoked response to diminish to 5% of pre-drug baseline. In addition, clinical duration, defined as the time from the administration of drug until the evoked muscle response returns to 25% of its pre-drug baseline, and recovery time, defined as tghe time until evoked response returns to 75% of baseline, were also determined. Data were summarized for each compound.

Figure 2:
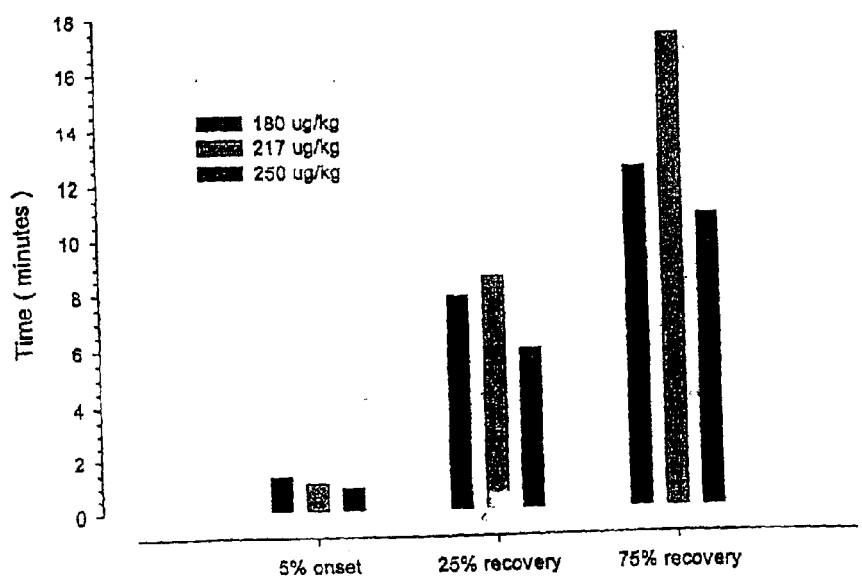
FIG. 2 shows onset and recovery time of neuromuscular block for different doses (180, 217 or 250 µg/kg) of α-conotoxin peptide GI

The onset and recovery results for both MI and GI are shown in FIGS. 1 and 2, respectively. MI had a shortest onset of 1.46 minutes. The onset time increased with decreasting dose size as is typical for may neuromuscular blocking agents. The recovery time to 25% and 75% of baseline occurred in approximately 8 and 12 minutes, respectively. These recovery times were constant for doses over 100 µg/kg, which implies that recovery of thge drug effects is very rapid and not easily saturated in its capacity. Anesthetic drugs that behave in similar fashion tend to be degraded by chemical or enzymatic processes in the body rather than by metabolic organ transformation.

GI had a shorter onset time of just under 1 minute. The time for 25% and 75% recovery of baseline was in the range of 8 and 15 minutes, respectively. As with MI, increasing the dose tended to shorten the onset time without extending the recovery times dramatically. For GI, the onset time was similar to that seen with succinylcholine. The recovery times for both agents were similar to succinylcholine.

A comparison of these results to onset and recovery times for other clinically available neuromuscular blocking agents is shown in Table 1.

TABLE 1

Comparison of Neuromuscular Blocking Agents

| Agent | Onset Time | Recovery (min) | |
|---|---|---|---|
| (mg/kg) | (sec) | 25% | 75% |
| MI (0.15) | 90 | 8 | 12 |
| GI (0.2) | 60–70 | 6–8 | 10–15 |
| Sux (1.0) | 60 | 5–7 | 10 |
| Org 9847 (1.5) | 80 | 8 | 15 |
| Rocuronium (0.6) | 80 | 40 | 60 |
| Mivacurium (0.2) | 150 | 20 | 27 |
| Vecuronium (0.1) | 120–180 | 40 | 60 |
| Cisatracurium (0.1) | 120–180 | 45 | 60–70 |

Figure 3:
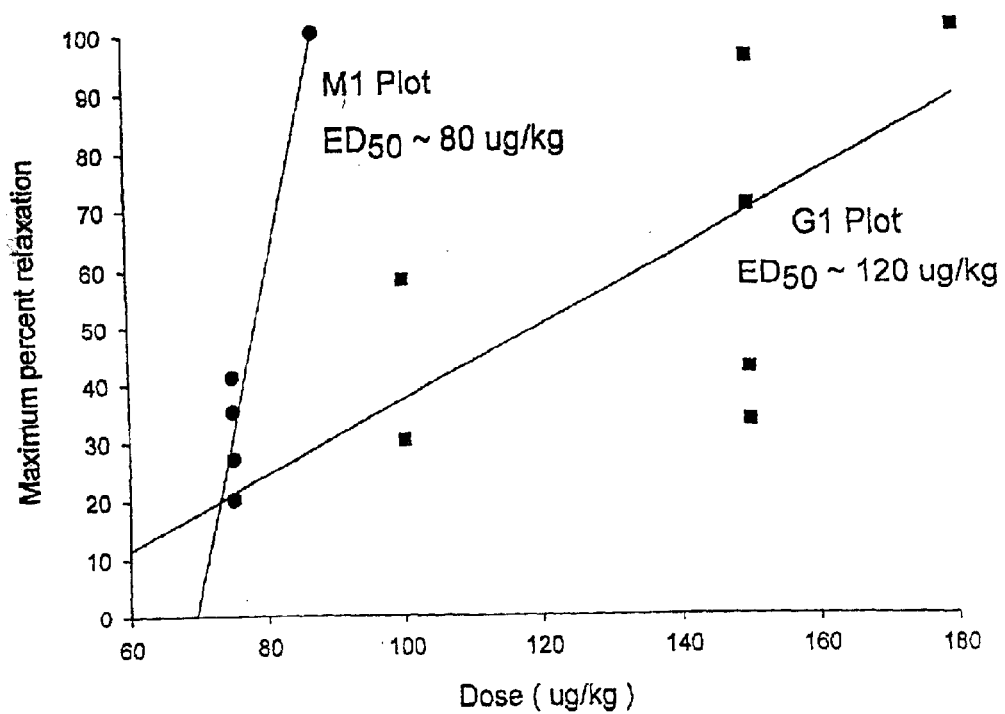
FIG. 3 shows dose response curves for the α-conotoxin peptides MI (●) and GI (■).

For doses of these agents which produced less than maximum levels of neuromuscular block, dose-response plots can be determined to estimate the $ED_{50}$ dose of these agents. In this context, $ED_{50}$ refers to the dose of agent which is expected to produce half of the maximum relaxation level. The data of this initial study (FIG. 3) shows that GI is less potent than MI as reflected in the lower $ED_{50}$ value for MI (~80 µg/kg for MI compared to ~120 µg/kg for GI).

These results show that α-conotoxin peptides are biologically active at the neuromuscular junction producing skeletal muscle paralysis that mimics the repsonse seen with non-depolarizing neuromuscular blocking agents given during anesthesia. The onset and duration of relaxation is rapid and short which is highly desirable for a number of clinical reasons. In this regard, with the rapid onset time, short duration and no prolongation of drug effect with large doses, the clinical benefit of the α-conotoxin peptides exceeds the currently available non-depolarizing neuromuscular blocking agents. In addition to their desirable effect profile, the α-conotoxin peptides appear to have no significant cardiovascular effects on administration. Thus, the desirable effect profile with minimal side effects are desirable clinical properties for the α-conotoxin peptides.

Example 2

Dose-Effect Study for Iodinated-MI

Figure 4:
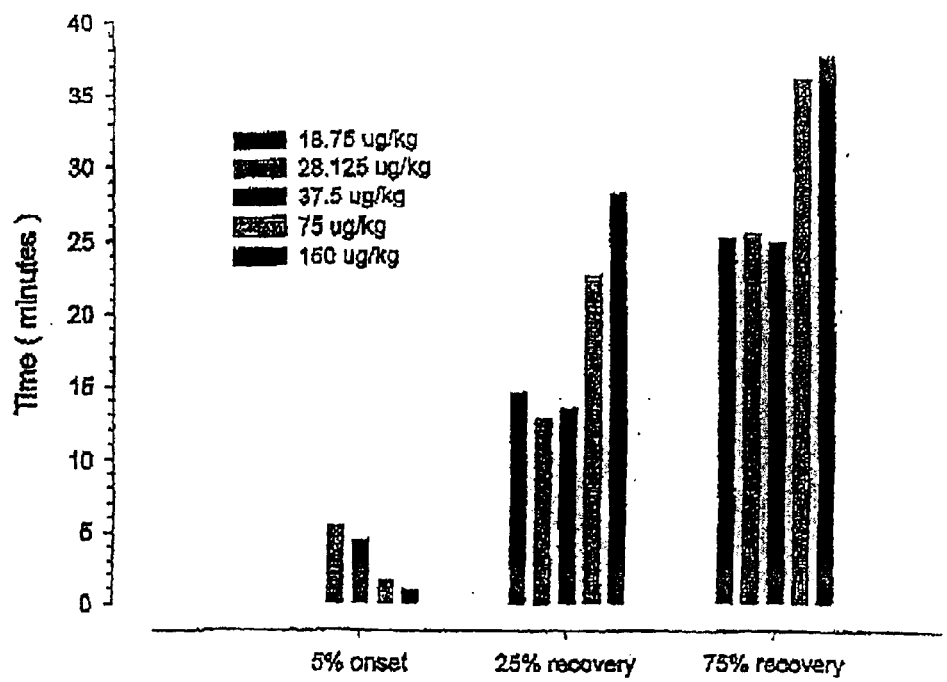
FIG. 4 shows onset and recovery time of neuromuscular block for different doses (18.76, 28.125, 37.5, 75 or 150 µg/kg) of the α-conotoxin peptide mono-iodo-$Tyr_{12}$-MI.
Figure 5:
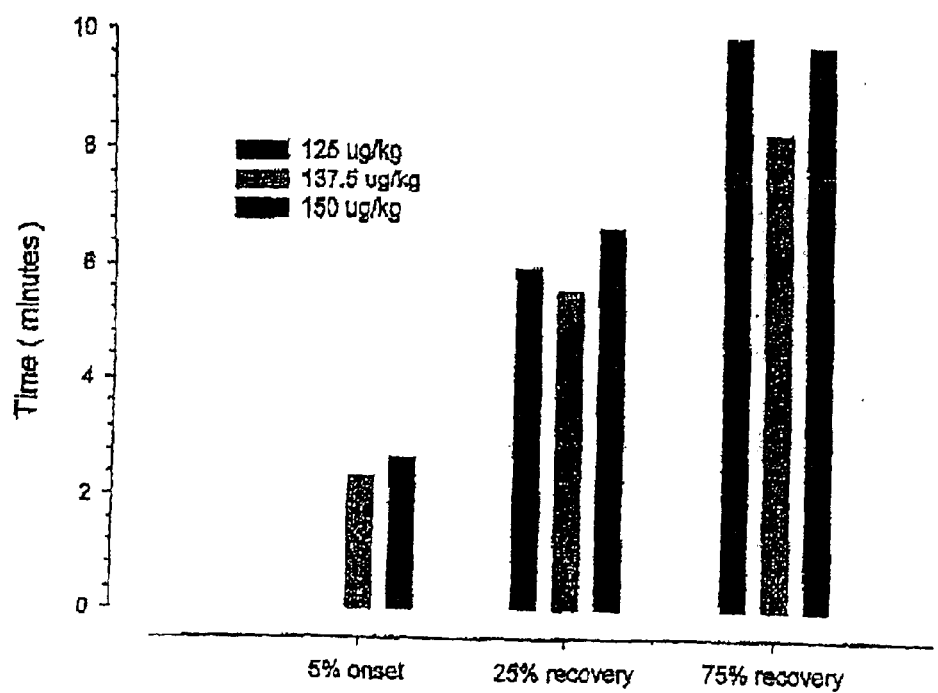
FIG. 5 shows onset and recovery time of neuromuscular block for different doses (125, 137.5 or 150 µg/kg) of the α-conotoxin peptide di-iodo-$Tyr_{12}$-MI.
Figure 6:
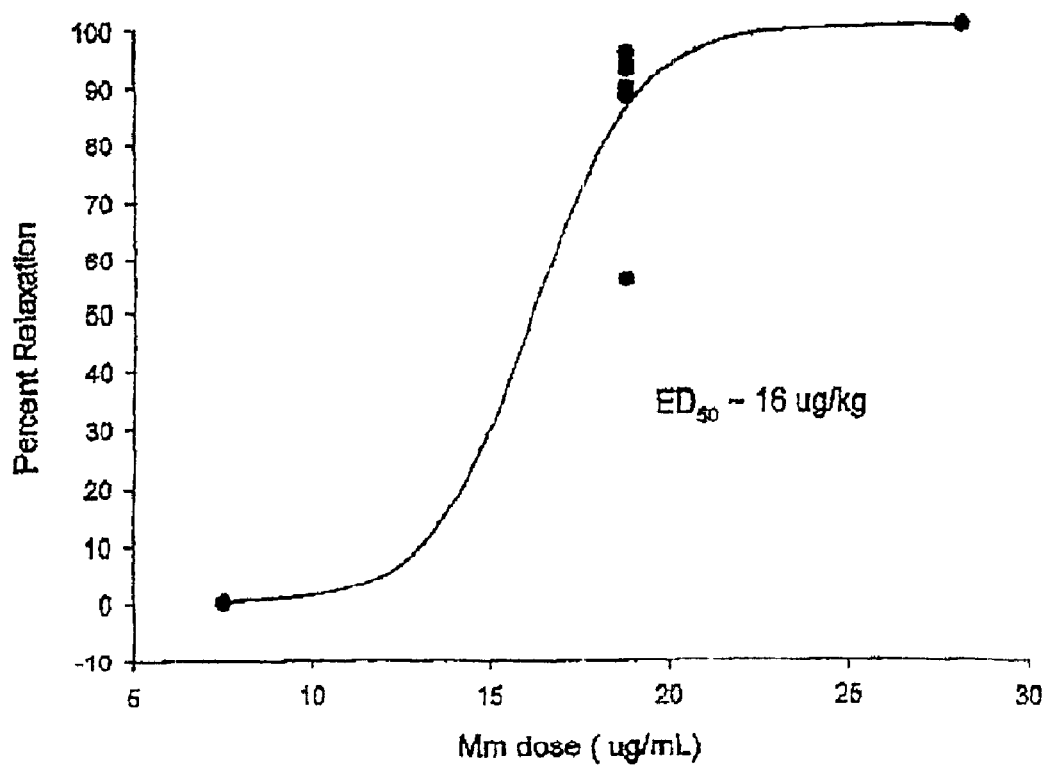
FIG. 6 shows dose response curve for the α-conotoxin peptide mono-iodo-$Tyr_{12}$-MI.
Figure 7:
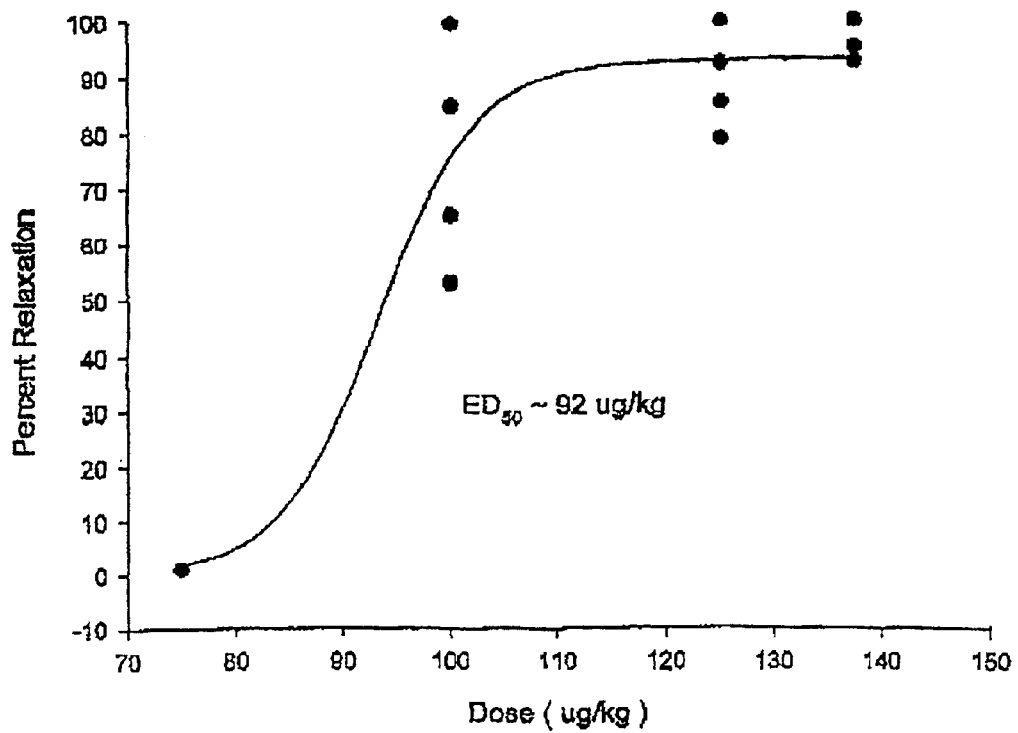
FIG. 7 shows dose response curve for the α-conotoxin peptide di-iodo-$Tyr_{12}$-MI.

A similar study as described in Example 1 was conducted for two iodinated derivatives of MI, namely, mono-iodo-$Tyr_{12}$-MI and di-iodo-$Tyr_{12}$-MI. The onset and recovery results for mono-iodo-$Tyr_{12}$-MI and di-iodo-$Tyr_{12}$-MI are shown in FIGS. 4 and 5, respectively. Dose-response plots for mono-iodo-$Tyr_{12}$-MI and di-iodo-$Tyr_{12}$-MI were made to estimate the $ED_{50}$ dose of these agents. The $ED_{50}$ values are ~16 µg/kg for mono-iodo-$Tyr_{12}$-MI and ~92.5 µg/kg for di-iodo-$Tyr_{12}$-MI.

Example 3

Muscle Relaxant Effect in Anesthetized Monkeys

The peptides MI, GI, EI, mono-iodo-MI and di-iodo-MI are each separately dissolved 0.9 percent saline at a concentration of 2 mg/ml. Rhesus monkeys are anesthetized with halothane, nitrous oxide and oxygen. The maintenance concentration of halothane is 1.0%. Arterial and venous catheters are placed in the femoral vessels for drug administration and recording of the arterial pressure. Controlled ventilation is accomplished via an endotrachael tube. Twitch and tetanic contractions of the tibialis arterior muscle are elicited indirectly via the sciatic nerve. Recordings of arterial pressure electrocardiogram (lead I), heart rate, and muscle function are made simultaneously. Four to six animals received each listed compound. Four additional animals received succinylcholine chloride or d-tubocurarine chloride as controls. Is is seen that the tested compounds generally provide similar or better results than those seen for succinylcholine chloride or d-tubocurarine chloride.

Example 4

Isolation of DNA Encoding α-Conotoxins

DNA coding for α-conotoxins was isolated and cloned in accordance with conventional techniques using general procedures well known in the art, such as described in Olivera et al. (1996). Alternatively, cDNA libraries was prepared from Conus venom duct using conventional techniques. DNA from single clones was amplified by conventional techniques using primers which correspond approximately to the M13 universal priming site and the M13 reverse universal priming site. Clones having a size of approximately 300 nucleotides were sequenced and screened for similarity in sequence to known α-conotoxins. The DNA sequences and encoded propeptide or peptide sequences are set forth in Tables 2–38. It was discovered that the following mature α-conotoxin peptides had the same sequence: (a) R1.4, A1.1, Bt1.6, Cn1.1 and MnI; and (b) Sm1.1 and Cr1.1.

TABLE 2

DNA Sequence (SEQ ID NO:28) and Protein Sequence (SEQ ID NO:29) of GI

```
atg ttc acc gtg ttt ctg ttg gtg gtc ttg gca acc act gtc gtt tcc
Met Phe Thr Val Phe Leu Leu Val Val Leu Ala Thr Thr Val Val Ser ttc cct tca gaa cgt gca tct gat ggc agg gat gac aca gcc aaa gac
Phe Pro Ser Glu Arg Ala Ser Asp Gly Arg Asp Asp Thr Ala Lys Asp gaa ggg tct gac atg gag aaa ttg gtc gag aaa aaa gaa tgt tgc aat
Glu Gly Ser Asp Met Glu Lys Leu Val Glu Lys Lys Glu Cys Cys Asn cct gcc tgt ggc aga cac tac agt tgt gga cgc tgatgctcca ggaccctctg
Pro Ala Cys Gly Arg His Tyr Ser Cys Gly Arg aaccacggac gtgccgccct ctgcctgacc tgcttcactg tccgtctctt tgtgccacta
gaactgaaca gctcgatcca ctagactacc acgttacctc cgtgttctaa aactacttgg
tttagattgc ctttaatttc tagtcatact tcctgttatt acgtcgtcca aaattgaaac
aagaacatga ggggtgtcag ctcaaacaaa atcaggcaat gacaaggaaa atgtctccga
tcgatccgaa aactgtcacc cgtcactctc ttaaccagtt ttagaactga ttaccactag
agcttttgta ccacatcaaa tcaggtctat gtgtgatgtt tcttttgcaa aatttaattt
ttgagaaaaa aagctcaaaa tgtgggaagt gcttttgatt ttctgacaac ttgtgatcat
gtccgttttc agtgagtcta attgcaacct ctgtgtgatt ttcttcacct gttaagcaac
gcaaagaggt tgtccataac caggaaagca acagacaaag aaatgcttga gaatttcagg
ttatagataa ggtaaggaaa aaaggagag ctatgggaaa tgatgaaaac aacagataaa
ataaattgaa cagtacctac ttgtttcatg gttgattttt ttttctctga ataatctctg
tggacactaa tggcagtctc tcctcacccc acgccattag taagcttatt ttttctttct
ttatccaaga tttgctgaac atatttagcc tagatataga cattgctaca tatataatct
gacaataaac tttcatgggc accaatt
```

TABLE 3

DNA Sequence (SEQ ID NO:30) and Protein Sequence (SEQ ID NO:31) of SIB

```
atg ttc acc gtg ttt ctg ttg gtt gtc ttg gca acc act gtc gtt tcc
Met Phe Thr Val Phe Leu Leu Val Val Leu Ala Thr Thr Val Val Ser ttc cct tca gat cgt gca tct gat ggc agg gat gac gaa gcc aaa gac
Phe Pro Ser Asp Arg Ala Ser Asp Gly Arg Asp Asp Glu Ala Lys Asp gaa agg tct gac atg cac gaa tcg gac cgg aaa gaa atc tgt tgc aat
Glu Arg Ser Asp Met His Glu Ser Asp Arg Lys Glu Ile Cys Cys Asn cct gcc tgt ggc cca aag tat agt tgt gga cgc tgatgctcca ggaccctctg
Pro Ala Cys Gly Pro Lys Tyr Ser Cys Gly Arg aacc
```

TABLE 4

DNA Sequence (SEQ ID NO:32) and Protein Sequence (SEQ ID NO:33) of R1

```
atg ttc acc gtg ttt ctg ttg gtt gtc ttg aca atc act gtc gtt tcc
Met Phe Thr Val Phe Leu Leu Val Val Leu Thr Ile Thr Val Val Ser ttc cct tca gat cgt gca tct gat ggc agg gat gac gaa gcc aaa gac
Phe Pro Ser Asp Arg Ala Ser Asp Gly Arg Asp Asp Glu Ala Lys Asp gaa agg tct gac atg tac aaa tcg aaa cgg aat gga cgc tgt tgc cat
Glu Arg Ser Asp Met Tyr Lys Ser Lys Arg Asn Gly Arg Cys Cys His cct gcc tgt ggc aaa cac ttt agt tgt gga cgc tgatgctcca ggaccctctg
Pro Ala Cys Gly Lys His Phe Ser Cys Gly Arg aaccacgacg t
```

TABLE 5

DNA Sequence (SEQ ID NO:34) and Protein Sequence (SEQ ID NO:35) of R1.3

```
atg ttc acc gtg ttt ctg ttg gtg gtc ttg gca acc act gtc gtt tcc
Met Phe Thr Val Phe Leu Leu Val Val Leu Ala Thr Thr Val Val Ser ttc cct tca gaa cgt gca tct gat ggc agg gat gac aca gcc aaa gac
Phe Pro Ser Glu Arg Ala Ser Asp Gly Arg Asp Asp Thr Ala Lys Asp gaa ggg tct gac atg gag aaa ttg gtc gag aaa aaa gaa tgt tgc aat
Glu Gly Ser Asp Met Glu Lys Leu Val Glu Lys Lys Glu Cys Cys Asn cct gcc tgt ggc aga cac tac agt tgt aag gga ggacgctgat gctccagacc
Pro Ala Cys Gly Arg His Tyr Ser Cys Lys Gly ctctgaacca cgacgt
```

TABLE 6

DNA Sequence (SEQ ID NO:36) and Protein Sequence (SEQ ID NO:37) of R1.4

```
atg ttc acc gtg ttt ctg ttg gtt gtc ttg aca atc act gtc gtt tcc
Met Phe Thr Val Phe Leu Leu Val Val Leu Thr Ile Thr Val Val Ser ttc cct tca gat cgt gca tct gat ggc agg gat gac gaa gcc aaa gac
Phe Pro Ser Asp Arg Ala Ser Asp Gly Arg Asp Asp Glu Ala Lys Asp gaa agg tct gac atg tac aaa tcg aaa cgg aat gga cgc tgt tgc cat
Glu Arg Ser Asp Met Tyr Lys Ser Lys Arg Asn Gly Arg Cys Cys His cct gcc tgt ggc aaa cac ttt agt tgt gga cgc tgatgctcca ggaccctctg
Pro Ala Cys Gly Lys His Phe Ser Cys Gly Arg aaccacgacg t
```

TABLE 7

DNA Sequence (SEQ ID NO:28) and Protein Sequence (SEQ ID NO:39) of Sm1.1

```
atg ttc acc gtg ttt ctg ttg gtt gtc ttg gca acc act gtc gtt tcc
Met Phe Thr Val Phe Leu Leu Val Val Leu Ala Thr Thr Val Val Ser ttc cct tca gat cgt gca tct gat ggc agg gat gac gaa gcc aaa gac
Phe Pro Ser Asp Arg Ala Ser Asp Gly Arg Asp Asp Glu Ala Lys Asp gaa agg tct gac atg cac gaa tcg ggc cgg aaa gga cgc gga cgc tgt
Glu Arg Ser Asp Met His Glu Ser Gly Arg Lys Gly Arg Gly Arg Cys tgc cat cct gcc tgt ggc cca aac tat agt tgt ggacgctgat gctccaggac
Cys His Pro Ala Cys Gly Pro Asn Tyr Ser Cys cctctgaacc acgacgt
```

TABLE 8

DNA Sequence (SEQ ID NO:40) and Protein Sequence (SEQ ID NO:41) of SIIA

```
atg ttc acc gtg ttt ctg ttg gtt gtc ttg gca acc act gtc gtt tcc
Met Phe Thr Val Phe Leu Leu Val Val Leu Ala Thr Thr Val Val Ser ttc cct tca gat cgt gca tct gat ggc agg gat gac gaa gcc aaa gac
Phe Pro Ser Asp Arg Ala Ser Asp Gly Arg Asp Asp Glu Ala Lys Asp gaa agg tct gac atg cac gaa tcg gac cgg aat gga cgc gga tgc tgt
Glu Arg Ser Asp Met His Glu Ser Asp Arg Asn Gly Arg Gly Cys Cys tgc aat cct gcc tgt ggc cca aac tat ggt tgt ggc acc tca tgc tcc
Cys Asn Pro Ala Cys Gly Pro Asn Tyr Gly Cys Gly Thr Ser Cys Ser
```

TABLE 8-continued

DNA Sequence (SEQ ID NO:40) and Protein Sequence (SEQ ID NO:41) of SIIA

```
agg acc ctc tgaaccacga cgttcgagca
Arg Thr Leu
```

TABLE 9

DNA Sequence (SEQ ID NO:42) and Protein Sequence (SEQ ID NO:43) of S11

```
tgt tgc cat cct gcc tgt ggc aga aag tat aat tgt gga cgc tga
Cys Cys His Pro Ala Cys Gly Arg Lys Tyr Asn Cys Gly Arg
```

TABLE 10

DNA Sequence (SEQ ID NO:44) and Protein Sequence (SEQ ID NO:45) of S2

```
tgc tgt tgc aat cct gcc tgt ggc cca aac tat ggt tgt ggc acc tca
Cys Cys Cys Asn Pro Ala Cys Gly Pro Asn Tyr Gly Cys Gly Thr Ser tgc tcc aga ccc tct gaa cca cga cgt tag
Cys Ser Arg Pro Ser Glu Pro Arg Arg
```

TABLE 11

DNA Sequence (SEQ ID NO:46) and Protein Sequence (SEQ ID NO:47) of GIB

```
atg ttc acc gtg ttt ctg ttg gtg gtc ttg gca acc act gtc gtt tcc
Met Phe Thr Val Phe Leu Leu Val Val Leu Ala Thr Thr Val Val Ser ttc cct tca gaa cgt gca tct gat ggc agg gat gac aca gcc aaa gac
Phe Pro Ser Glu Arg Ala Ser Asp Gly Arg Asp Asp Thr Ala Lys Asp gaa ggg tct gac atg gag aaa ttg gtc gag aaa aaa gaa tgt tgc aat
Glu Gly Ser Asp Met Glu Lys Leu Val Glu Lys Lys Glu Cys Cys Asn cct gcc tgt ggc aga cac tac agt tgt aag gga ggacgctgat gctccaggac
Pro Ala Cys Gly Arg His Tyr Ser Cys Lys Gly cctctgaacc acggacgtgc cgccctctgc ctgacctgct tcactgtccg tctctttgtg
ccactagaac tgaacagctc gatccactag actaccacgt tacctccgtg ttctaaaact
acttggttta gattgccttt aatttctagt catacttcct gttattacgt cgtccaaaat
tgaaacaaga acatgagggg tgtcagctca aacaaaatca ggcaatgaca aggaaaatgt
ctccgatcga tccgaaaact gtcacccgtc actctcttaa ccagtttag aactgattac
cactagagct tttgtaccac atcaaatcag gtctatgtgt gatgtttctt ttgcaaaatt
taattttga gaaaaaagc tcaaaatgtg ggaagtgctt ttgattttct gcaacttgt
gatcatgtcc gttttcagtg agtctaattg caacctctgt gtgattttct tcacctgtta
agcaacgcaa agaggttgtc cataaccagg aaagcaacag acaaagaaat gcttgagaat
ttcaggttat agataaggta aggaaaaaa ggagagctat gggaaatgat gaaaacaaca
gataaaataa attgaacagt acctacttgt ttcatggttg attttttttt ctctgaataa
tctctgtgga cactaatggc agtctctcct caccccacgc cattagtaag cttatttttt
ctttctttat ccaagatttg ctgaacatat ttagcctaga tatagacatt gctacatata
taatctgaca ataaactttc atgggcacca att
```

TABLE 12

DNA Sequence (SEQ ID NO:48) and Protein Sequence (SEQ ID NO:49) of MnII

```
atg ttc acc gtg ttt ctg ttg gtt gtc ttg aca acc act gtc gtt tcc
Met Phe Thr Val Phe Leu Leu Val Val Leu Thr Thr Thr Val Val Ser ttc cct tca gat agt gca tct ggt ggc agg gat gac gag gcc aaa gac
Phe Pro Ser Asp Ser Ala Ser Gly Gly Arg Asp Asp Glu Ala Lys Asp gaa agg tct gac atg tac gaa ttg aaa cgg aat gga cac tgt tgc cat
Glu Arg Ser Asp Met Tyr Glu Leu Lys Arg Asn Gly His Cys Cys His
```

TABLE 12-continued

DNA Sequence (SEQ ID NO:48) and
Protein Sequence (SEQ ID NO:49) of MnII cct gcc tgt ggt ggc aaa tac gtt aaa tgt gga cgc tgatgctcca
Pro Ala Cys Gly Gly Lys Tyr Val Lys Cys Gly Arg ggaccctctc gaaccacg

TABLE 13

DNA Sequence (SEQ ID NO:50) and
Protein Sequence (SEQ ID NO:51) of A1.2 atg ttc acc gtg ttt ctg ttg gtt gtc ttg aca acc act gtc gtt tcc
Met Phe Thr Val Phe Leu Leu Val Val Leu Thr Thr Thr Val Val Ser ttc cct tca gat agt gca tct ggt ggc agg gat gac gag gcc aaa gac
Phe Pro Ser Asp Ser Ala Ser Gly Gly Arg Asp Asp Glu Ala Lys Asp gaa agg tct gac atg tac gaa ttg aaa cgg aat gga cgc tgt tgc cat
Glu Arg Ser Asp Met Tyr Glu Leu Lys Arg Asn Gly Arg Cys Cys His cct gcc tgt ggt ggc aaa tac gtt aaa tgt gga cgc tgatgctcca
Pro Ala Cys Gly Gly Lys Tyr Val Lys Cys Gly Arg ggaccctctc gaaccacg

TABLE 14

DNA Sequence (SEQ ID NO:52) and
Protein Sequence (SEQ ID NO:53) of A1.1 atg ttc acc gtg ttt ctg ttg gtt gtc ttg aca aca act gtc gtt tcc
Met Phe Thr Val Phe Leu Leu Val Val Leu Thr Thr Thr Val Val Ser tac cct tca gat agt gca tct gat ggc agg gat gac gaa gcc aaa gac
Tyr Pro Ser Asp Ser Ala Ser Asp Gly Arg Asp Asp Glu Ala Lys Asp gaa agg tct gac atg tac aaa tcg aaa cgg aat gga cgc tgt tgc cat
Glu Arg Ser Asp Met Tyr Lys Ser Lys Arg Asn Gly Arg Cys Cys His cct gcc tgt ggc aaa cac ttt agt tgt gga cgc tgatgctcca ggaccctctg
Pro Ala Cys Gly Lys His Phe Ser Cys Gly Arg aaccacgacg t

TABLE 15

DNA Sequence (SEQ ID NO:54) and
Protein Sequence (SEQ ID NO:55) of Bt1.6 atg ttc acc gtg ttt ctg ttg gtt gtc ttg gca acc act gtc gtt tcc
Met Phe Thr Val Phe Leu Leu Val Val Leu Ala Thr Thr Val Val Ser tac cct tca gat agt gca tct gat ggc agg gat gac gaa acc aaa gac
Tyr Pro Ser Asp Ser Ala Ser Asp Gly Arg Asp Asp Glu Thr Lys Asp gaa aag tct gac atg tac aaa tcg aaa cgg aat gga cgc tgt tgc cat
Glu Lys Ser Asp Met Tyr Lys Ser Lys Arg Asn Gly Arg Cys Cys His cct gcc tgt ggc aaa cac ttt agt tgt gga cgc tgatgctgca ggaccctctg
Pro Ala Cys Gly Lys His Phe Ser Cys Gly Arg aaccacgacg t

TABLE 16

DNA Sequence (SEQ ID NO:56) and
Protein Sequence (SEQ ID NO:57) of Cn1.1

| | | | | | | | | | | | | | |
|---|---|---|---|---|---|---|---|---|---|---|---|---|---|
| atg | tte | acc | gtg | ttt | ctg | ttg | gtt | gtc | ttg | aca | acc | act | gtc | gtt | tcc |
| Met | Phe | Thr | Val | Phe | Leu | Leu | Val | Val | Leu | Thr | Thr | Thr | Val | Val | Ser | ttc cct tca gat agt gca tct gat gtc agg gat gac gaa gcc aaa gac
Phe Pro Ser Asp Ser Ala Ser Asp Val Arg Asp Asp Glu Ala Lys Asp gaa agg tct gac atg tac aaa tcg aaa cgg aat gga cgc tgt tgc cat
Glu Arg Ser Asp Met Tyr Lys Ser Lys Arg Asn Gly Arg Cys Cys His cct gcc tgt ggc aaa cac ttt agt tgt gga cgc tgatgctcca ggaccctctg
Pro Ala Cys Gly Lys His Phe Ser Cys Gly Arg aaccacgacg t

TABLE 17

DNA Sequence (SEQ ID NO:58) and
Protein Sequence (SEQ ID NO:59) of MnI atg ttc acc gtg ttt ctg ttg gtt gtc ttg aca aca act gtc gtt tcc
Met Phe Thr Val Phe Leu Leu Val Val Leu Thr Thr Thr Val Val Ser tac cct tca gat agt gca tct gat ggc agg gat gac gaa gcc aaa gac
Tyr Pro Ser Asp Ser Ala Ser Asp Gly Arg Asp Asp Glu Ala Lys Asp gaa agg tct gac atg tac aaa tcg aaa cgg aat gga cgc tgt tgc eat
Glu Arg Ser Asp Met Tyr Lys Ser Lys Arg Asn Gly Arg Cys Cys His cct gcc tgt ggc aaa cac ttt agt tgt gga cgc tgatgctcca ggaccctctg
Pro Ala Cys Gly Lys His Phe Ser Cys Gly Arg aaccacgacg t

TABLE 18

DNA Sequence (SEQ ID NO:60) and
Protein Sequence (SEQ ID NO:61) of Cr1.1 atg ttc acc gtg ttt ctg ttg gtt gtc ttg gca gcc act gtc gtt tcc
Met Phe Thr Val Phe Leu Leu Val Val Leu Ala Ala Thr Val Val Ser ttc cct tca gat cgt gca tct gat ggc agg gat gac gaa gcc aaa gac
Phe Pro Ser Asp Arg Ala Ser Asp Gly Arg Asp Asp Glu Ala Lys Asp gaa aga tct gac atg cac gaa tcg gac cgg aaa gga cgc gga cgc tgt
Glu Arg Ser Asp Met His Glu Ser Asp Arg Lys Gly Arg Gly Arg Cys tgc cat cct gcc tgt ggc cca aat tat agt tgt gga cgc tgatgctcca
Cys His Pro Ala Cys Gly Pro Asn Tyr Ser Cys Gly Arg ggaccctctg aaccacgacg

TABLE 19

DNA Sequence (SEQ ID NO:62) and
Protein Sequence (SEQ ID NO:63) of R1.2 atg ttc acc gtg ttt ctg ttg gtg gtc ttg gca acc act gtc gtt tcc
Met Phe Thr Val Phe Leu Leu Val Val Leu Ala Thr Thr Val Val Ser ttc cct tca gaa cgt gca tct gat ggc agg gat gac aca gcc aaa gac
Phe Pro Ser Glu Arg Ala Ser Asp Gly Arg Asp Asp Thr Ala Lys Asp gaa ggg tct gac atg gac aaa ttg gtc gag aaa aaa gaa tgt tgc cat
Glu Gly Ser Asp Met Asp Lys Leu Val Glu Lys Lys Glu Cys Cys His cct gcc tgt ggc aaa cac ttc agt tgt gga cgc tgatgctcca ggaccctctg
Pro Ala Cys Gly Lys His Phe Ser Cys Gly Arg aaccacgacg t

TABLE 20

DNA Sequence (SEQ ID NO:64) and
Protein Sequence (SEQ ID NO:65) of A1.3 tct gat ggc agg gat gac gaa gcc aaa gac gaa agg tct gac atg tac
Ser Asp Gly Arg Asp Asp Glu Ala Lys Asp Glu Arg Ser Asp Met Tyr aaa tcg aaa cgg aat gga cgc tgt tgc cac cct gcc tgt ggc aaa cac
Lys Ser Lys Arg Asn Gly Arg Cys Cys His Pro Ala Cys Gly Lys His ttt att tgt gga cgc tga
Phe Ile Cys Gly Arg

TABLE 21

DNA Sequence (SEQ ID NO:66) and
Protein Sequence (SEQ ID NO:67) of A1.7 tct ggt ggc agg gat gac gaa gcc aaa gac gaa agg tct gac atg tac
Ser Gly Gly Arg Asp Asp Glu Ala Lys Asp Glu Arg Ser Asp Met Tyr gaa tcg gac cgg aat gga cgc tgt tgc cat cct gcc tgt ggc aaa cac
Glu Ser Asp Arg Asn Gly Arg Cys Cys His Pro Ala Cys Gly Lys His ttt agt tgt gga cgc tga
Phe Ser Cys Gly Arg

TABLE 22

DNA Sequence (SEQ ID NO:68) and Protein Sequence (SEQ ID NO:69)
of A1.8 tct gat ggc agg gat gac gaa gcc aaa gac aaa agg tct gac atg tac
Ser Asp Gly Arg Asp Asp Glu Ala Lys Asp Lys Arg Ser Asp Met Tyr gaa tcg gac cgg aat gga cgc tgt tgc cat cct tcc tgt ggc aga aag
Glu Ser Asp Arg Asn Gly Arg Cys Cys His Pro Ser Cys Gly Arg Lys tat aat tgt gga cgc tga
Tyr Asn Cys Gly Arg

TABLE 23

DNA Sequence (SEQ ID NO:70) and Protein Sequence (SEQ ID NO:71)
of Ay1.1 tctgatggca gggatgacga agccaaagac gaaaggtctg acatgtac gaa tcg gac
                                                    Glu Ser Asp cgg aat gga cgc tgt tgc cat cct gcc tgt gcg aga aag tat aat tgt
Arg Asn Gly Arg Cys Cys His Pro Ala Cys Ala Arg Lys Tyr Asn Cys gga cgc tgatgctcca ggaccctctg aaccacgacg t
Gly Arg

TABLE 24

DNA Sequence (SEQ ID NO:72) and Protein Sequence (SEQ ID NO:73)
of Ay1.1a tctgatggca gggatgacga agccaaagac gaaaggtctg acatgtac gaa tcg gag
                                                    Glu Ser Glu cgg aat gaa cgc tgt tgc cat cct gcc tgt gcg aga aag tat aat tgt
Arg Asn Glu Arg Cys Cys His Pro Ala Cys Ala Arg Lys Tyr Asn Cys gga cgc tgatgctcca ggaccctctg aaccacgacg t
Gly Arg

TABLE 25

DNA Sequence (SEQ ID NO:74) and Protein Sequence (SEQ ID NO:75) of M1.1

```
atg ttc acc gtg ttt ctg ttg gtt gtc ttg aca acc act gtc gtt tcc
Met Phe Thr Val Phe Leu Leu Val Val Leu Thr Thr Thr Val Val Ser ttc cct tca gat cgt gca tct gat ggc agg gat gac gaa gcc aaa gac
Phe Pro Ser Asp Arg Ala Ser Asp Gly Arg Asp Asp Glu Ala Lys Asp gaa agg tct gac atg tac gaa tcg aaa cgg gat gga cgc tgt tgc cat
Glu Arg Ser Asp Met Tyr Glu Ser Lys Arg Asp Gly Arg Cys Cys His cct gcc tgt ggg caa aac tat agt tgt gga cgc tgatgctcca ggaccctctg
Pro Ala Cys Gly Gln Asn Tyr Ser Cys Gly Arg aaccacgacg t
```

TABLE 26

DNA Sequence (SEQ ID NO:76) and Protein Sequence (SEQ ID NO:77) of M1.3

```
tct gat ggc agg gat gac gaa gcc aaa gac gaa agg cct gac atg tac
Ser Asp Gly Arg Asp Asp Glu Ala Lys Asp Glu Arg Pro Asp Met Tyr aaa tcg aaa cgg gat gga cgc tgt tgc cat cct gcc tgt gcg aaa cac
Lys Ser Lys Arg Asp Gly Arg Cys Cys His Pro Ala Cys Ala Lys His ttt aat tgt gga cgc tgatgctcca ggaccctctg aaccacgacg t
Phe Asn Cys Gly Arg
```

TABLE 27

DNA Sequence (SEQ ID NO:78) and Protein Sequence (SEQ ID NO:79) of M1.4

```
tct gat ggc agg gat gac gaa gcc aaa gac gaa agg tct gac atg tac
Ser Asp Gly Arg Asp Asp Glu Ala Lys Asp Glu Arg Ser Asp Met Tyr gaa tcg aaa cgg aat gga cgc tgt tgc cat cct gcc tgt gcg aaa aac
Glu Ser Lys Arg Asn Gly Arg Cys Cys His Pro Ala Cys Ala Lys Asn tat agt tgt gga cgc tgatgctcca ggaccctctg aaccacgacg t
Tyr Ser Cys Gly Arg
```

TABLE 28

DNA Sequence (SEQ ID NO:80) and Protein Sequence (SEQ ID NO:81) of M1.5

```
tct gat ggc agg gat gac gaa gcc aaa gac gaa agg tct gac atg tac
Ser Asp Gly Arg Asp Asp Glu Ala Lys Asp Glu Arg Ser Asp Met Tyr gaa tcg gac cgg aat gga cgc tgt tgc cat cct gcc tgt gcg aga aag
Glu Ser Asp Arg Asn Gly Arg Cys Cys His Pro Ala Cys Ala Arg Lys tat aat tgt gga cgc tgatgctcca ggaccctctg aaccacgacg t
Tyr Asn Cys Gly Arg
```

TABLE 29

DNA Sequence (SEQ ID NO:82) and Protein Sequence (SEQ ID NO:83) of O1.3

```
tctgatggca gggatgacac agccaaaaac aaaggatctg acatgaacaa attg gtc
                                                           Val aag aaa aaa caa tgt tgc aat cct gcc tgt ggc cca aag tat agt tgt
Lys Lys Lys Gln Cys Cys Asn Pro Ala Cys Gly Pro Lys Tyr Ser Cys
```

TABLE 29-continued

DNA Sequence (SEQ ID NO:82) and Protein Sequence (SEQ ID NO:83) of O1.3 gga cac tgatgctcca ggaccctctg aaccacgacg t
Gly His

TABLE 30

DNA Sequence (SEQ ID NO:84) and Protein Sequence (SEQ ID NO:85) of S1.3 tct gat ggc agg gat gac gaa gcc aaa gac gaa agg tct gac atg cac
Ser Asp Gly Arg Asp Asp Glu Ala Lys Asp Glu Arg Ser Asp Met His gaa tcg gac cgg aaa gga cgc gca tac tgt tgc cat cct gcc tgt ggc
Glu Ser Asp Arg Lys Gly Arg Ala Tyr Cys Cys His Pro Ala Cys Gly aaa aag tat aat tgt gga cgc tgatgctcca ggaccctctg aaccacgacg t
Lys Lys Tyr Asn Cys Gly Arg

TABLE 31

DNA Sequence (SEQ ID NO:86) and Protein Sequence (SEQ ID NO:87) of EI atg ttc acc gtg ttt ctg ttg gtt gtc ttg gca acc act gtc ggt tcc
Met Phe Thr Val Phe Leu Leu Val Val Leu Ala Thr Thr Val Gly Ser ttc act tta gat cgt gca tct gat ggt agg gat gcc gca gcc aac gac
Phe Thr Leu Asp Arg Ala Ser Asp Gly Arg Asp Ala Ala Ala Asn Asp aaa gcg tct gac ctg atc gct ctg acc gcc agg aga gat cca tgc tgt
Lys Ala Ser Asp Leu Ile Ala Leu Thr Ala Arg Arg Asp Pro Cys Cys tac cat cct acc tgt aac atg agt aat cca cag att tgt ggt
Tyr His Pro Thr Cys Asn Met Ser Asn Pro Gln Ile Cys Gly tgaagacgct gatgctccag gaccctctga accacgacgt

TABLE 32

DNA Sequence (SEQ ID NO:88) and Protein Sequence (SEQ ID NO:89) of EIA atg ttc acc gtg ttt ctg ttg gtt gtc ttg gca acc act gtc ggt tcc
Met Phe Thr Val Phe Leu Leu Val Val Leu Ala Thr Thr Val Gly Ser ttc act tta gat cgt gca tct gat ggt agg gat gcc gca gcc aac gac
Phe Thr Leu Asp Arg Ala Ser Asp Gly Arg Asp Ala Ala Ala Asn Asp aaa gcg tct gac ctg atc gct ctg acc gcc agg aga gat cca tgc tgt
Lys Ala Ser Asp Leu Ile Ala Leu Thr Ala Arg Arg Asp Pro Cys Cys tcc aat cct gcc tgt aac gtg aat aat cca cag att tgt ggt
Ser Asn Pro Ala Cys Asn Val Asn Asn Pro Gln Ile Cys Gly tgaagacgct gatgctccag gaccctctga accacgacgt

TABLE 33

DNA Sequence (SEQ ID NO:90) and Protein Sequence (SEQ ID NO:91) of P1.2 atg ttc acc gtg ttt ctg ttg gtg gat gcc gca gcc aac gac aag gcg
Met Phe Thr Val Phe Leu Leu Val Asp Ala Ala Ala Asn Asp Lys Ala tct gac cgg atc gct ctg acc gcc agg aga gat cca tgc tgt tcc aat
Ser Asp Arg Ile Ala Leu Thr Ala Arg Arg Asp Pro Cys Cys Ser Asn cct gtc tgt acc gtg cat aat cca cag att tgt ggt tgaagacgct
Pro Val Cys Thr Val His Asn Pro Gln Ile Cys Gly

TABLE 33-continued

DNA Sequence (SEQ ID NO:90) and Protein Sequence (SEQ ID NO:91) of P1.2

Pro Val Cys Thr Val His Asn Pro Gln Ile Cys Gly gatgctccag gaccctctga accacgacgt

TABLE 34

DNA Sequence (SEQ ID NO:92) and Protein Sequence (SEQ ID NO:93) of P1.3

```
atg ttc acc gtg ttt ctg ttg gtt gtc ttg gta acc acc gtc gtt tcc
Met Phe Thr Val Phe Leu Leu Val Val Leu Val Thr Thr Val Val Ser ttc aat tca gat cgt gca tta ggt ggc agg aat gct gca gcc aaa gcg
Phe Asn Ser Asp Arg Ala Leu Gly Gly Arg Asn Ala Ala Ala Lys Ala tct gac aag atc gct tcg atc ctc ggg aga aga gca tgc tgt tct tat
Ser Asp Lys Ile Ala Ser Ile Leu Gly Arg Arg Ala Cys Cys Ser Tyr cct ccc tgt aac gtg aac tat cca gaa att tgt ggt gga cga ggc
Pro Pro Cys Asn Val Asn Tyr Pro Glu Ile Cys Gly Gly Arg Gly tgatgctcca ggaccctctg aaccacgacg t
```

TABLE 35

DNA Sequence (SEQ ID NO:94) and Protein Sequence (SEQ ID NO:95) of S11.4

```
atg ttc acc gtg ttt ctg ttg gtt gtc ttg gca acc acc gtc gtt ccc
Met Phe Thr Val Phe Leu Leu Val Val Leu Ala Thr Thr Val Val Pro ttc aat tca gat cgt gat cca gca tta ggt ggc agg aat gct gca gcc
Phe Asn Ser Asp Arg Asp Pro Ala Leu Gly Gly Arg Asn Ala Ala Ala ata gcg tct gac aag atc gct tcg acc ctc agg aga gga gga tgc tgt
Ile Ala Ser Asp Lys Ile Ala Ser Thr Leu Arg Arg Gly Gly Cys Cys tct tat cct ccc tgt aac gtg tcc tat cca gaa att tgt ggt gga cga
Ser Tyr Pro Pro Cys Asn Val Ser Tyr Pro Glu Ile Cys Gly Gly Arg cgc tgatgctcca ggaccctctg aaccacgacg t
Arg
```

TABLE 36

DNA Sequence (SEQ ID NO:96) and Protein Sequence (SEQ ID NO:97) of S11.4A

```
atg ttc acc gtg ttt ctg ttg gtt gtc ttg gca acc acc gtc gtt tcc
Met Phe Thr Val Phe Leu Leu Val Val Leu Ala Thr Thr Val Val Ser ttc aat tca gat cgt gca tta ggt ggc agg aat gct gca gcc aaa gcg
Phe Asn Ser Asp Arg Ala Leu Gly Gly Arg Asn Ala Ala Ala Lys Ala tct gac aag atc gct tcg atc ctc ggg aga aga aga tgc tgt tct tat
Ser Asp Lys Ile Ala Ser Ile Leu Gly Arg Arg Arg Cys Cys Ser Tyr cct ccc tgt aac gtg tcc tat cca gaa att tgt ggt gga cga cgc
Pro Pro Cys Asn Val Ser Tyr Pro Glu Ile Cys Gly Gly Arg Arg tgatgctcca ggaccctctg aaccacgacg t
```

TABLE 37

DNA Sequence (SEQ ID NO:98) and Protein Sequence (SEQ ID NO:99) of S11.8

```
atg ttc acc gtg ttt ctg ttg gtt gtc ttg gca acc acc gtc gtt tcc
Met Phe Thr Val Phe Leu Leu Val Val Leu Ala Thr Thr Val Val Ser ttc aat tca gat cgt gca tta ggt ggc agg aat gct gca gcc aaa gcg
Phe Asn Ser Asp Arg Ala Leu Gly Gly Arg Asn Ala Ala Ala Lys Ala tct gac aag atc gct tcg atc ctc ggg aga aga gca tgc tgt tct tat
Ser Asp Lys Ile Ala Ser Ile Leu Gly Arg Arg Ala Cys Cys Ser Tyr cct ccc tgt aac gtg aac tat cca gaa att tgt ggt gga cga ggc
Pro Pro Cys Aso Val Asn Tyr Pro Glu Ile Cys Gly Gly Arg Gly tgatgctcca ggaccctctg aaccacgacg t
```

TABLE 38

DNA Sequence (SEQ ID NO:100) and Protein Sequence (SEQ ID NO:101) of P1.1

```
atg ttc acc gtg ttt ctg ttg gtt gtc ttg gca acc act gtc ggt tcc
Met Phe Thr Val Phe Leu Leu Val Val Leu Ala Thr Thr Val Gly Ser ttc act tta gat cgt gca tct gat ggt agg gat gcc gca gcc aac gac
Phe Thr Leu Asp Arg Ala Ser Asp Gly Arg Asp Ala Ala Ala Asn Asp aaa gcg act gac ctg atc gct ctg acc gcc agg aga gat aca tgc tgt
Lys Ala Thr Asp Leu Ile Ala Leu Thr Ala Arg Arg Asp Pro Cys Cys tcc aat cct gtc tgt acc gtg cat aat cca cag att tgt ggt
Ser Asn Pro Val Cys Thr Val His Asn Pro Gln Ile Cys Gly tgaagacgct gatgcttcag gaccctctga accacgacgt
```

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

BIBLIOGRAPHY

Bamay, G. et al. (2000). *J. Med. Chem.*
Bitan, G. et al. (1997). *J. Peptide Res.* 49:421–426.
Blount, K. et al. (1992). *Toxicon* 30:835–842.
Bodansky et al. (1966). *Chem. Ind.* 38:1597–98.
Craik, D. J. et al. (1991). *Toxicon* 39:43–60.
Cruz, L. J. et al. (1987). *J. Biol. Chem.* 260:9280–9288.
Goodman and Gilman's *The Pharmacological Basis of Therapeutics*, 7th Ed., Section II (1985).
Gray, W. R. et al. (1981). *J. Biol. Chem.* 256:4734–4740.
Haack, J. A. et al. (1990). *J. Biol. Chem.* 265:6025–6029.
Horiki, K. et al. (1978). *Chemistry Letters* 165–68.
Hubry, V. et al. (1994). *Reactive Polymers* 22:231–241.
Kapoor (1970). *J. Pharm. Sci.* 59:1–27.
Kornreich, W. D. et al. (1986). U.S. Pat. No. 4,569,967.
Marshall, I. G. and Harvey, A. L. (1990). *Toxicon* 28:231–234.
McIntosh, J. M. et al. (1982). *Arch. Biochem. Biophys.* 218:329–334.
Mena, E. E. et al. (1990). *Neurosci. Lett.* 118:241–244.
*Methoden der Organischen Chemie (Houben-Weyl): Synthese von Peptiden*, E. Wunsch (Ed.), Georg Thieme Verlag, Stuttgart, Ger. (1974).
Myers, R. A. et al. (1991). *Biochemistry* 30:9370–9377.
Nishiuchi, Y. et al. (1993). *Int. J. Pept. Protein Res.* 42:533–538.
Nowak, L. et al. (1984). *Nature* 307:462–465.
Olivera, B. M. et al. (1984). U.S. Pat. No. 4,447,356.
Olivera, B. M. et al. (1985). *Science* 230:1338–1343.
Olivera, B. M. et al. (1996). U.S. Pat. No. 5,514,774.
Ornstein, et al. (1993). *Biorganic Medicinal Chemistry Letters* 3:43–48.
*Physicians' Desk Reference*, 48th Ed., pp. 689,758,1362, 1648 (1994).
Rivier, J. R. et al. (1978). *Biopolymers* 17:1927–38.
Rivier, J. R. et al. (1987). *Biochem.* 26:8508–8512.
Sambrook, J. et al. (1989). *Molecular Cloning: A Laboratory Manual*, 2nd Ed., Cold Spring Harbor Laboratory, Cold Spring Harbor, N.Y.
Schroder & Lubke (1965). *The Peptides* 1:72–75, Academic Press, NY.
Stewart and Young, *Solid-Phase Peptide Synthesis*, Freeman & Co., San Francisco, Calif. (1969).
Vale et al. (1978). U.S. Pat. No. 4,105,603.
Van de Steen, P. et al. (1998). *Critical Rev. in Biochem. and Mol. Biol.* 33:151–208.
Zafaralla, G. C. et al. (1988). *Biochemistry* 27:7102–7105.
Zhou L. M., et al. (1996). *J. Neurochem.* 66:620–628.
U.S. Pat. No. 3,972,859.
U.S. Pat. No. 3,842,067.
U.S. Pat. No. 3,862,925.
U.S. Pat. No. 4,190,674.
U.S. Pat. No. 4,179,507.
U.S. Pat. No. 4,508,715.
U.S. Pat. No. 4,701,460.
U.S. Pat. No. 4,761,418.
U.S. Pat. No. 4,923,898.
U.S. Pat. No. 5,015,741.
U.S. Pat. No. 5,260,337.

What is claimed is:

1. A substantially pure α-conotoxin peptide analog selected from the group consisting of:

MI[K10Q]: Gly-Arg-Cys-Cys-His-Pro-Ala-Cys-Gly-Gln-Asn-Tyr-Ser-Cys (SEQ ID NO:102);

MI[K10E]: Gly-Arg-Cys-Cys-His-Pro-Ala-Cys-Gly-Glu-Asn-Tyr-Ser-Cys (SEQ ID NO:103);

MI[K10Q, N11Q]: Gly-Arg-Cys-Cys-His-Pro-Ala-Cys-Gly-Gln-Gln-Tyr-Ser-Cys (SEQ ID NO:104);

MI[H5N, K10Q]: Gly-Arg-Cys-Cys-Asn-Pro-Ala-Cys-Gly-Gln-Asn-Tyr-Ser-Cys (SEQ ID NO:105);

MI[K10N]: Gly-Arg-Cys-Cys-His-Pro-Ala-Cys-Gly-Asn-Asn-Tyr-Ser-Cys (SEQ ID NO:106);

desG1-MI[K10Q, N11Q]: Arg-Cys-Cys-His-Pro-Ala-Cys-Gly-Gln-Gln-Tyr-Ser-Cys (SEQ ID NO:107);

MI[K10Q, S13D]: Gly-Arg-Cys-Cys-His-Pro-Ala-Cys-Gly-Gln-Asn-Tyr-Asp-Cys (SEQ ID NO:108);

MI[K10homoSer]: Gly-Arg-Cys-Cys-His-Pro-Ala-Cys-Gly-Xaa-Asn-Tyr-Ser-Cys (SEQ ID NO:109), where Xaa is homoserine;

desG1-MI[R2E, K10Q]: Glu-Cys-Cys-His-Pro-Ala-Cys-Gly-Gln-Asn-Tyr-Ser-Cys (SEQ ID NO: 110);

desG1/E2-MI[K10Q]: Cys-Cys-His-Pro-Ala-Cys-Gly-Gln-Asn-Tyr-Ser-Cys (SEQ ID NO:111);

MI[K10Q, Y12F]: Gly-Arg-Cys-Cys-His-Pro-Ala-Cys-Gly-Gln-Asn-Phe-Ser-Cys (SEQ ID NO:112);

MI[K10Q, S13K]: Gly-Arg-Cys-Cys-His-Pro-Ala-Cys-Gly-Gln-Asn-Tyr-Lys-Cys (SEQ ID NO:113);

MI[R2E, K10Q]: Gly-Glu-Cys-Cys-His-Pro-Ala-Cys-Gly-Gln-Asn-Tyr-Ser-Cys (SEQ ID NO:114);

MI[C4E, K10Q, C14K]: Gly-Arg-Cys-Glu-His-Pro-Ala-Cys-Gly-Gln-Asn-Tyr-Ser-Lys (SEQ ID NO:115), wherein Glu4 and Lys14 form a lactam bridge in place of the disulfide bridge in the native MI;

MI[C4E, K10N, C14K]: Gly-Arg-Cys-Glu-His-Pro-Ala-Cys-Gly-Asn-Asn-Tyr-Ser-Lys (SEQ ID NO:116), wherein Glu4 and Lys14 form a lactam bridge in place of the disulfide bridge in the native MI;

MI[C4D, K10Q, C 14K]: Gly-Arg-Cys-Asp-His-Pro-Ala-Cys-Gly-Gln-Asn-Tyr-Ser-Lys (SEQ ID NO:117), wherein Asp4 and Lys14 form a lactam bridge in place of the disulfide bridge in the native MI;

MI[C4D, K10N, C14K]: Gly-Arg-Cys-Asp-His-Pro-Ala-Cys-Gly-Asn-Asn-Tyr-Ser-Lys (SEQ ID NO:118), wherein Asp4 and Lys14 form a lactam bridge in place of the disulfide bridge in the native MI;

GI[R9Q]: Glu-Cys-Cys-Asn-Pro-Ala-Cys-Gly-Gln-His-Tyr-Ser-Cys (SEQ ID NO:119);

GI[R9N]: Glu-Cys-Cys-Asn-Pro-Ala-Cys-Gly-Asn-His-Tyr-Ser-Cys (SEQ ID NO:120);

GI[C3E, C 13K]: Glu-Cys-Glu-Asn-Pro-Ala-Cys-Gly-Arg-His-Tyr-Ser-Lys (SEQ ID NO:121), wherein Glu3 and Lys13 form a lactam bridge in place of the disulfide bridge in the native GI;

GI[C3E, R9Q, C13K]: Glu-Cys-Glu-Asn-Pro-Ala-Cys-Gly-Gln-His-Tyr-Ser-Lys (SEQ ID NO:122), wherein Glu3 and Lys13 form a lactam bridge in place of the disulfide bridge in the native GI;

GI[C3E, R9N, Cl 3K]: Glu-Cys-Glu-Asn-Pro-Ala-Cys-Gly-Asn-His-Tyr-Ser-Lys (SEQ ID NO:123), wherein Glu3 and Lys13 form a lactam bridge in place of the disulfide bridge in the native GI;

GI[C3D, R9Q, C13K]: Glu-Cys-Asp-Asn-Pro-Ala-Cys-Gly-Gln-His-Tyr-Ser-Lys (SEQ ID NO:124), wherein Asp3 and Lys13 form a lactam bridge in place of the disulfide bridge in the native GI; and GI[C3D, R9N, C13K]: Glu-Cys-Asp-Asn-Pro-Ala-Cys-Gly-Asn-His-Tyr-Ser-Lys (SEQ ID NO:125), wherein Asp3 and Lys13 form a lactam bridge in place of the disulfide bridge in the native GI.

2. A method for providing musculoskeletal relaxation in a patient undergoing a surgical procedure requiring anesthesia which comprises administering an effective amount of an α-conotoxin peptide analog or a pharmaceutically acceptable salt thereof, said α-conotoxin peptide analog selected from the group consisting of:

MI[K10Q]: Gly-Arg-Cys-Cys-His-Pro-Ala-Cys-Gly-Gln-Asn-Tyr-Ser-Cys (SEQ ID NO:102);

MI[K10E]: Gly-Arg-Cys-Cys-His-Pro-Ala-Cys-Gly-Glu-Asn-Tyr-Ser-Cys (SEQ ID NO:103);

MI[K10Q, N11Q]: Gly-Arg-Cys-Cys-His-Pro-Ala-Cys-Gly-Gln-Gln-Tyr-Ser-Cys (SEQ ID NO:104);

MI[H5N, K10Q]: Gly-Arg-Cys-Cys-Asn-Pro-Ala-Cys-Gly-Gln-Asn-Tyr-Ser-Cys (SEQ ID NO:105);

MI[K10N]: Gly-Arg-Cys-Cys-His-Pro-Ala-Cys-Gly-Asn-Asn-Tyr-Ser-Cys (SEQ ID NO:106);

desG1-MI[K10Q, N11Q]: Arg-Cys-Cys-His-Pro-Ala-Cys-Gly-Gln-Gln-Tyr-Ser-Cys (SEQ ID NO:107);

MI[K10Q, S 13D]: Gly-Arg-Cys-Cys-His-Pro-Ala-Cys-Gly-Gln-Asn-Tyr-Asp-Cys (SEQ ID NO:108);

MI[K10homoSer]: Gly-Arg-Cys-Cys-His-Pro-Ala-Cys-Gly-Xaa-Asn-Tyr-Ser-Cys (SEQ ID NO:109), where Xaa is homoserine;

desG1-MI[R2E, K10Q]: Glu-Cys-Cys-His-Pro-Ala-Cys-Gly-Gln-Asn-Tyr-Ser-Cys (SEQ ID NO:110);

desG1/R2-MI[K10Q]: Cys-Cys-His-Pro-Ala-Cys-Gly-Gln-Asn-Tyr-Ser-Cys (SEQ ID NO:111);

MI[K10Q, Y12F]: Gly-Arg-Cys-Cys-His-Pro-Ala-Cys-Gly-Gln-Asn-Phe-Ser-Cys (SEQ ID NO:112);

MI[K10Q, S13K]: Gly-Arg-Cys-Cys-His-Pro-Ala-Cys-Gly-Gln-Asn-Tyr-Lys-Cys (SEQ ID NO:113);

MI[R2E, K10Q]; Gly-Glu-Cys-Cys-His-Pro-Ala-Cys-Gly-Gln-Asn-Tyr-Ser-Cys (SEQ ID NO:114);

MI[C4E, K10Q, C14K]: Gly-Arg-Cys-Glu-His-Pro-Ala-Cys-Gly-Gln-Asn-Tyr-Ser-Lys (SEQ ID NO:115), wherein Glu4 and Lys14 form a lactam bridge in place of the disulfide bridge in the native MI;

MI[C4E, K10N, C14K]: Gly-Arg-Cys-Glu-His-Pro-Ala-Cys-Gly-Asn-Asn-Tyr-Ser-Lys (SEQ ID NO:116), wherein Glu4 and Lys14 form a lactam bridge in place of the disulfide bridge in the native MI;

MI[C4D, K10Q, C14K]: Gly-Arg-Cys-Asp-His-Pro-Ala-Cys-Gly-Gln-Asn-Tyr-Ser-Lys (SEQ ID NO:117), wherein Asp4 and Lys14 form a lactam bridge in place of the disulfide bridge in the native MI;

MI[C4D, K10N, C14K]: Gly-Arg-Cys-Asp-His-Pro-Ala-Cys-Gly-Asn-Asn-Tyr-Ser-Lys (SEQ ID NO:118), wherein Asp4 and Lys14 form a lactam bridge in place of the disulfide bridge in the native MI;

GI[R9Q]: Glu-Cys-Cys-Asn-Pro-Ala-Cys-Gly-Gln-His-Tyr-Ser-Cys (SEQ ID NO:119);

GI[R9N]: Glu-Cys-Cys-Asn-Pro-Ala-Cys-Gly-Asn-His-Tyr-Ser-Cys (SEQ ID NO:120);

GI[C3E, C13K]: Glu-Cys-Glu-Asn-Pro-Ala-Cys-Gly-Arg-His-Tyr-Ser-Lys (SEQ ID NO: 121), wherein Glu3 and Lys13 form a lactam bridge in place of the disulfide bridge in the native GI;

GI[C3E, R9Q, C13K]: Glu-Cys-Glu-Asn-Pro-Ala-Cys-Gly-Gln-His-Tyr-Ser-Lys (SEQ ID NO:122), wherein Glu3 and Lys13 form a lactam bridge in place of the disulfide bridge in the native GI;

GI[C3E, R9N, C13K]: Glu-Cys-Glu-Asn-Pro-Ala-Cys-Gly-Asn-His-Tyr-Ser-Lys (SEQ ID NO:123), wherein Glu3 and Lys13 form a lactam bridge in place of the disulfide bridge in the native GI;

GI[C3D, R9Q, C13K]: Glu-Cys-Asp-Asn-Pro-Ala-Cys-Gly-Gln-His-Tyr-Ser-Lys (SEQ ID NO:124), wherein Asp3 and Lys13 form a lactam bridge in place of the disulfide bridge in the native GI; and GI[C3D, R9N, C13K]: Glu-Cys-Asp-Asn-Pro-Ala-Cys-Gly-Asn-His-Tyr-Ser-Lys (SEQ ID NO:125), wherein Asp3 and Lys13 form a lactam bridge in place of the disulfide bridge in the native GI.

3. A method for providing musculoskeletal relaxation in a patient undergoing a surgical procedure requiring anesthesia which comprises administering an effective amount of an α-conotoxin peptide analog or a pharmaceutically acceptable salt thereof, said α-conotoxin peptide analog comprising the substitution of Gln for Lys at amino acid position 10 of α-conotoxin MI and said α-conotoxin analog selected from the group consisting of:

MI[K10Q]: Gly-Arg-Cys-Cys-His-Pro-Ala-Cys-Gly-Gln-Asn-Tyr-Ser-Cys (SEQ ID NO:102);

MI[K10Q, N11Q]: Gly-Arg-Cys-Cys-His-Pro-Ala-Cys-Gly-Gln-Gln-Tyr-Ser-Cys (SEQ ID NO:104);

MI[H5N, K10Q]: Gly-Arg-Cys-Cys-Asn-Pro-Ala-Cys-Gly-Gln-Asn-Tyr-Ser-Cys (SEQ ID NO:105);

desG1-MI[K10Q, N11Q]: Arg-Cys-Cys-His-Pro-Ala-Cys-Gly-Gln-Gln-Tyr-Ser-Cys (SEQ ID NO:107);

MI[K10Q, S13D]: Gly-Arg-Cys-Cys-His-Pro-Ala-Cys-Gly-Gln-Asn-Tyr-Asp-Cys (SEQ ID NO:108);

desG1-MI[R2E, K10Q]: Glu-Cys-Cys-His-Pro-Ala-Cys-Gly-Gln-Asn-Tyr-Ser-Cys (SEQ ID NO:110);

desG1/R2-MI[K10Q]: Cys-Cys-His-Pro-Ala-Cys-Gly-Gln-ASN-Ser-Cys (SEQ ID NO:111);

MI[K10Q, Y12F]: Gly-Arg-Cys-Cys-His-Pro-Ala-Cys-Gly-Gln-Asn-Phe-Ser-Cys (SEQ ID NO:112);

MI[K10Q, S13K]: Gly-Arg-Cys-Cys-His-Pro-Ala-Cys-Gly-Gln-Asn-Tyr-Lys-Cys (SEQ ID NO:113);

MI[R2E, K10Q]: Gly-Glu-Cys-Cys-His-Pro-Ala-Cys-Gly-Gln-Asn-Tyr-Ser-Cys (SEQ ID NO:114);

MI[C4E, K10Q, C14K]: Gly-Arg-Cys-Glu-His-Pro-Ala-Cys-Gly-Gln-Asn-Tyr-Ser-Lys (SEQ ID NO:115), wherein Glu4 and Lys14 form a lactam bridge in place of the disulfide bridge in the native MI; and MI[C4D, K10Q, C14K]: Gly-Arg-Cys-Asp-His-Pro-Ala-Cys-Gly-Gln-Asn-Tyr-Ser-Lys (SEQ ID NO:117), wherein Asp4 and Lys14 form a lactam bridge in place of the disulfide bridge in the native MI.

4. The method of claim 3, wherein said α-conotoxin analog comprises MI[K10Q]: Gly-Arg-Cys-Cys-His-Pro-Ala-Cys-Gly-Gln-Asn-Tyr-Ser-Cys (SEQ ID NO:102).

* * * * *

SEQUENCE LISTING

<160> NUMBER OF SEQ ID NOS: 125

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence:generic
      sequence I for alpha-conotoxins
<221> NAME/KEY: PEPTIDE
<222> LOCATION: (1)..(2)
<223> OTHER INFORMATION: Xaa at residue 1 may be des-Xaa or Gly; Xaa at
      residue 2 is des-Xaa,Asn, Arg, Asp, Ser, Thr, Lys,
      ornithine, homoargine, N-methy-Lys,
      N,N-dimethyl-Lys, N,N,N-trimethyl-Lys or any
<221> NAME/KEY: PEPTIDE
<222> LOCATION: (2)..(4)
<223> OTHER INFORMATION: unnatural basic amino acid; Xaa at residue 3 is
      des-Xaa, Gly, Glu or gama-carboxy-Glu; Xaa at
      residue 4 is des-Xaa, Glu, Gla, Gln, pyro-Glu,
      Arg, Ile Tyr,
<221> NAME/KEY: PEPTIDE
<222> LOCATION: (4)
<223> OTHER INFORMATION: mono-halo-Tyr, di-halo-Tyr, O-sulpho-Tyr,
      O-phospho-Tyr, nitro-Tyr, Cys, His, halo-His, any
      unnatural hydroxy containing amino acid, Lys,
<221> NAME/KEY: PEPTIDE
<222> LOCATION: (4)..(7)
<223> OTHER INFORMATION: ornithine, homoargine, N-methy-Lys,
      N,N-dimethyl-Lys, N,N,N-trimethyl-Lys or any
      unnatural basic amino acid; Xaa at residue 7 is
      His, Asn or halo-His
<221> NAME/KEY: PEPTIDE
<222> LOCATION: (8)..(12)
<223> OTHER INFORMATION: Xaa at residue 8 is Pro or hydroxy-Pro; Xaa at
      residue 9 is Ala, Gly, Ser or Thr; Xaa at residue
      11 is Gly or Arg; Xaa at residue 12 is Arg, Lys,
      Pro, hydroxy-Pro, Gly, Gln, ornithine, homoargine,
<221> NAME/KEY: PEPTIDE
<222> LOCATION: (12)..(13)
<223> OTHER INFORMATION: N-methy-Lys, N,N-dimethyl-Lys,
      N,N,N-trimethyl-Lys or any unnatural basic amino acid; Xaa at
      residue 13 is His, halo-His, Asn, Lys, Tyr, mono-halo-Tyr,
      di-halo-Tyr,
<221> NAME/KEY: PEPTIDE
<222> LOCATION: (13)
<223> OTHER INFORMATION: O-sulpho-Tyr, O-phospho-Tyr, nitro-Tyr,
      N-methy-Lys, N,N-dimethyl-Lys,
      N,N,N-trimethyl-Lys, Arg, homoarginine, ornithine
      or any unnatural basic amino acid (such as
<221> NAME/KEY: PEPTIDE
<222> LOCATION: (13)..(14)
<223> OTHER INFORMATION: N-1-(2-pyrazolinyl)-Arg); Xaa at residue 14 is
      Tyr, Trp (D or L), halo-Trp, neo-Trp, Phe,
      mono-halo-Tyr, di-halo-Tyr, O-sulpho-Tyr,
      O-phospho-Tyr, nitro-Tyr, any
<221> NAME/KEY: PEPTIDE
<222> LOCATION: (14)
<223> OTHER INFORMATION: unnatural hydroxy containing amino acid (such
      as 4-hydroxymethyl-Phe, 4-hydroxyphenyl-Gly,
      2,6-dimethyl-Tyr and 5-amino-Tyr) or any unnatural
      aromatic amino acid (such as
<221> NAME/KEY: PEPTIDE
<222> LOCATION: (14)..(15)
<223> OTHER INFORMATION: nitro-Phe, 4-substituted-Phe wherein the
      substituent is C1-C3 alkyl, carboxyl,
      hyrdroxymethyl, sulphomethyl, halo, phenyl, -CHO,
      -CN, -SO3H and -NHAc; Xaa at residue 15 is Ile,
<221> NAME/KEY: PEPTIDE
<222> LOCATION: (15)..(16)
<223> OTHER INFORMATION: Ser, Thr, Asp, Gly, Asn, Glu, gamma-carboxy-Glu
      or Val; Xaa at residue 16 is des-Xaa, Lys, Arg,
      ornithine, homoargine, N-methy-Lys,
      N,N-dimethyl-Lys, N,N,N-trimethyl-Lys or any

```
<221> NAME/KEY: PEPTIDE
<222> LOCATION: (16)..(18)
<223> OTHER INFORMATION: unnatural basic amino acid; Xaa at residue 18
      is des-Xaa, Gly, Lys, Arg, ornithine, homoargine,
      N-methy-Lys, N,N-dimethyl-Lys, N,N,N-trimethyl-Lys
      or any unnatural basic amino acid;
<221> NAME/KEY: PEPTIDE
<222> LOCATION: (19)..(19)
<223> OTHER INFORMATION: Xaa at residue 19 is des-Xaa, Gly, Thr, Ser,
      His, halo-His, Lys, Arg, ornithine, homoargine,
      N-methy-Lys, N,N-dimethyl-Lys, N,N,N-trimethyl-Lys
      or any unnatural basic
<221> NAME/KEY: PEPTIDE
<222> LOCATION: (19)..(23)
<223> OTHER INFORMATION: amino acid; Xaa at residue 20 is des-Xaa, Ser
      or Thr; Xaa at residue 21 is des-Xaa or Cys; Xaa at
      residue 22 is des-Xaa, Ser or Thr; Xaa at residue
      23 is Arg, Lys,
<221> NAME/KEY: PEPTIDE
<222> LOCATION: (23)..(24)
<223> OTHER INFORMATION: ornithine, homoargine, N-methy-Lys,
      N,N-dimethyl-Lys, N,N,N-trimethyl-Lys or any
      unnatural basic amino acid; Xaa at residue 24 is
      des-Xaa, Thr, Ser, Pro or
<221> NAME/KEY: PEPTIDE
<222> LOCATION: (24)..(27)
<223> OTHER INFORMATION: hydroxy-Pro; Xaa at residue 25 is des-Xaa, Leu,
      Ser or Thr; Xaa at residue 26 is des-Xaa, Glu or
      gamma-carboxy-Glu; Xaa at residue 27 id des-Xaa,
      Pro or hydroxy-Pro.
<221> NAME/KEY: PEPTIDE
<222> LOCATION: (28)
<223> OTHER INFORMATION: Xaa at residue 28 is des-Xaa, Arg, Lys,
      ornithine, homoargine, N-methy-Lys, N,N-dimethyl-Lys,
      N,N,N-trimethyl-Lys or any unnatural basic amino
      acid (such as N-1-(2-pyrazolinyl)-Arg).
<221> NAME/KEY: PEPTIDE
<222> LOCATION: (29)
<223> OTHER INFORMATION: Xaa at residue 29 is des-Xaa, Arg, Lys,
      ornithine, homoargine, N-methy-Lys, N,N-dimethyl-Lys,
      N,N,N-trimethyl-Lys or any unnatural basic amino
      acid (such as N-1-(2-pyrazolinyl)-Arg).

<400> SEQUENCE: 1

Xaa Xaa Xaa Xaa Cys Cys Xaa Xaa Xaa Cys Xaa Xaa Xaa Xaa Xaa Xaa
 1               5                  10                  15

Cys Xaa Xaa Xaa Xaa Xaa Xaa Xaa Xaa Xaa Xaa Xaa Xaa
            20                  25

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence:generic
      sequence II for alpha-conotoxins
<221> NAME/KEY: PEPTIDE
<222> LOCATION: (1)
<223> OTHER INFORMATION: Xaa at residue 1 is des-Xaa, Arg, Ser, Thr,
      Lys, ornithine, homoargine, N-methy-Lys,
      N,N-dimethyl-Lys, N,N,N-trimethyl-Lys or any
      unnatural basic amino acid
<221> NAME/KEY: PEPTIDE
<222> LOCATION: (2)
<223> OTHER INFORMATION: Xaa at residue 2 is des-Xaa, Asp, Gly, Leu,
      Arg, Lys, ornithine, homoargine, N-methy-Lys,
      N,N-dimethyl-Lys, N,N,N-trimethyl-Lys or any
      unnatural basic amino acid
<221> NAME/KEY: PEPTIDE
<222> LOCATION: (3)
<223> OTHER INFORMATION: Xaa at residue 3 is des-Xaa, Pro, hydroxy-Pro,
      Ala, Gly or Leu.
<221> NAME/KEY: PEPTIDE
<222> LOCATION: (6)
<223> OTHER INFORMATION: Xaa at residue 6 is Tyr, Ser, Thr,
      mono-halo-Tyr, di-halo-Tyr, O-sulpho-Tyr, O-phospho-Tyr,
```

```
        nitro-Tyr or any unnatural hydroxy containing
        amino acid
<221> NAME/KEY: PEPTIDE
<222> LOCATION: (7)..(7)
<223> OTHER INFORMATION: Xaa at residue 7 is His, Asn, Ile, Tyr,
        halo-His, mono-halo-Tyr, di-halo-Tyr, O-sulpho-Tyr,
        O-phospho-Tyr or nitro-Tyr.
<221> NAME/KEY: PEPTIDE
<222> LOCATION: (8)..(11)
<223> OTHER INFORMATION: Xaa at residue 8 is Pro or hydroxy-Pro; Xaa at
        residue 9 is Thr, Ala, Val, Ser, Pro or
        hydroxy-Pro; Xaa at residue 11 is Asn, Thr, Ser,
        Lys, Arg, ornithine, homoarginine, N-methyl-Lys,
<221> NAME/KEY: PEPTIDE
<222> LOCATION: (11)..(12)
<223> OTHER INFORMATION: N,N-dimethyl-Lys, N,N,N-trimethyl-Lys or any
        unnatural basic amino acid; Xaa at residue 12 is
        Met, Val, Ala, Leu or Ile.
<221> NAME/KEY: PEPTIDE
<222> LOCATION: (13)..(14)
<223> OTHER INFORMATION: Xaa at residue 13 is Ser, Thr, Asn, His or
        halo-His; Xaa at residue 14 is Asn, Tyr,
        mono-halo-Tyr, di-halo-Tyr, O-sulpho-Tyr,
        O-phospho-Tyr, nitro-Tyr or any unnatural hydroxy
<221> NAME/KEY: PEPTIDE
<222> LOCATION: (14)..(15)
<223> OTHER INFORMATION: containing amino acid (such as
        4-hydroxymethyl-Phe, 4-hydroxyphenyl-Gly,
        2,6-dimethyl-Tyr and 5-amino-Tyr); Xaa at residue
        15 is Pro or hydroxy-Pro.
<221> NAME/KEY: PEPTIDE
<222> LOCATION: (16)..(20)
<223> OTHER INFORMATION: Xaa at residue 16 is Glu, gamma-carboxy-Glu,
        Gln or Asp; Xaa at residue 19 is des-Xaa or Gly; Xaa
        at residue 20 is des-Xaa or Gly.
<221> NAME/KEY: PEPTIDE
<222> LOCATION: (21)
<223> OTHER INFORMATION: Xaa at residue 21 is Arg, Lys, ornithine,
        homoarginine, N-methyl-Lys, N,N-dimethyl-Lys,
        N,N,N-trimethyl-Lys or any unnatural basic amino
        acid (such as N-1-pyrazolinyl)-Arg).

<400> SEQUENCE: 2

Xaa Xaa Xaa Cys Cys Xaa Xaa Xaa Xaa Cys Xaa Xaa Xaa Xaa Xaa
 1               5                   10                  15

Ile Cys Xaa Xaa Xaa
            20

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence:generic
        sequence for Conus radiatus R1.3
<221> NAME/KEY: PEPTIDE
<222> LOCATION: (1)..(11)
<223> OTHER INFORMATION: Xaa at residue 1 may be Glu or
        gamma-carboxy-Glu;
        Xaa at residue 5 may be Pro or hydroxy-Pro; Xaa at
        residue 11 may be Tyr,
<221> NAME/KEY: PEPTIDE
<222> LOCATION: (11)..(14)
<223> OTHER INFORMATION: mono-halo-Tyr, di-halo-Tyr, O-sulpho-Tyr,
        O-phospho-Tyr or nitro-Tyr; Xaa at residue 14 may
        be Lys, N-methyl-Lys, N,N-dimethyl-Lys or
        N,N,N-trimethyl-Lys.

<400> SEQUENCE: 3

Xaa Cys Cys Asn Xaa Ala Cys Gly Arg His Xaa Ser Cys Xaa Gly
 1               5                   10                  15

<210> SEQ ID NO 4
<211> LENGTH: 15
```

-continued

```
<212> TYPE: PRT
<213> ORGANISM: Artificial Sequence
<220> FEATURE:
<223> OTHER INFORMATION: Description of Artificial Sequence:generic
      sequence for Conus radiatus R1.4
<221> NAME/KEY: PEPTIDE
<222> LOCATION: (7)..(11)
<223> OTHER INFORMATION: Xa

```
<400> SEQUENCE: 7

Cys Cys Cys Asn Xaa Ala Cys Gly Xaa Asn Xaa Gly Cys Gly Thr Ser
1               5                   10                  15

Cys Ser Arg Xaa Ser Xaa Xaa Arg Arg
            20                  25

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence:generic
      sequence for Conus monachus MnII
<221> NAME/KEY: PEPTIDE
<222> LOCATION: (7)..(13)
<223> OTHER INFORMATION: Xaa at residue 7 may be Pro or hydroxy-Pro; Xaa
      at residue 12 may be Lys, N-methyl-Lys,
      N,N-dimethyl-Lys or N,N,N-trimethyl-Lys; Xaa at
      residue may be Tyr,
<221> NAME/KEY: PEPTIDE
<222> LOCATION: (13)..(15)
<223> OTHER INFORMATION: mono-halo-Tyr, di-halo-Tyr, O-sulpho-Tyr,
      O-phospho-Tyr or nitro-Tyr; Xaa at residue 15 may
      be Lys, N-methyl-Lys, N,N-dimethyl-Lys or
      N,N,N-trimethyl-Lys.

<400> SEQUENCE: 8

Asn Gly His Cys Cys His Xaa Ala Cys Gly Gly Xaa Xaa Val Xaa Cys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence:generic
      sequence for Conus achatinus A1.2
<221> NAME/KEY: PEPTIDE
<222> LOCATION: (7)..(13)
<223> OTHER INFORMATION: Xaa at residue 7 may be Pro or hydroxy-Pro; Xaa
      at residue 12 may be Lys, N-methyl-Lys,
      N,N-dimethyl-Lys or N,N,N-trimethyl-Lys; Xaa at
      residue 13 may be Tyr,
<221> NAME/KEY: PEPTIDE
<222> LOCATION: (13)..(15)
<223> OTHER INFORMATION: mono-halo-Tyr, di-halo-Tyr, O-sulpho-Tyr,
      O-phospho-Tyr or nitro-Tyr; Xaa at residue 15 may
      be Lys, N-methyl-Lys, N,N-dimethyl-Lys or
      N,N,N-trimethyl-Lys.

<400> SEQUENCE: 9

Asn Gly Arg Cys Cys His Xaa Ala Cys Gly Gly Xaa Xaa Val Xaa Cys
1               5                   10                  15

<210> SEQ ID NO 10
<211> LENGTH: 15
<212> TYPE: PRT
<213> ORGANISM: Conus achatinus
<220> FEATURE:
<221> NAME/KEY: PEPTIDE
<222> LOCATION: (7)..(11)
<223> OTHER INFORMATION: Xaa at residue 7 is Pro or hydroxy-Pro; Xaa at
      residue 11 is Lys, N-methyl-Lys, N,N-dimethyl-Lys
      or N,N,N-trimethyl-Lys.

<400> SEQUENCE: 10

Asn Gly Arg Cys Cys His Xaa Ala Cys Gly Xaa His Phe Ile Cys
1               5                   10                  15
```

```
<210> SEQ ID NO 11
<211> LENGTH: 15
<212> TYPE: PRT
<213> ORGANISM: Conus achatinus
<220> FEATURE:
<221> NAME/KEY: PEPTIDE
<222> LOCATION: (7)..(11)
<223> OTHER INFORMATION: Xaa at residue 7 is Pro or hydroxy-Pro; Xaa at
      residue 11 is Lys, N-methyl-Lys, N,N-dimethyl-Lys
      or N,N,N-trimethyl-Lys.

<400> SEQUENCE: 11

Asn Gly Arg Cys Cys His Xaa Ala Cys Gly Xaa His Phe Ser Cys
 1               5                  10                  15

<210> SEQ ID NO 12
<211> LENGTH: 15
<212> TYPE: PRT
<213> ORGANISM: Conus achatinus
<220> FEATURE:
<221> NAME/KEY: PEPTIDE
<222> LOCATION: (7)..(12)
<223> OTHER INFORMATION: Xaa at residue 7 is Pro or hydroxy-Pro; Xaa at
      residue 12 is Lys, N-methyl-Lys, N,N-dimethyl-Lys
      or N,N,N-trimethyl-Lys.
<221> NAME/KEY: PEPTIDE
<222> LOCATION: (13)
<223> OTHER INFORMATION: Xaa at residue 13 is Tyr, mono-halo-Tyr,
      di-halo-Tyr, O-sulpho-Tyr, O-phospho-Tyr or
      nitro-Tyr.

<400> SEQUENCE: 12

Asn Gly Arg Cys Cys His Xaa Ser Cys Gly Arg Xaa Xaa Asn Cys
 1               5                  10                  15

<210> SEQ ID NO 13
<211> LENGTH: 15
<212> TYPE: PRT
<213> ORGANISM: Conus aurisiacus
<220> FEATURE:
<221> NAME/KEY: PEPTIDE
<222> LOCATION: (7)..(12)
<223> OTHER INFORMATION: Xaa at residue 7 is Pro or hydroxy-Pro; Xaa at
      residue 12 is Lys, N-methyl-Lys, N,N-dimethyl-Lys
      or N,N,N-trimethyl-Lys.
<221> NAME/KEY: PEPTIDE
<222> LOCATION: (13)
<223> OTHER INFORMATION: Xaa at residue 13 is Tyr, mono-halo-Tyr,
      di-halo-Tyr, O-sulpho-Tyr, O-phospho-Tyr or
      nitro-Tyr.

<400> SEQUENCE: 13

Asn Gly Arg Cys Cys His Xaa Ala Cys Ala Arg Xaa Xaa Asn Cys
 1               5                  10                  15

<210> SEQ ID NO 14
<211> LENGTH: 15
<212> TYPE: PRT
<213> ORGANISM: Conus aurisiacus
<220> FEATURE:
<221> NAME/KEY: PEPTIDE
<222> LOCATION: (2)..(12)
<223> OTHER INFORMATION: Xaa at residue 2 is Glu or gamma-carboxy-Glu;
      Xaa at residue 7 is Pro or hydroxy-Pro; Xaa at residue
      12 is Lys, N-methyl-Lys, N,N-dimethyl-Lys or
      N,N,N-trimethyl-Lys.
<221> NAME/KEY: PEPTIDE
<222> LOCATION: (13)
<223> OTHER INFORMATION: Xaa at residue 13 is Tyr, mono-halo-Tyr,
      di-halo-Tyr, O-sulpho-Tyr, O-phospho-Tyr or
      nitro-Tyr

<400> SEQUENCE: 14
```

```
Asn Xaa Arg Cys Cys His Xaa Ala Cys Ala Arg Xaa Xaa Asn Cys
 1               5              10                 15
```

<210> SEQ ID NO 15
<211> LENGTH: 15
<212> TYPE: PRT
<213> ORGANISM: Conus magus
<220> FEATURE:
<221> NAME/KEY: PEPTIDE
<222> LOCATION: (7)..(13)
<223> OTHER INFORMATION: Xaa at residue 7 is Pro or hydroxy-Pro; Xaa at
      residue 13 is Tyr, mono-halo-Tyr, di-halo-Tyr,
      O-sulpho-Tyr, O-phospho-Tyr or nitro-Tyr.

<400> SEQUENCE: 15

```
Asp Gly Arg Cys Cys His Xaa Ala Cys Gly Gln Asn Xaa Ser Cys
 1               5              10                 15
```

<210> SEQ ID NO 16
<211> LENGTH: 15
<212> TYPE: PRT
<213> ORGANISM: Conus magus
<220> FEATURE:
<221> NAME/KEY: PEPTIDE
<222> LOCATION: (7)..(11)
<223> OTHER INFORMATION: Xaa at residue 7 is Pro or hydroxy-Pro; Xaa at
      residue 11 is Lys, N-methyl-Lys, N,N-dimethyl-Lys
      or N,N,N-trimethyl-Lys.

<400> SEQUENCE: 16

```
Asp Gly Arg Cys Cys His Xaa Ala Cys Ala Xaa His Phe Asn Cys
 1               5              10                 15
```

<210> SEQ ID NO 17
<211> LENGTH: 15
<212> TYPE: PRT
<213> ORGANISM: Conus magus
<220> FEATURE:
<221> NAME/KEY: PEPTIDE
<222> LOCATION: (7)..(11)
<223> OTHER INFORMATION: Xaa at residue 7 is Pro or hydroxy-Pro; Xaa at
      residue 11 is Lys, N-methyl-Lys, N,N-dimethyl-Lys
      or N,N,N-trimethyl-Lys.
<221> NAME/KEY: PEPTIDE
<222> LOCATION: (13)
<223> OTHER INFORMATION: Xaa at residue 13 is Tyr, mono-halo-Tyr,
      di-halo-Tyr, O-sulpho-Tyr, O-phospho-Tyr or
      nitro-Tyr.

<400> SEQUENCE: 17

```
Asn Gly Arg Cys Cys His Xaa Ala Cys Ala Xaa Asn Xaa Ser Cys
 1               5              10                 15
```

<210> SEQ ID NO 18
<211> LENGTH: 15
<212> TYPE: PRT
<213> ORGANISM: Conus magus
<220> FEATURE:
<221> NAME/KEY: PEPTIDE
<222> LOCATION: (7)..(12)
<223> OTHER INFORMATION: Xaa at residue 7 is Pro or hydroxy-Pro; Xaa at
      residue 12 is Lys, N-methyl-Lys, N,N-dimethyl-Lys
      or N,N,N-trimethyl-Lys
<221> NAME/KEY: PEPTIDE
<222> LOCATION: (13)
<223> OTHER INFORMATION: Xaa at residue 13 is Tyr, mono-halo-Tyr,
      di-halo-Tyr, O-sulpho-Tyr, O-phospho-Tyr or
      nitro-Tyr.

<400> SEQUENCE: 18

```
Asn Gly Arg Cys Cys His Xaa Ala Cys Ala Arg Xaa Xaa Ser Cys
 1               5                  10                  15
```

<210> SEQ ID NO 19
<211> LENGTH: 13
<212> TYPE: PRT
<213> ORGANISM: Conus obscurus
<220> FEATURE:
<221> NAME/KEY: PEPTIDE
<222> LOCATION: (1)..(10)
<223> OTHER INFORMATION: Xaa at residue 1 is Gln or pyro-Glu; Xaa at
    residues 5 and 9 is Pro or hydroxy-Pro; Xaa at
    residue 10 is Lys, N-methyl-Lys, N,N-dimethyl-Lys
    or N,N,N-trimethyl-Lys.
<221> NAME/KEY: PEPTIDE
<222> LOCATION: (11)
<223> OTHER INFORMATION: Xaa at residue 11 is Tyr, mono-halo-Tyr,
    di-halo-Tyr, O-sulpho-Tyr, O-phospho-Tyr or
    nitro-Tyr.

<400> SEQUENCE: 19

```
Xaa Cys Cys Asn Xaa Ala Cys Gly Xaa Xaa Xaa Ser Cys
 1               5                  10
```

<210> SEQ ID NO 20
<211> LENGTH: 13
<212> TYPE: PRT
<213> ORGANISM: Conus striatus
<220> FEATURE:
<221> NAME/KEY: PEPTIDE
<222> LOCATION: (1)..(10)
<223> OTHER INFORMATION: Xaa at residue 1 is Gln or pyro-Glu; Xaa at
    residue 5 is Pro or hydroxy-Pro; Xaa at residues 9
    and 10 is Lys, N-methyl-Lys, N,N-dimethyl-Lys or
    N,N,N-trimethyl-Lys.
<221> NAME/KEY: PEPTIDE
<222> LOCATION: (11)
<223> OTHER INFORMATION: Xaa at residue 11 is Tyr, mono-halo-Tyr,
    di-halo-Tyr, O-sulpho-Tyr, O-phospho-Tyr or
    nitro-Tyr.

<400> SEQUENCE: 20

```
Xaa Cys Cys His Xaa Ala Cys Gly Xaa Xaa Xaa Asn Cys
 1               5                  10
```

<210> SEQ ID NO 21
<211> LENGTH: 15
<212> TYPE: PRT
<213> ORGANISM: Conus striatus
<220> FEATURE:
<221> NAME/KEY: PEPTIDE
<222> LOCATION: (7)..(12)
<223> OTHER INFORMATION: Xaa at residue 7 is Pro or hydroxy-Pro; Xaa at
    residue 12 is Lys, N-methyl-Lys, N,N-dimethyl-Lys
    or N,N,N-trimethyl-Lys
<221> NAME/KEY: PEPTIDE
<222> LOCATION: (13)
<223> OTHER INFORMATION: Xaa at residue 13 is Tyr, mono-halo-Tyr,
    di-halo-Tyr, O-sulpho-Tyr, O-phospho-Tyr or
    nitro-Tyr.

<400> SEQUENCE: 21

```
Ser Gly Arg Cys Cys His Xaa Ala Cys Gly Arg Xaa Xaa Asn Cys
 1               5                  10                  15
```

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence:generic
    sequence for Conus purpuraxcens P1.2

-continued

```
<221> NAME/KEY: PEPTIDE
<222> LOCATION: (3)..(15)
<223> OTHER INFORMATION: Xaa at residues 3, 8 and 15 may be Pro or
      hydroxy-Pro.

<400> SEQUENCE: 22

Arg Asp Xaa Cys Cys Ser Asn Xaa Val Cys Thr Val His Asn Xaa Gln
 1               5                  10                  15

Ile Cys

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence:generic
      sequence for Conus purpurascens P1.3
<221> NAME/KEY: PEPTIDE
<222> LOCATION: (6)..(14)
<223> OTHER INFORMATION: Xaa at residues and 6 and 13 is Tyr,
      mono-halo-Tyr, di-halo-Tyr, O-sulpho-Tyr,
      O-phospho-Tyr or nitro-Tyr; Xaa at residues 7, 8
      and 14 may be Pro or hydroxy-Pro.
<221> NAME/KEY: PEPTIDE
<222> LOCATION: (15)
<223> OTHER INFORMATION: Xaa at residue 15 may be Glu or
      gamma-carboxy-Glu.

<400> SEQUENCE: 23

Arg Ala Cys Cys Ser Xaa Xaa Xaa Cys Asn Val Asn Xaa Xaa Xaa Ile
 1               5                  10                  15

Cys

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence:generic
      sequence for Conus sulcatus Sl1.4
<221> NAME/KEY: PEPTIDE
<222> LOCATION: (6)..(14)
<223> OTHER INFORMATION: Xaa at residues 6 and 13 may be Tyr,
      mono-halo-Tyr, di-halo-Tyr, O-sulpho-Tyr,
      O-phospho-Tyr or nitro-Tyr; Xaa at residues 7, 8
      and 14 may be Pro of hydroxy-Pro.
<221> NAME/KEY: PEPTIDE
<222> LOCATION: (15)
<223> OTHER INFORMATION: Xaa at residue 15 may be Glu or
      gamma-carboxy-Glu.

<400> SEQUENCE: 24

Gly Gly Cys Cys Ser Xaa Xaa Xaa Cys Asn Val Ser Xaa Xaa Xaa Ile
 1               5                  10                  15
Cys

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:generic
      sequence for Conus sulcatus Sl1.4A
<221> NAME/KEY: PEPTIDE
<222> LOCATION: (4)..(12)
<223> OTHER INFORMATION: Xaa at residues 4 and 11 may be Tyr,
      mono-halo-tyr, di-halo-Tyr, O-sulpho-Tyr,
      O-phospho-Tyr or nitro-Tyr; Xaa at residues 5, 6
      and 12 may be Pro of hydroxy-Pro.
<221> NAME/KEY: PEPTIDE
<222> LOCATION: (13)
```

```
<223> OTHER INFORMATION: Xaa at residue 13 may be Glu or
      gamma-carboxy-Glu

<400> SEQUENCE: 25

Cys Cys Ser Xaa Xaa Xaa Cys Asn Val Ser Xaa Xaa Xaa Ile Cys
 1               5                  10                  15

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence:generic
      sequence for Conus sulcatus Sl1.8
<221> NAME/KEY: PEPTIDE
<222> LOCATION: (5)..(13)
<223> OTHER INFORMATION: Xaa at residues 5 and 12 may be Tyr,
      mono-halo-Tyr, di-halo-Tyr, O-sulpho-Tyr,
      O-phospho-Tyr or nitro-Tyr; Xaa at residues 6, 7
      and 13 may be Pro or hydroxy-Pro.
<221> NAME/KEY: PEPTIDE
<222> LOCATION: (14)
<223> OTHER INFORMATION: Xaa at residue 14 may be Glu or
      gamma-carboxy-Glu.

<400> SEQUENCE: 26

Ala Cys Cys Ser Xaa Xaa Xaa Cys Asn Val Asn Xaa Xaa Xaa Ile Cys
 1               5                  10                  15

Gly Gly Arg

<210> SEQ ID NO 27
<211> LENGTH: 18
<212> TYPE: PRT
<213> ORGANISM: Conus textile
<220> FEATURE:
<221> NAME/KEY: PEPTIDE
<222> LOCATION: (8)..(15)
<223> OTHER INFORMATION: Xaa at residues 8 and 15 is Pro or hydroxy-Pro;
      Xaa at residue 11 is Lys, N-methyl-Lys,
      N,N-dimethyl-Lys or N,N,N-trimethyl-Lys
<221> NAME/KEY: PEPTIDE
<222> LOCATION: (14)
<223> OTHER INFORMATION: Xaa at residue 14 is Tyr, mono-halo-Tyr,
      di-halo-Tyr, O-sulpho-Tyr, O-phospho-Tyr or
      nitro-Tyr.

<400> SEQUENCE: 27

Ser Leu Leu Cys Cys Thr Ile Xaa Ser Cys Xaa Ala Ser Xaa Xaa Asp
 1               5                  10                  15

Ile Cys

<210> SEQ ID NO 28
<211> LENGTH: 1004
<212> TYPE: DNA
<213> ORGANISM: Conus geographus
<220> FEATURE:
<221> NAME/KEY: CDS
<222> LOCATION: (1)..(177)

<400> SEQUENCE: 28 atg ttc acc gtg ttt ctg ttg gtg gtc ttg gca acc act gtc gtt tcc        48
Met Phe Thr Val Phe Leu Leu Val Val Leu Ala Thr Thr Val Val Ser
 1               5                  10                  15 ttc cct tca gaa cgt gca tct gat ggc agg gat gac aca gcc aaa gac        96
Phe Pro Ser Glu Arg Ala Ser Asp Gly Arg Asp Asp Thr Ala Lys Asp
                20                  25                  30 gaa ggg tct gac atg gag aaa ttg gtc gag aaa aaa gaa tgt tgc aat       144
Glu Gly Ser Asp Met Glu Lys Leu Val Glu Lys Lys Glu Cys Cys Asn
```

-continued

```
                        35                  40                  45
cct gcc tgt ggc aga cac tac agt tgt gga cgc tgatgctcca ggaccctctg          197
Pro Ala Cys Gly Arg His Tyr Ser Cys Gly Arg
        50                  55 aaccacggac gtgccgccct ctgcctgacc tgcttcactg tccgtctctt tgtgccacta          257
gaactgaaca gctcgatcca ctagactacc acgttacctc cgtgttctaa aactacttgg          317
tttagattgc ctttaatttc tagtcatact tcctgttatt acgtcgtcca aaattgaaac          377
aagaacatga gggtgtcag ctcaaacaaa atcaggcaat gacaaggaaa atgtctccga           437
tcgatccgaa aactgtcacc cgtcactctc ttaaccagtt ttagaactga ttaccactag          497
agcttttgta ccacatcaaa tcaggtctat gtgtgatgtt tcttttgcaa aatttaattt         557
ttgagaaaaa aagctcaaaa tgtgggaagt gcttttgatt ttctgacaac ttgtgatcat         617
gtccgttttc agtgagtcta attgcaacct ctgtgtgatt tcttcacct gttaagcaac          677 gcaaagaggt tgtccataac caggaaagca acagacaaag aaatgcttga gaatttcagg         737
ttatagataa ggtaaggaaa aaaggagag ctatgggaaa tgatgaaaac aacagataaa          797
ataaattgaa cagtacctac ttgtttcatg gttgattttt ttttctctga ataatctctg         857
tggacactaa tggcagtctc tcctcacccc acgccattag taagcttatt ttttctttct         917
ttatccaaga tttgctgaac atatttagcc tagatataga cattgctaca tataatct          977 gacaataaac tttcatgggc accaatt                                             1004
```

<210> SEQ ID NO 29
<211> LENGTH: 59
<212> TYPE: PRT
<213> ORGANISM: Conus geographus

<400> SEQUENCE: 29

```
Met Phe Thr Val Phe Leu Leu Val Val Leu Ala Thr Thr Val Val Ser
 1               5                  10                  15

Phe Pro Ser Glu Arg Ala Ser Asp Gly Arg Asp Asp Thr Ala Lys Asp
                20                  25                  30

Glu Gly Ser Asp Met Glu Lys Leu Val Glu Lys Lys Glu Cys Cys Asn
            35                  40                  45

Pro Ala Cys Gly Arg His Tyr Ser Cys Gly Arg
        50                  55
```

<210> SEQ ID NO 30
<211> LENGTH: 201
<212> TYPE: DNA
<213> ORGANISM: Conus striatus
<220> FEATURE:
<221> NAME/KEY: CDS
<222> LOCATION: (1)..(177)

<400> SEQUENCE: 30

```
atg ttc acc gtg ttt ctg ttg gtt gtc ttg gca acc act gtc gtt tcc           48
Met Phe Thr Val Phe Leu Leu Val Val Leu Ala Thr Thr Val Val Ser
 1               5                  10                  15 ttc cct tca gat cgt gca tct gat ggc agg gat gac gaa gcc aaa gac           96
Phe Pro Ser Asp Arg Ala Ser Asp Gly Arg Asp Asp Glu Ala Lys Asp
                20                  25                  30 gaa agg tct gac atg cac gaa tcg gac cgg aaa gaa atc tgt tgc aat          144
Glu Arg Ser Asp Met His Glu Ser Asp Arg Lys Glu Ile Cys Cys Asn
            35                  40                  45 cct gcc tgt ggc cca aag tat agt tgt gga cgc tgatgctcca ggaccctctg        197
Pro Ala Cys Gly Pro Lys Tyr Ser Cys Gly Arg
        50                  55
``` aacc 201

<210> SEQ ID NO 31
<211> LENGTH: 59
<212> TYPE: PRT
<213> ORGANISM: Conus striatus

<400> SEQUENCE: 31

```
Met Phe Thr Val Phe Leu Leu Val Val Leu Ala Thr Thr Val Val Ser
 1               5                  10                  15

Phe Pro Ser Asp Arg Ala Ser Asp Gly Arg Asp Asp Glu Ala Lys Asp
            20                  25                  30

Glu Arg Ser Asp Met His Glu Ser Asp Arg Lys Glu Ile Cys Cys Asn
        35                  40                  45

Pro Ala Cys Gly Pro Lys Tyr Ser Cys Gly Arg
        50                  55
```

<210> SEQ ID NO 32
<211> LENGTH: 208
<212> TYPE: DNA
<213> ORGANISM: Conus radiatus
<220> FEATURE:
<221> NAME/KEY: CDS
<222> LOCATION: (1)..(177)

<400> SEQUENCE: 32

```
atg ttc acc gtg ttt ctg ttg gtt gtc ttg aca atc act gtc gtt tcc    48
Met Phe Thr Val Phe Leu Leu Val Val Leu Thr Ile Thr Val Val Ser
 1               5                  10                  15 ttc cct tca gat cgt gca tct gat ggc agg gat gac gaa gcc aaa gac    96
Phe Pro Ser Asp Arg Ala Ser Asp Gly Arg Asp Asp Glu Ala Lys Asp
            20                  25                  30 gaa agg tct gac atg tac aaa tcg aaa cgg aat gga cgc tgt tgc cat   144
Glu Arg Ser Asp Met Tyr Lys Ser Lys Arg Asn Gly Arg Cys Cys His
        35                  40                  45 cct gcc tgt ggc aaa cac ttt agt tgt gga cgc tgatgctcca ggaccctctg 197
Pro Ala Cys Gly Lys His Phe Ser Cys Gly Arg
        50                  55 aaccacgacg t                                                      208
```

<210> SEQ ID NO 33
<211> LENGTH: 59
<212> TYPE: PRT
<213> ORGANISM: Conus radiatus

<400> SEQUENCE: 33

```
Met Phe Thr Val Phe Leu Leu Val Val Leu Thr Ile Thr Val Val Ser
 1               5                  10                  15

Phe Pro Ser Asp Arg Ala Ser Asp Gly Arg Asp Asp Glu Ala Lys Asp
            20                  25                  30

Glu Arg Ser Asp Met Tyr Lys Ser Lys Arg Asn Gly Arg Cys Cys His
        35                  40                  45

Pro Ala Cys Gly Lys His Phe Ser Cys Gly Arg
        50                  55
```

<210> SEQ ID NO 34
<211> LENGTH: 213
<212> TYPE: DNA
<213> ORGANISM: Conus radiatus
<220> FEATURE:

-continued

```
<221> NAME/KEY: CDS
<222> LOCATION: (1)..(177)

<400> SEQUENCE: 34 atg ttc acc gtg ttt ctg ttg gtg gtc ttg gca acc act gtc gtt tcc       48
Met Phe Thr Val Phe Leu Leu Val Val Leu Ala Thr Thr Val Val Ser
 1               5                  10                  15 ttc cct tca gaa cgt gca tct gat ggc agg gat gac aca gcc aaa gac       96
Phe Pro Ser Glu Arg Ala Ser Asp Gly Arg Asp Asp Thr Ala Lys Asp
             20                  25                  30 gaa ggg tct gac atg gag aaa ttg gtc gag aaa aaa gaa tgt tgc aat      144
Glu Gly Ser Asp Met Glu Lys Leu Val Glu Lys Lys Glu Cys Cys Asn
         35                  40                  45 cct gcc tgt ggc aga cac tac agt tgt aag gga ggacgctgat gctccagacc    197
Pro Ala Cys Gly Arg His Tyr Ser Cys Lys Gly
     50                  55 ctctgaacca cgacgt                                                    213

<210> SEQ ID NO 35
<211> LENGTH: 59
<212> TYPE: PRT
<213> ORGANISM: Conus radiatus

<400> SEQUENCE: 35

Met Phe Thr Val Phe Leu Leu Val Val Leu Ala Thr Thr Val Val Ser
 1               5                  10                  15

Phe Pro Ser Glu Arg Ala Ser Asp Gly Arg Asp Asp Thr Ala Lys Asp
             20                  25                  30

Glu Gly Ser Asp Met Glu Lys Leu Val Glu Lys Lys Glu Cys Cys Asn
         35                  40                  45

Pro Ala Cys Gly Arg His Tyr Ser Cys Lys Gly
     50                  55

<210> SEQ ID NO 36
<211> LENGTH: 208
<212> TYPE: DNA
<213> ORGANISM: Conus radiatus
<220> FEATURE:
<221> NAME/KEY: CDS
<222> LOCATION: (1)..(177)

<400> SEQUENCE: 36 atg ttc acc gtg ttt ctg ttg gtt gtc ttg aca atc act gtc gtt tcc       48
Met Phe Thr Val Phe Leu Leu Val Val Leu Thr Ile Thr Val Val Ser
 1               5                  10                  15 ttc cct tca gat cgt gca tct gat ggc agg gat gac gaa gcc aaa gac       96
Phe Pro Ser Asp Arg Ala Ser Asp Gly Arg Asp Asp Glu Ala Lys Asp
             20                  25                  30 gaa agg tct gac atg tac aaa tcg aaa cgg aat gga cgc tgt tgc cat      144
Glu Arg Ser Asp Met Tyr Lys Ser Lys Arg Asn Gly Arg Cys Cys His
         35                  40                  45 cct gcc tgt ggc aaa cac ttt agt tgt gga cgc tgatgctcca ggaccctctg   197
Pro Ala Cys Gly Lys His Phe Ser Cys Gly Arg
     50                  55 aaccacgacg t                                                         208

<210> SEQ ID NO 37
<211> LENGTH: 59
<212> TYPE: PRT
<213> ORGANISM: Conus radiatus

<400> SEQUENCE: 37
```

```
Met Phe Thr Val Phe Leu Leu Val Val Leu Thr Ile Thr Val Val Ser
 1               5                  10                  15

Phe Pro Ser Asp Arg Ala Ser Asp Gly Arg Asp Asp Glu Ala Lys Asp
                20                  25                  30

Glu Arg Ser Asp Met Tyr Lys Ser Lys Arg Asn Gly Arg Cys Cys His
            35                  40                  45

Pro Ala Cys Gly Lys His Phe Ser Cys Gly Arg
            50                  55

<210> SEQ ID NO 38
<211> LENGTH: 214
<212> TYPE: DNA
<213> ORGANISM: Conus stercusmuscarum
<220> FEATURE:
<221> NAME/KEY: CDS
<222> LOCATION: (1)..(177)

<400> SEQUENCE: 38 atg ttc acc gtg ttt ctg ttg gtt gtc ttg gca acc act gtc gtt tcc    48
Met Phe Thr Val Phe Leu Leu Val Val Leu Ala Thr Thr Val Val Ser
 1               5                  10                  15 ttc cct tca gat cgt gca tct gat ggc agg gat gac gaa gcc aaa gac    96
Phe Pro Ser Asp Arg Ala Ser Asp Gly Arg Asp Asp Glu Ala Lys Asp
                20                  25                  30 gaa agg tct gac atg cac gaa tcg ggc cgg aaa gga cgc gga cgc tgt   144
Glu Arg Ser Asp Met His Glu Ser Gly Arg Lys Gly Arg Gly Arg Cys
            35                  40                  45 tgc cat cct gcc tgt ggc cca aac tat agt tgt ggacgctgat gctccaggac  197
Cys His Pro Ala Cys Gly Pro Asn Tyr Ser Cys
        50                  55 cctctgaacc acgacgt                                                 214

<210> SEQ ID NO 39
<211> LENGTH: 59
<212> TYPE: PRT
<213> ORGANISM: Conus stercusmuscarum

<400> SEQUENCE: 39

Met Phe Thr Val Phe Leu Leu Val Val Leu Ala Thr Thr Val Val Ser
 1               5                  10                  15

Phe Pro Ser Asp Arg Ala Ser Asp Gly Arg Asp Asp Glu Ala Lys Asp
                20                  25                  30

Glu Arg Ser Asp Met His Glu Ser Gly Arg Lys Gly Arg Gly Arg Cys
            35                  40                  45

Cys His Pro Ala Cys Gly Pro Asn Tyr Ser Cys
        50                  55

<210> SEQ ID NO 40
<211> LENGTH: 221
<212> TYPE: DNA
<213> ORGANISM: Conus striatus
<220> FEATURE:
<221> NAME/KEY: CDS
<222> LOCATION: (1)..(201)

<400> SEQUENCE: 40 atg ttc acc gtg ttt ctg ttg gtt gtc ttg gca acc act gtc gtt tcc    48
Met Phe Thr Val Phe Leu Leu Val Val Leu Ala Thr Thr Val Val Ser
 1               5                  10                  15 ttc cct tca gat cgt gca tct gat ggc agg gat gac gaa gcc aaa gac    96
Phe Pro Ser Asp Arg Ala Ser Asp Gly Arg Asp Asp Glu Ala Lys Asp
                20                  25                  30
```

```
                20                  25                  30
gaa agg tct gac atg cac gaa tcg gac cgg aat gga cgc gga tgc tgt        144
Glu Arg Ser Asp Met His Glu Ser Asp Arg Asn Gly Arg Gly Cys Cys
            35                  40                  45 tgc aat cct gcc tgt ggc cca aac tat ggt tgt ggc acc tca tgc tcc        192
Cys Asn Pro Ala Cys Gly Pro Asn Tyr Gly Cys Gly Thr Ser Cys Ser
 50                  55                  60 agg acc ctc tgaaccacga cgttcgagca                                      221
Arg Thr Leu
 65
```

<210> SEQ ID NO 41
<211> LENGTH: 67
<212> TYPE: PRT
<213> ORGANISM: Conus striatus

<400> SEQUENCE: 41

```
Met Phe Thr Val Phe Leu Leu Val Val Leu Ala Thr Thr Val Val Ser
 1               5                  10                  15

Phe Pro Ser Asp Arg Ala Ser Asp Gly Arg Asp Asp Glu Ala Lys Asp
            20                  25                  30

Glu Arg Ser Asp Met His Glu Ser Asp Arg Asn Gly Arg Gly Cys Cys
            35                  40                  45

Cys Asn Pro Ala Cys Gly Pro Asn Tyr Gly Cys Gly Thr Ser Cys Ser
 50                  55                  60

Arg Thr Leu
 65
```

<210> SEQ ID NO 42
<211> LENGTH: 45
<212> TYPE: DNA
<213> ORGANISM: Conus striatus
<220> FEATURE:
<221> NAME/KEY: CDS
<222> LOCATION: (1)..(42)

<400> SEQUENCE: 42

```
tgt tgc cat cct gcc tgt ggc aga aag tat aat tgt gga cgc tga            45
Cys Cys His Pro Ala Cys Gly Arg Lys Tyr Asn Cys Gly Arg
 1               5                  10
```

<210> SEQ ID NO 43
<211> LENGTH: 14
<212> TYPE: PRT
<213> ORGANISM: Conus striatus

<400> SEQUENCE: 43

```
Cys Cys His Pro Ala Cys Gly Arg Lys Tyr Asn Cys Gly Arg
 1               5                  10
```

<210> SEQ ID NO 44
<211> LENGTH: 78
<212> TYPE: DNA
<213> ORGANISM: Conus striatus
<220> FEATURE:
<221> NAME/KEY: CDS
<222> LOCATION: (1)..(75)

<400> SEQUENCE: 44

```
tgc tgt tgc aat cct gcc tgt ggc cca aac tat ggt tgt ggc acc tca        48
Cys Cys Cys Asn Pro Ala Cys Gly Pro Asn Tyr Gly Cys Gly Thr Ser
 1               5                  10                  15 tgc tcc aga ccc tct gaa cca cga cgt tag                                78
```

<210> SEQ ID NO 45
<211> LENGTH: 25
<212> TYPE: PRT
<213> ORGANISM: Conus striatus

<400> SEQUENCE: 45

Cys Cys Cys Asn Pro Ala Cys Gly Pro Asn Tyr Gly Cys Gly Thr Ser
1               5                   10                  15

Cys Ser Arg Pro Ser Glu Pro Arg Arg
            20                  25

<210> SEQ ID NO 46
<211> LENGTH: 1010
<212> TYPE: DNA
<213> ORGANISM: Conus geographus
<220> FEATURE:
<221> NAME/KEY: CDS
<222> LOCATION: (1)..(177)

<400> SEQUENCE: 46

| | |
|---|---:|
| atg ttc acc gtg ttt ctg ttg gtg gtc ttg gca acc act gtc gtt tcc<br>Met Phe Thr Val Phe Leu Leu Val Val Leu Ala Thr Thr Val Val Ser<br>1               5                  10              15 | 48 |
| ttc cct tca gaa cgt gca tct gat ggc agg gat gac aca gcc aaa gac<br>Phe Pro Ser Glu Arg Ala Ser Asp Gly Arg Asp Asp Thr Ala Lys Asp<br>               20                  25                  30 | 96 |
| gaa ggg tct gac atg gag aaa ttg gtc gag aaa aaa gaa tgt tgc aat<br>Glu Gly Ser Asp Met Glu Lys Leu Val Glu Lys Lys Glu Cys Cys Asn<br>       35                  40                  45 | 144 |
| cct gcc tgt ggc aga cac tac agt tgt aag gga ggacgctgat gctccaggac<br>Pro Ala Cys Gly Arg His Tyr Ser Cys Lys Gly<br>50                  55 | 197 |
| cctctgaacc acggacgtgc cgccctctgc ctgacctgct tcactgtccg tctctttgtg | 257 |
| ccactagaac tgaacagctc gatccactag actaccacgt tacctccgtg ttctaaaact | 317 |
| acttggttta gattgccttt aatttctagt catacttcct gttattacgt cgtccaaaat | 377 |
| tgaaacaaga acatgagggg tgtcagctca aacaaaatca ggcaatgaca aggaaaatgt | 437 |
| ctccgatcga tccgaaaact gtcacccgtc actctcttaa ccagttttag aactgattac | 497 |
| cactagagct tttgtaccac atcaaatcag gtctatgtgt gatgtttctt ttgcaaaatt | 557 |
| taatttttga gaaaaaagc tcaaaatgtg ggaagtgctt tgattttct gacaacttgt | 617 |
| gatcatgtcc gttttcagtg agtctaattg caacctctgt gtgattttct tcacctgtta | 677 |
| agcaacgcaa agaggttgtc cataaccagg aaagcaacag acaaagaaat gcttgagaat | 737 |
| ttcaggttat agataaggta aggaaaaaaa ggagagctat gggaaatgat gaaaacaaca | 797 |
| gataaaataa attgaacagt acctacttgt ttcatggttg atttttttt ctctgaataa | 857 |
| tctctgtgga cactaatggc agtctctcct caccccacgc cattagtaag cttatttttt | 917 |
| ctttctttat ccaagatttg ctgaacatat ttagcctaga tatagacatt gctacatata | 977 |
| taatctgaca ataaactttc atgggcacca att | 1010 |

<210> SEQ ID NO 47
<211> LENGTH: 59
<212> TYPE: PRT
<213> ORGANISM: Conus geographus

<400> SEQUENCE: 47

```
Met Phe Thr Val Phe Leu Leu Val Val Leu Ala Thr Thr Val Val Ser
 1               5                  10                  15

Phe Pro Ser Glu Arg Ala Ser Asp Gly Arg Asp Asp Thr Ala Lys Asp
             20                  25                  30

Glu Gly Ser Asp Met Glu Lys Leu Val Glu Lys Glu Cys Cys Asn
         35                  40                  45

Pro Ala Cys Gly Arg His Tyr Ser Cys Lys Gly
     50                  55
```

<210> SEQ ID NO 48
<211> LENGTH: 208
<212> TYPE: DNA
<213> ORGANISM: Conus monachus
<220> FEATURE:
<221> NAME/KEY: CDS
<222> LOCATION: (1)..(180)

<400> SEQUENCE: 48

```
atg ttc acc gtg ttt ctg ttg gtt gtc ttg aca acc act gtc gtt tcc      48
Met Phe Thr Val Phe Leu Leu Val Val Leu Thr Thr Thr Val Val Ser
 1               5                  10                  15 ttc cct tca gat agt gca tct ggt ggc agg gat gac gag gcc aaa gac      96
Phe Pro Ser Asp Ser Ala Ser Gly Gly Arg Asp Asp Glu Ala Lys Asp
             20                  25                  30 gaa agg tct gac atg tac gaa ttg aaa cgg aat gga cac tgt tgc cat     144
Glu Arg Ser Asp Met Tyr Glu Leu Lys Arg Asn Gly His Cys Cys His
         35                  40                  45 cct gcc tgt ggt ggc aaa tac gtt aaa tgt gga cgc tgatgctcca          190
Pro Ala Cys Gly Gly Lys Tyr Val Lys Cys Gly Arg
     50                  55                  60 ggaccctctc gaaccacg                                                  208
```

<210> SEQ ID NO 49
<211> LENGTH: 60
<212> TYPE: PRT
<213> ORGANISM: Conus monachus

<400> SEQUENCE: 49

```
Met Phe Thr Val Phe Leu Leu Val Val Leu Thr Thr Thr Val Val Ser
 1               5                  10                  15

Phe Pro Ser Asp Ser Ala Ser Gly Gly Arg Asp Asp Glu Ala Lys Asp
             20                  25                  30

Glu Arg Ser Asp Met Tyr Glu Leu Lys Arg Asn Gly His Cys Cys His
         35                  40                  45

Pro Ala Cys Gly Gly Lys Tyr Val Lys Cys Gly Arg
     50                  55                  60
```

<210> SEQ ID NO 50
<211> LENGTH: 208
<212> TYPE: DNA
<213> ORGANISM: Conus achatinus
<220> FEATURE:
<221> NAME/KEY: CDS
<222> LOCATION: (1)..(180)

<400> SEQUENCE: 50

```
atg ttc acc gtg ttt ctg ttg gtt gtc ttg aca acc act gtc gtt tcc      48
Met Phe Thr Val Phe Leu Leu Val Val Leu Thr Thr Thr Val Val Ser
 1               5                  10                  15 ttc cct tca gat agt gca tct ggt ggc agg gat gac gag gcc aaa gac      96
Phe Pro Ser Asp Ser Ala Ser Gly Gly Arg Asp Asp Glu Ala Lys Asp
             20                  25                  30
```

```
                    20                  25                  30
gaa agg tct gac atg tac gaa ttg aaa cgg aat gga cgc tgt tgc cat        144
Glu Arg Ser Asp Met Tyr Glu Leu Lys Arg Asn Gly Arg Cys Cys His
            35                  40                  45 cct gcc tgt ggt ggc aaa tac gtt aaa tgt gga cgc tgatgctcca             190
Pro Ala Cys Gly Gly Lys Tyr Val Lys Cys Gly Arg
        50                  55                  60 ggaccctctc gaaccacg                                                     208

<210> SEQ ID NO 51
<211> LENGTH: 60
<212> TYPE: PRT
<213> ORGANISM: Conus achatinus

<400> SEQUENCE: 51

Met Phe Thr Val Phe Leu Leu Val Val Leu Thr Thr Thr Val Val Ser
 1               5                  10                  15

Phe Pro Ser Asp Ser Ala Ser Gly Gly Arg Asp Asp Glu Ala Lys Asp
                20                  25                  30

Glu Arg Ser Asp Met Tyr Glu Leu Lys Arg Asn Gly Arg Cys Cys His
            35                  40                  45

Pro Ala Cys Gly Gly Lys Tyr Val Lys Cys Gly Arg
        50                  55                  60

<210> SEQ ID NO 52
<211> LENGTH: 208
<212> TYPE: DNA
<213> ORGANISM: Conus achatinus
<220> FEATURE:
<221> NAME/KEY: CDS
<222> LOCATION: (1)..(177)

<400> SEQUENCE: 52 atg ttc acc gtg ttt ctg ttg gtt gtc ttg aca aca act gtc gtt tcc         48
Met Phe Thr Val Phe Leu Leu Val Val Leu Thr Thr Thr Val Val Ser
 1               5                  10                  15 tac cct tca gat agt gca tct gat ggc agg gat gac gaa gcc aaa gac         96
Tyr Pro Ser Asp Ser Ala Ser Asp Gly Arg Asp Asp Glu Ala Lys Asp
                20                  25                  30 gaa agg tct gac atg tac aaa tcg aaa cgg aat gga cgc tgt tgc cat        144
Glu Arg Ser Asp Met Tyr Lys Ser Lys Arg Asn Gly Arg Cys Cys His
            35                  40                  45 cct gcc tgt ggc aaa cac ttt agt tgt gga cgc tgatgctcca ggaccctctg      197
Pro Ala Cys Gly Lys His Phe Ser Cys Gly Arg
        50                  55 aaccacgacg t                                                           208

<210> SEQ ID NO 53
<211> LENGTH: 59
<212> TYPE: PRT
<213> ORGANISM: Conus achatinus

<400> SEQUENCE: 53

Met Phe Thr Val Phe Leu Leu Val Val Leu Thr Thr Thr Val Val Ser
 1               5                  10                  15

Tyr Pro Ser Asp Ser Ala Ser Asp Gly Arg Asp Asp Glu Ala Lys Asp
                20                  25                  30

Glu Arg Ser Asp Met Tyr Lys Ser Lys Arg Asn Gly Arg Cys Cys His
            35                  40                  45

Pro Ala Cys Gly Lys His Phe Ser Cys Gly Arg
```

<210> SEQ ID NO 54
<211> LENGTH: 208
<212> TYPE: DNA
<213> ORGANISM: Conus betulinus
<220> FEATURE:
<221> NAME/KEY: CDS
<222> LOCATION: (1)..(177)

<400> SEQUENCE: 54

| atg | ttc | acc | gtg | ttt | ctg | ttg | gtt | gtc | ttg | gca | acc | act | gtc | gtt | tcc | 48 |
| Met | Phe | Thr | Val | Phe | Leu | Leu | Val | Val | Leu | Ala | Thr | Thr | Val | Val | Ser | |
| 1 | | | | 5 | | | | | 10 | | | | | 15 | | |

| tac | cct | tca | gat | agt | gca | tct | gat | ggc | agg | gat | gac | gaa | acc | aaa | gac | 96 |
| Tyr | Pro | Ser | Asp | Ser | Ala | Ser | Asp | Gly | Arg | Asp | Asp | Glu | Thr | Lys | Asp | |
| | | | | 20 | | | | | 25 | | | | | 30 | | |

| gaa | aag | tct | gac | atg | tac | aaa | tcg | aaa | cgg | aat | gga | cgc | tgt | tgc | cat | 144 |
| Glu | Lys | Ser | Asp | Met | Tyr | Lys | Ser | Lys | Arg | Asn | Gly | Arg | Cys | Cys | His | |
| | | 35 | | | | | 40 | | | | | 45 | | | | |

| cct | gcc | tgt | ggc | aaa | cac | ttt | agt | tgt | gga | cgc | tgatgctgca | ggaccctctg | | | | 197 |
| Pro | Ala | Cys | Gly | Lys | His | Phe | Ser | Cys | Gly | Arg | | | | | | |
| | 50 | | | | | 55 | | | | | | | | | | | aaccacgacg t    208

<210> SEQ ID NO 55
<211> LENGTH: 59
<212> TYPE: PRT
<213> ORGANISM: Conus betulinus

<400> SEQUENCE: 55

Met Phe Thr Val Phe Leu Leu Val Val Leu Ala Thr Thr Val Val Ser
1               5                   10                  15

Tyr Pro Ser Asp Ser Ala Ser Asp Gly Arg Asp Asp Glu Thr Lys Asp
            20                  25                  30

Glu Lys Ser Asp Met Tyr Lys Ser Lys Arg Asn Gly Arg Cys Cys His
        35                  40                  45

Pro Ala Cys Gly Lys His Phe Ser Cys Gly Arg
    50                  55

<210> SEQ ID NO 56
<211> LENGTH: 208
<212> TYPE: DNA
<213> ORGANISM: Conus consors
<220> FEATURE:
<221> NAME/KEY: CDS
<222> LOCATION: (1)..(177)

<400> SEQUENCE: 56

| atg | ttc | acc | gtg | ttt | ctg | ttg | gtt | gtc | ttg | aca | acc | act | gtc | gtt | tcc | 48 |
| Met | Phe | Thr | Val | Phe | Leu | Leu | Val | Val | Leu | Thr | Thr | Thr | Val | Val | Ser | |
| 1 | | | | 5 | | | | | 10 | | | | | 15 | | |

| ttc | cct | tca | gat | agt | gca | tct | gat | gtc | agg | gat | gac | gaa | gcc | aaa | gac | 96 |
| Phe | Pro | Ser | Asp | Ser | Ala | Ser | Asp | Val | Arg | Asp | Asp | Glu | Ala | Lys | Asp | |
| | | | | 20 | | | | | 25 | | | | | 30 | | |

| gaa | agg | tct | gac | atg | tac | aaa | tcg | aaa | cgg | aat | gga | cgc | tgt | tgc | cat | 144 |
| Glu | Arg | Ser | Asp | Met | Tyr | Lys | Ser | Lys | Arg | Asn | Gly | Arg | Cys | Cys | His | |
| | | 35 | | | | | 40 | | | | | 45 | | | | |

| cct | gcc | tgt | ggc | aaa | cac | ttt | agt | tgt | gga | cgc | tgatgctcca | ggaccctctg | | | | 197 |
| Pro | Ala | Cys | Gly | Lys | His | Phe | Ser | Cys | Gly | Arg | | | | | | |
| | 50 | | | | | 55 | | | | | | | | | | | aaccacgacg t    208

<210> SEQ ID NO 57
<211> LENGTH: 59
<212> TYPE: PRT
<213> ORGANISM: Conus consors

<400> SEQUENCE: 57

Met Phe Thr Val Phe Leu Leu Val Val Leu Thr Thr Thr Val Val Ser
1               5                   10                  15

Phe Pro Ser Asp Ser Ala Ser Asp Val Arg Asp Asp Glu Ala Lys Asp
            20                  25                  30

Glu Arg Ser Asp Met Tyr Lys Ser Lys Arg Asn Gly Arg Cys Cys His
        35                  40                  45

Pro Ala Cys Gly Lys His Phe Ser Cys Gly Arg
    50                  55

<210> SEQ ID NO 58
<211> LENGTH: 208
<212> TYPE: DNA
<213> ORGANISM: Conus monachus
<220> FEATURE:
<221> NAME/KEY: CDS
<222> LOCATION: (1)..(177)

<400> SEQUENCE: 58 atg ttc acc gtg ttt ctg ttg gtt gtc ttg aca aca act gtc gtt tcc      48
Met Phe Thr Val Phe Leu Leu Val Val Leu Thr Thr Thr Val Val Ser
1               5                   10                  15 tac cct tca gat agt gca tct gat ggc agg gat gac gaa gcc aaa gac      96
Tyr Pro Ser Asp Ser Ala Ser Asp Gly Arg Asp Asp Glu Ala Lys Asp
            20                  25                  30 gaa agg tct gac atg tac aaa tcg aaa cgg aat gga cgc tgt tgc cat     144
Glu Arg Ser Asp Met Tyr Lys Ser Lys Arg Asn Gly Arg Cys Cys His
        35                  40                  45 cct gcc tgt ggc aaa cac ttt agt tgt gga cgc tgatgctcca ggaccctctg   197
Pro Ala Cys Gly Lys His Phe Ser Cys Gly Arg
    50                  55 aaccacgacg t                                                        208

<210> SEQ ID NO 59
<211> LENGTH: 59
<212> TYPE: PRT
<213> ORGANISM: Conus monachus

<400> SEQUENCE: 59

Met Phe Thr Val Phe Leu Leu Val Val Leu Thr Thr Thr Val Val Ser
1               5                   10                  15

Tyr Pro Ser Asp Ser Ala Ser Asp Gly Arg Asp Asp Glu Ala Lys Asp
            20                  25                  30

Glu Arg Ser Asp Met Tyr Lys Ser Lys Arg Asn Gly Arg Cys Cys His
        35                  40                  45

Pro Ala Cys Gly Lys His Phe Ser Cys Gly Arg
    50                  55

<210> SEQ ID NO 60
<211> LENGTH: 213
<212> TYPE: DNA
<213> ORGANISM: Conus circumcisus
<220> FEATURE:
<221> NAME/KEY: CDS
<222> LOCATION: (1)..(183)

```
<400> SEQUENCE: 60 atg ttc acc gtg ttt ctg ttg gtt gtc ttg gca gcc act gtc gtt tcc         48
Met Phe Thr Val Phe Leu Leu Val Val Leu Ala Ala Thr Val Val Ser
 1               5                  10                  15 ttc cct tca gat cgt gca tct gat ggc agg gat gac gaa gcc aaa gac         96
Phe Pro Ser Asp Arg Ala Ser Asp Gly Arg Asp Asp Glu Ala Lys Asp
             20                  25                  30 gaa aga tct gac atg cac gaa tcg gac cgg aaa gga cgc gga cgc tgt        144
Glu Arg Ser Asp Met His Glu Ser Asp Arg Lys Gly Arg Gly Arg Cys
         35                  40                  45 tgc cat cct gcc tgt ggc cca aat tat agt tgt gga cgc tgatgctcca         193
Cys His Pro Ala Cys Gly Pro Asn Tyr Ser Cys Gly Arg
     50                  55                  60 ggaccctctg aaccacgacg                                                   213

<210> SEQ ID NO 61
<211> LENGTH: 61
<212> TYPE: PRT
<213> ORGANISM: Conus circumcisus

<400> SEQUENCE: 61

Met Phe Thr Val Phe Leu Leu Val Val Leu Ala Ala Thr Val Val Ser
 1               5                  10                  15

Phe Pro Ser Asp Arg Ala Ser Asp Gly Arg Asp Asp Glu Ala Lys Asp
             20                  25                  30

Glu Arg Ser Asp Met His Glu Ser Asp Arg Lys Gly Arg Gly Arg Cys
         35                  40                  45

Cys His Pro Ala Cys Gly Pro Asn Tyr Ser Cys Gly Arg
     50                  55                  60

<210> SEQ ID NO 62
<211> LENGTH: 208
<212> TYPE: DNA
<213> ORGANISM: Conus radiatus
<220> FEATURE:
<221> NAME/KEY: CDS
<222> LOCATION: (1)..(177)

<400> SEQUENCE: 62 atg ttc acc gtg ttt ctg ttg gtg gtc ttg gca acc act gtc gtt tcc         48
Met Phe Thr Val Phe Leu Leu Val Val Leu Ala Thr Thr Val Val Ser
 1               5                  10                  15 ttc cct tca gaa cgt gca tct gat ggc agg gat gac aca gcc aaa gac         96
Phe Pro Ser Glu Arg Ala Ser Asp Gly Arg Asp Asp Thr Ala Lys Asp
             20                  25                  30 gaa ggg tct gac atg gac aaa ttg gtc gag aaa aaa gaa tgt tgc cat        144
Glu Gly Ser Asp Met Asp Lys Leu Val Glu Lys Lys Glu Cys Cys His
         35                  40                  45 cct gcc tgt ggc aaa cac ttc agt tgt gga cgc tgatgctcca ggaccctctg      197
Pro Ala Cys Gly Lys His Phe Ser Cys Gly Arg
     50                  55 aaccacgacg t                                                            208

<210> SEQ ID NO 63
<211> LENGTH: 59
<212> TYPE: PRT
<213> ORGANISM: Conus radiatus

<400> SEQUENCE: 63

Met Phe Thr Val Phe Leu Leu Val Val Leu Ala Thr Thr Val Val Ser
 1               5                  10                  15
```

```
Phe Pro Ser Glu Arg Ala Ser Asp Gly Arg Asp Asp Thr Ala Lys Asp
            20                  25                  30

Glu Gly Ser Asp Met Asp Lys Leu Val Glu Lys Lys Glu Cys Cys His
        35                  40                  45

Pro Ala Cys Gly Lys His Phe Ser Cys Gly Arg
        50                  55

<210> SEQ ID NO 64
<211> LENGTH: 114
<212> TYPE: DNA
<213> ORGANISM: Conus achatinus
<220> FEATURE:
<221> NAME/KEY: CDS
<222> LOCATION: (1)..(111)

<400> SEQUENCE: 64 tct gat ggc agg gat gac gaa gcc aaa gac gaa agg tct gac atg tac      48
Ser Asp Gly Arg Asp Asp Glu Ala Lys Asp Glu Arg Ser Asp Met Tyr
 1               5                  10                  15 aaa tcg aaa cgg aat gga cgc tgt tgc cac cct gcc tgt ggc aaa cac      96
Lys Ser Lys Arg Asn Gly Arg Cys Cys His Pro Ala Cys Gly Lys His
            20                  25                  30 ttt att tgt gga cgc tga                                             114
Phe Ile Cys Gly Arg
        35

<210> SEQ ID NO 65
<211> LENGTH: 37
<212> TYPE: PRT
<213> ORGANISM: Conus achatinus

<400> SEQUENCE: 65

Ser Asp Gly Arg Asp Asp Glu Ala Lys Asp Glu Arg Ser Asp Met Tyr
 1               5                  10                  15

Lys Ser Lys Arg Asn Gly Arg Cys Cys His Pro Ala Cys Gly Lys His
            20                  25                  30

Phe Ile Cys Gly Arg
        35

<210> SEQ ID NO 66
<211> LENGTH: 114
<212> TYPE: DNA
<213> ORGANISM: Conus achatinus
<220> FEATURE:
<221> NAME/KEY: CDS
<222> LOCATION: (1)..(111)

<400> SEQUENCE: 66 tct ggt ggc agg gat gac gaa gcc aaa gac gaa agg tct gac atg tac      48
Ser Gly Gly Arg Asp Asp Glu Ala Lys Asp Glu Arg Ser Asp Met Tyr
 1               5                  10                  15 gaa tcg gac cgg aat gga cgc tgt tgc cat cct gcc tgt ggc aaa cac      96
Glu Ser Asp Arg Asn Gly Arg Cys Cys His Pro Ala Cys Gly Lys His
            20                  25                  30 ttt agt tgt gga cgc tga                                             114
Phe Ser Cys Gly Arg
        35

<210> SEQ ID NO 67
<211> LENGTH: 37
<212> TYPE: PRT
<213> ORGANISM: Conus achatinus
```

```
<400> SEQUENCE: 67

Ser Gly Gly Arg Asp Asp Glu Ala Lys Asp Glu Arg Ser Asp Met Tyr
1               5                   10                  15

Glu Ser Asp Arg Asn Gly Arg Cys Cys His Pro Ala Cys Gly Lys His
            20                  25                  30

Phe Ser Cys Gly Arg
        35

<210> SEQ ID NO 68
<211> LENGTH: 114
<212> TYPE: DNA
<213> ORGANISM: Conus achatinus
<220> FEATURE:
<221> NAME/KEY: CDS
<222> LOCATION: (1)..(111)

<400> SEQUENCE: 68 tct gat ggc agg gat gac gaa gcc aaa gac aaa agg tct gac atg tac      48
Ser Asp Gly Arg Asp Asp Glu Ala Lys Asp Lys Arg Ser Asp Met Tyr
1               5                   10                  15 gaa tcg gac cgg aat gga cgc tgt tgc cat cct tcc tgt gga aga aag      96
Glu Ser Asp Arg Asn Gly Arg Cys Cys His Pro Ser Cys Gly Arg Lys
            20                  25                  30 tat aat tgt gga cgc tga                                              114
Tyr Asn Cys Gly Arg
        35

<210> SEQ ID NO 69
<211> LENGTH: 37
<212> TYPE: PRT
<213> ORGANISM: Conus achatinus

<400> SEQUENCE: 69

Ser Asp Gly Arg Asp Asp Glu Ala Lys Asp Lys Arg Ser Asp Met Tyr
1               5                   10                  15

Glu Ser Asp Arg Asn Gly Arg Cys Cys His Pro Ser Cys Gly Arg Lys
            20                  25                  30

Tyr Asn Cys Gly Arg
        35

<210> SEQ ID NO 70
<211> LENGTH: 142
<212> TYPE: DNA
<213> ORGANISM: Conus aurisiacus
<220> FEATURE:
<221> NAME/KEY: CDS
<222> LOCATION: (49)..(111)

<400> SEQUENCE: 70
tctgatggca gggatgacga agccaaagac gaaaggtctg acatgtac gaa tcg gac     57
                                                     Glu Ser Asp
                                                             1 cgg aat gga cgc tgt tgc cat cct gcc tgt gcg aga aag tat aat tgt      105
Arg Asn Gly Arg Cys Cys His Pro Ala Cys Ala Arg Lys Tyr Asn Cys
        5                   10                  15 gga cgc tgatgctcca ggaccctctg aaccacgacg t                           142
Gly Arg
 20

<210> SEQ ID NO 71
<211> LENGTH: 21
<212> TYPE: PRT
<213> ORGANISM: Conus aurisiacus
```

```
<400> SEQUENCE: 71

Glu Ser Asp Arg Asn Gly Arg Cys Cys His Pro Ala Cys Ala Arg Lys
 1               5                  10                  15

Tyr Asn Cys Gly Arg
            20

<210> SEQ ID NO 72
<211> LENGTH: 142
<212> TYPE: DNA
<213> ORGANISM: Conus aurisiacus
<220> FEATURE:
<221> NAME/KEY: CDS
<222> LOCATION: (49)..(111)

<400> SEQUENCE: 72
tctgatggca gggatgacga agccaaagac gaaaggtctg acatgtac gaa tcg gag        57
                                                   Glu Ser Glu
                                                     1 cgg aat gaa cgc tgt tgc cat cct gcc tgt gcg aga aag tat aat tgt       105
Arg Asn Glu Arg Cys Cys His Pro Ala Cys Ala Arg Lys Tyr Asn Cys
      5                  10                  15 gga cgc tgatgctcca ggaccctctg aaccacgacg t                            142
Gly Arg
 20

<210> SEQ ID NO 73
<211> LENGTH: 21
<212> TYPE: PRT
<213> ORGANISM: Conus aurisiacus

<400> SEQUENCE: 73

Glu Ser Glu Arg Asn Glu Arg Cys Cys His Pro Ala Cys Ala Arg Lys
 1               5                  10                  15

Tyr Asn Cys Gly Arg
            20

<210> SEQ ID NO 74
<211> LENGTH: 208
<212> TYPE: DNA
<213> ORGANISM: Conus magus
<220> FEATURE:
<221> NAME/KEY: CDS
<222> LOCATION: (1)..(177)

<400> SEQUENCE: 74 atg ttc acc gtg ttt ctg ttg gtt gtc ttg aca acc act gtc gtt tcc        48
Met Phe Thr Val Phe Leu Leu Val Val Leu Thr Thr Thr Val Val Ser
 1               5                  10                  15 ttc cct tca gat cgt gca tct gat ggc agg gat gac gaa gcc aaa gac        96
Phe Pro Ser Asp Arg Ala Ser Asp Gly Arg Asp Asp Glu Ala Lys Asp
                20                  25                  30 gaa agg tct gac atg tac gaa tcg aaa cgg gat gga cgc tgt tgc cat       144
Glu Arg Ser Asp Met Tyr Glu Ser Lys Arg Asp Gly Arg Cys Cys His
         35                  40                  45 cct gcc tgt ggg caa aac tat agt tgt gga cgc tgatgctcca ggaccctctg    197
Pro Ala Cys Gly Gln Asn Tyr Ser Cys Gly Arg
     50                  55 aaccacgacg t                                                          208

<210> SEQ ID NO 75
<211> LENGTH: 59
<212> TYPE: PRT
```

<213> ORGANISM: Conus magus

<400> SEQUENCE: 75

Met Phe Thr Val Phe Leu Leu Val Val Leu Thr Thr Thr Val Val Ser
1               5                   10                  15

Phe Pro Ser Asp Arg Ala Ser Asp Gly Arg Asp Asp Glu Ala Lys Asp
            20                  25                  30

Glu Arg Ser Asp Met Tyr Glu Ser Lys Arg Asp Gly Arg Cys Cys His
        35                  40                  45

Pro Ala Cys Gly Gln Asn Tyr Ser Cys Gly Arg
    50                  55

<210> SEQ ID NO 76
<211> LENGTH: 142
<212> TYPE: DNA
<213> ORGANISM: Conus magus
<220> FEATURE:
<221> NAME/KEY: CDS
<222> LOCATION: (1)..(111)

<400> SEQUENCE: 76

```
tct gat ggc agg gat gac gaa gcc aaa gac gaa agg cct gac atg tac      48
Ser Asp Gly Arg Asp Asp Glu Ala Lys Asp Glu Arg Pro Asp Met Tyr
1               5                   10                  15 aaa tcg aaa cgg gat gga cgc tgt tgc cat cct gcc tgt gcg aaa cac      96
Lys Ser Lys Arg Asp Gly Arg Cys Cys His Pro Ala Cys Ala Lys His
            20                  25                  30 ttt aat tgt gga cgc tgatgctcca ggaccctctg aaccacgacg t              142
Phe Asn Cys Gly Arg
        35
```

<210> SEQ ID NO 77
<211> LENGTH: 37
<212> TYPE: PRT
<213> ORGANISM: Conus magus

<400> SEQUENCE: 77

Ser Asp Gly Arg Asp Asp Glu Ala Lys Asp Glu Arg Pro Asp Met Tyr
1               5                   10                  15

Lys Ser Lys Arg Asp Gly Arg Cys Cys His Pro Ala Cys Ala Lys His
            20                  25                  30

Phe Asn Cys Gly Arg
        35

<210> SEQ ID NO 78
<211> LENGTH: 142
<212> TYPE: DNA
<213> ORGANISM: Conus magus
<220> FEATURE:
<221> NAME/KEY: CDS
<222> LOCATION: (1)..(111)

<400> SEQUENCE: 78

```
tct gat ggc agg gat gac gaa gcc aaa gac gaa agg tct gac atg tac      48
Ser Asp Gly Arg Asp Asp Glu Ala Lys Asp Glu Arg Ser Asp Met Tyr
1               5                   10                  15 gaa tcg aaa cgg aat gga cgc tgt tgc cat cct gcc tgt gcg aaa aac      96
Glu Ser Lys Arg Asn Gly Arg Cys Cys His Pro Ala Cys Ala Lys Asn
            20                  25                  30 tat agt tgt gga cgc tgatgctcca ggaccctctg aaccacgacg t              142
Tyr Ser Cys Gly Arg
        35
```

```
<210> SEQ ID NO 79
<211> LENGTH: 37
<212> TYPE: PRT
<213> ORGANISM: Conus magus

<400> SEQUENCE: 79

Ser Asp Gly Arg Asp Asp Glu Ala Lys Asp Glu Arg Ser Asp Met Tyr
 1               5                  10                  15

Glu Ser Lys Arg Asn Gly Arg Cys Cys His Pro Ala Cys Ala Lys Asn
                20                  25                  30

Tyr Ser Cys Gly Arg
            35

<210> SEQ ID NO 80
<211> LENGTH: 142
<212> TYPE: DNA
<213> ORGANISM: Conus magus
<220> FEATURE:
<221> NAME/KEY: CDS
<222> LOCATION: (1)..(111)

<400> SEQUENCE: 80 tct gat ggc agg gat gac gaa gcc aaa gac gaa agg tct gac atg tac      48
Ser Asp Gly Arg Asp Asp Glu Ala Lys Asp Glu Arg Ser Asp Met Tyr
 1               5                  10                  15 gaa tcg gac cgg aat gga cgc tgt tgc cat cct gcc tgt gcg aga aag      96
Glu Ser Asp Arg Asn Gly Arg Cys Cys His Pro Ala Cys Ala Arg Lys
                20                  25                  30 tat aat tgt gga cgc tgatgctcca ggaccctctg aaccacgacg t              142
Tyr Asn Cys Gly Arg
            35

<210> SEQ ID NO 81
<211> LENGTH: 37
<212> TYPE: PRT
<213> ORGANISM: Conus magus

<400> SEQUENCE: 81

Ser Asp Gly Arg Asp Asp Glu Ala Lys Asp Glu Arg Ser Asp Met Tyr
 1               5                  10                  15

Glu Ser Asp Arg Asn Gly Arg Cys Cys His Pro Ala Cys Ala Arg Lys
                20                  25                  30

Tyr Asn Cys Gly Arg
            35

<210> SEQ ID NO 82
<211> LENGTH: 142
<212> TYPE: DNA
<213> ORGANISM: Conus obscurus
<220> FEATURE:
<221> NAME/KEY: CDS
<222> LOCATION: (55)..(111)

<400> SEQUENCE: 82
tctgatggca gggatgacac agccaaaaac aaaggatctg acatgaacaa attg gtc      57
                                                          Val
                                                           1 aag aaa aaa caa tgt tgc aat cct gcc tgt ggc cca aag tat agt tgt    105
Lys Lys Lys Gln Cys Cys Asn Pro Ala Cys Gly Pro Lys Tyr Ser Cys
            5                  10                  15 gga cac tgatgctcca ggaccctctg aaccacgacg t                         142
Gly His
```

```
<210> SEQ ID NO 83
<211> LENGTH: 19
<212> TYPE: PRT
<213> ORGANISM: Conus obscurus

<400> SEQUENCE: 83

Val Lys Lys Lys Gln Cys Cys Asn Pro Ala Cys Gly Pro Lys Tyr Ser
 1               5                  10                  15

Cys Gly His

<210> SEQ ID NO 84
<211> LENGTH: 148
<212> TYPE: DNA
<213> ORGANISM: Conus striatus
<220> FEATURE:
<221> NAME/KEY: CDS
<222> LOCATION: (1)..(117)

<400> SEQUENCE: 84 tct gat ggc agg gat gac gaa gcc aaa gac gaa agg tct gac atg cac      48
Ser Asp Gly Arg Asp Asp Glu Ala Lys Asp Glu Arg Ser Asp Met His
 1               5                  10                  15 gaa tcg gac cgg aaa gga cgc gca tac tgt tgc cat cct gcc tgt ggc      96
Glu Ser Asp Arg Lys Gly Arg Ala Tyr Cys Cys His Pro Ala Cys Gly
                20                  25                  30 aaa aag tat aat tgt gga cgc tgatgctcca ggaccctctg aaccacgacg t      148
Lys Lys Tyr Asn Cys Gly Arg
        35

<210> SEQ ID NO 85
<211> LENGTH: 39
<212> TYPE: PRT
<213> ORGANISM: Conus striatus

<400> SEQUENCE: 85

Ser Asp Gly Arg Asp Asp Glu Ala Lys Asp Glu Arg Ser Asp Met His
 1               5                  10                  15

Glu Ser Asp Arg Lys Gly Arg Ala Tyr Cys Cys His Pro Ala Cys Gly
                20                  25                  30

Lys Lys Tyr Asn Cys Gly Arg
        35

<210> SEQ ID NO 86
<211> LENGTH: 226
<212> TYPE: DNA
<213> ORGANISM: Conus ermineus
<220> FEATURE:
<221> NAME/KEY: CDS
<222> LOCATION: (1)..(186)

<400> SEQUENCE: 86 atg ttc acc gtg ttt ctg ttg gtt gtc ttg gca acc act gtc ggt tcc      48
Met Phe Thr Val Phe Leu Leu Val Val Leu Ala Thr Thr Val Gly Ser
 1               5                  10                  15 ttc act tta gat cgt gca tct gat ggt agg gat gcc gca gcc aac gac      96
Phe Thr Leu Asp Arg Ala Ser Asp Gly Arg Asp Ala Ala Ala Asn Asp
                20                  25                  30 aaa gcg tct gac ctg atc gct ctg acc gcc agg aga gat cca tgc tgt     144
Lys Ala Ser Asp Leu Ile Ala Leu Thr Ala Arg Arg Asp Pro Cys Cys
        35                  40                  45 tac cat cct acc tgt aac atg agt aat cca cag att tgt ggt             186
Tyr His Pro Thr Cys Asn Met Ser Asn Pro Gln Ile Cys Gly
    50                  55                  60
```
tgaagacgct gatgctccag gaccctctga accacgacgt         226

<210> SEQ ID NO 87
<211> LENGTH: 62
<212> TYPE: PRT
<213> ORGANISM: Conus ermineus

<400> SEQUENCE: 87

Met Phe Thr Val Phe Leu Leu Val Val Leu Ala Thr Thr Val Gly Ser
1               5                   10                  15

Phe Thr Leu Asp Arg Ala Ser Asp Gly Arg Asp Ala Ala Ala Asn Asp
            20                  25                  30

Lys Ala Ser Asp Leu Ile Ala Leu Thr Ala Arg Arg Asp Pro Cys Cys
        35                  40                  45

Tyr His Pro Thr Cys Asn Met Ser Asn Pro Gln Ile Cys Gly
    50                  55                  60

<210> SEQ ID NO 88
<211> LENGTH: 226
<212> TYPE: DNA
<213> ORGANISM: Conus ermineus
<220> FEATURE:
<221> NAME/KEY: CDS
<222> LOCATION: (1)..(186)

<400> SEQUENCE: 88 atg ttc acc gtg ttt ctg ttg gtt gtc ttg gca acc act gtc ggt tcc    48
Met Phe Thr Val Phe Leu Leu Val Val Leu Ala Thr Thr Val Gly Ser
1               5                   10                  15 ttc act tta gat cgt gca tct gat ggt agg gat gcc gca gcc aac gac    96
Phe Thr Leu Asp Arg Ala Ser Asp Gly Arg Asp Ala Ala Ala Asn Asp
            20                  25                  30 aaa gcg tct gac ctg atc gct ctg acc gcc agg aga gat cca tgc tgt   144
Lys Ala Ser Asp Leu Ile Ala Leu Thr Ala Arg Arg Asp Pro Cys Cys
        35                  40                  45 tcc aat cct gcc tgt aac gtg aat aat cca cag att tgt ggt           186
Ser Asn Pro Ala Cys Asn Val Asn Asn Pro Gln Ile Cys Gly
    50                  55                  60 tgaagacgct gatgctccag gaccctctga accacgacgt         226

<210> SEQ ID NO 89
<211> LENGTH: 62
<212> TYPE: PRT
<213> ORGANISM: Conus ermineus

<400> SEQUENCE: 89

Met Phe Thr Val Phe Leu Leu Val Val Leu Ala Thr Thr Val Gly Ser
1               5                   10                  15

Phe Thr Leu Asp Arg Ala Ser Asp Gly Arg Asp Ala Ala Ala Asn Asp
            20                  25                  30

Lys Ala Ser Asp Leu Ile Ala Leu Thr Ala Arg Arg Asp Pro Cys Cys
        35                  40                  45

Ser Asn Pro Ala Cys Asn Val Asn Asn Pro Gln Ile Cys Gly
    50                  55                  60

<210> SEQ ID NO 90
<211> LENGTH: 172
<212> TYPE: DNA
<213> ORGANISM: Conus purpurascens
<220> FEATURE:
<221> NAME/KEY: CDS

```
<222> LOCATION: (1)..(132)

<400> SEQUENCE: 90 atg ttc acc gtg ttt ctg ttg gtg gat gcc gca gcc aac gac aag gcg      48
Met Phe Thr Val Phe Leu Leu Val Asp Ala Ala Ala Asn Asp Lys Ala
 1               5                  10                  15 tct gac cgg atc gct ctg acc gcc agg aga gat cca tgc tgt tcc aat      96
Ser Asp Arg Ile Ala Leu Thr Ala Arg Arg Asp Pro Cys Cys Ser Asn
             20                  25                  30 cct gtc tgt acc gtg cat aat cca cag att tgt ggt tgaagacgct          142
Pro Val Cys Thr Val His Asn Pro Gln Ile Cys Gly
         35                  40 gatgctccag gaccctctga accacgacgt                                    172

<210> SEQ ID NO 91
<211> LENGTH: 44
<212> TYPE: PRT
<213> ORGANISM: Conus purpurascens

<400> SEQUENCE: 91

Met Phe Thr Val Phe Leu Leu Val Asp Ala Ala Ala Asn Asp Lys Ala
 1               5                  10                  15

Ser Asp Arg Ile Ala Leu Thr Ala Arg Arg Asp Pro Cys Cys Ser Asn
             20                  25                  30

Pro Val Cys Thr Val His Asn Pro Gln Ile Cys Gly
         35                  40

<210> SEQ ID NO 92
<211> LENGTH: 220
<212> TYPE: DNA
<213> ORGANISM: Conus purpurascens
<220> FEATURE:
<221> NAME/KEY: CDS
<222> LOCATION: (1)..(189)

<400> SEQUENCE: 92 atg ttc acc gtg ttt ctg ttg gtt gtc ttg gta acc acc gtc gtt tcc      48
Met Phe Thr Val Phe Leu Leu Val Val Leu Val Thr Thr Val Val Ser
 1               5                  10                  15 ttc aat tca gat cgt gca tta ggt ggc agg aat gct gca gcc aaa gcg      96
Phe Asn Ser Asp Arg Ala Leu Gly Gly Arg Asn Ala Ala Ala Lys Ala
             20                  25                  30 tct gac aag atc gct tcg atc ctc ggg aga aga gca tgc tgt tct tat     144
Ser Asp Lys Ile Ala Ser Ile Leu Gly Arg Arg Ala Cys Cys Ser Tyr
         35                  40                  45 cct ccc tgt aac gtg aac tat cca gaa att tgt ggt gga cga ggc         189
Pro Pro Cys Asn Val Asn Tyr Pro Glu Ile Cys Gly Gly Arg Gly
     50                  55                  60 tgatgctcca ggaccctctg aaccacgacg t                                  220

<210> SEQ ID NO 93
<211> LENGTH: 63
<212> TYPE: PRT
<213> ORGANISM: Conus purpurascens

<400> SEQUENCE: 93

Met Phe Thr Val Phe Leu Leu Val Val Leu Val Thr Thr Val Val Ser
 1               5                  10                  15

Phe Asn Ser Asp Arg Ala Leu Gly Gly Arg Asn Ala Ala Ala Lys Ala
             20                  25                  30

Ser Asp Lys Ile Ala Ser Ile Leu Gly Arg Arg Ala Cys Cys Ser Tyr
```

```
                 35                  40                  45
Pro Pro Cys Asn Val Asn Tyr Pro Glu Ile Cys Gly Gly Arg Gly
         50                  55                  60
```

<210> SEQ ID NO 94
<211> LENGTH: 226
<212> TYPE: DNA
<213> ORGANISM: Conus sulcatus
<220> FEATURE:
<221> NAME/KEY: CDS
<222> LOCATION: (1)..(195)

<400> SEQUENCE: 94

```
atg ttc acc gtg ttt ctg ttg gtt gtc ttg gca acc acc gtc gtt ccc      48
Met Phe Thr Val Phe Leu Leu Val Val Leu Ala Thr Thr Val Val Pro
 1               5                  10                  15 ttc aat tca gat cgt gat cca gca tta ggt ggc agg aat gct gca gcc      96
Phe Asn Ser Asp Arg Asp Pro Ala Leu Gly Gly Arg Asn Ala Ala Ala
                 20                  25                  30 ata gcg tct gac aag atc gct tcg acc ctc agg aga gga gga tgc tgt     144
Ile Ala Ser Asp Lys Ile Ala Ser Thr Leu Arg Arg Gly Gly Cys Cys
         35                  40                  45 tct tat cct ccc tgt aac gtg tcc tat cca gaa att tgt ggt gga cga     192
Ser Tyr Pro Pro Cys Asn Val Ser Tyr Pro Glu Ile Cys Gly Gly Arg
 50                  55                  60 cgc tgatgctcca ggaccctctg aaccacgacg t                              226
Arg
 65
```

<210> SEQ ID NO 95
<211> LENGTH: 65
<212> TYPE: PRT
<213> ORGANISM: Conus sulcatus

<400> SEQUENCE: 95

```
Met Phe Thr Val Phe Leu Leu Val Val Leu Ala Thr Thr Val Val Pro
 1               5                  10                  15

Phe Asn Ser Asp Arg Asp Pro Ala Leu Gly Gly Arg Asn Ala Ala Ala
                 20                  25                  30

Ile Ala Ser Asp Lys Ile Ala Ser Thr Leu Arg Arg Gly Gly Cys Cys
         35                  40                  45

Ser Tyr Pro Pro Cys Asn Val Ser Tyr Pro Glu Ile Cys Gly Gly Arg
 50                  55                  60

Arg
 65
```

<210> SEQ ID NO 96
<211> LENGTH: 220
<212> TYPE: DNA
<213> ORGANISM: Conus sulcatus
<220> FEATURE:
<221> NAME/KEY: CDS
<222> LOCATION: (1)..(189)

<400> SEQUENCE: 96

```
atg ttc acc gtg ttt ctg ttg gtt gtc ttg gca acc acc gtc gtt tcc      48
Met Phe Thr Val Phe Leu Leu Val Val Leu Ala Thr Thr Val Val Ser
 1               5                  10                  15 ttc aat tca gat cgt gca tta ggt ggc agg aat gct gca gcc aaa gcg      96
Phe Asn Ser Asp Arg Ala Leu Gly Gly Arg Asn Ala Ala Ala Lys Ala
                 20                  25                  30 tct gac aag atc gct tcg atc ctc ggg aga aga aga tgc tgt tct tat     144
```

```
Ser Asp Lys Ile Ala Ser Ile Leu Gly Arg Arg Cys Cys Ser Tyr
     35                  40                  45 cct ccc tgt aac gtg tcc tat cca gaa att tgt ggt gga cga cgc      189
Pro Pro Cys Asn Val Ser Tyr Pro Glu Ile Cys Gly Gly Arg Arg
     50                  55                  60 tgatgctcca ggaccctctg aaccacgacg t                                220
```

<210> SEQ ID NO 97
<211> LENGTH: 63
<212> TYPE: PRT
<213> ORGANISM: Conus sulcatus

<400> SEQUENCE: 97

```
Met Phe Thr Val Phe Leu Leu Val Val Leu Ala Thr Thr Val Val Ser
 1               5                  10                  15

Phe Asn Ser Asp Arg Ala Leu Gly Gly Arg Asn Ala Ala Ala Lys Ala
                 20                  25                  30

Ser Asp Lys Ile Ala Ser Ile Leu Gly Arg Arg Cys Cys Ser Tyr
     35                  40                  45

Pro Pro Cys Asn Val Ser Tyr Pro Glu Ile Cys Gly Gly Arg Arg
     50                  55                  60
```

<210> SEQ ID NO 98
<211> LENGTH: 220
<212> TYPE: DNA
<213> ORGANISM: Conus sulcatus
<220> FEATURE:
<221> NAME/KEY: CDS
<222> LOCATION: (1)..(189)

<400> SEQUENCE: 98

```
atg ttc acc gtg ttt ctg ttg gtt gtc ttg gca acc acc gtc gtt tcc   48
Met Phe Thr Val Phe Leu Leu Val Val Leu Ala Thr Thr Val Val Ser
 1               5                  10                  15 ttc aat tca gat cgt gca tta ggt ggc agg aat gct gca gcc aaa gcg   96
Phe Asn Ser Asp Arg Ala Leu Gly Gly Arg Asn Ala Ala Ala Lys Ala
                 20                  25                  30 tct gac aag atc gct tcg atc ctc ggg aga aga gca tgc tgt tct tat  144
Ser Asp Lys Ile Ala Ser Ile Leu Gly Arg Arg Ala Cys Cys Ser Tyr
     35                  40                  45 cct ccc tgt aac gtg aac tat cca gaa att tgt ggt gga cga ggc      189
Pro Pro Cys Asn Val Asn Tyr Pro Glu Ile Cys Gly Gly Arg Gly
     50                  55                  60 tgatgctcca ggaccctctg aaccacgacg t                                220
```

<210> SEQ ID NO 99
<211> LENGTH: 63
<212> TYPE: PRT
<213> ORGANISM: Conus sulcatus

<400> SEQUENCE: 99

```
Met Phe Thr Val Phe Leu Leu Val Val Leu Ala Thr Thr Val Val Ser
 1               5                  10                  15

Phe Asn Ser Asp Arg Ala Leu Gly Gly Arg Asn Ala Ala Ala Lys Ala
                 20                  25                  30

Ser Asp Lys Ile Ala Ser Ile Leu Gly Arg Arg Ala Cys Cys Ser Tyr
     35                  40                  45

Pro Pro Cys Asn Val Asn Tyr Pro Glu Ile Cys Gly Gly Arg Gly
     50                  55                  60
```

```
<210> SEQ ID NO 100
<211> LENGTH: 226
<212> TYPE: DNA
<213> ORGANISM: Conus purpurascens
<220> FEATURE:
<221> NAME/KEY: CDS
<222> LOCATION: (1)..(186)

<400> SEQUENCE: 100 atg ttc acc gtg ttt ctg ttg gtt gtc ttg gca acc act gtc ggt tcc      48
Met Phe Thr Val Phe Leu Leu Val Val Leu Ala Thr Thr Val Gly Ser
 1               5                  10                  15 ttc act tta gat cgt gca tct gat ggt agg gat gcc gca gcc aac gac      96
Phe Thr Leu Asp Arg Ala Ser Asp Gly Arg Asp Ala Ala Ala Asn Asp
             20                  25                  30 aaa gcg act gac ctg atc gct ctg acc gcc agg aga gat cca tgc tgt     144
Lys Ala Thr Asp Leu Ile Ala Leu Thr Ala Arg Arg Asp Pro Cys Cys
         35                  40                  45 tcc aat cct gtc tgt acc gtg cat aat cca cag att tgt ggt             186
Ser Asn Pro Val Cys Thr Val His Asn Pro Gln Ile Cys Gly
     50                  55                  60 tgaagacgct gatgcttcag gaccctctga accacgacgt                         226

<210> SEQ ID NO 101
<211> LENGTH: 62
<212> TYPE: PRT
<213> ORGANISM: Conus purpurascens

<400> SEQUENCE: 101

Met Phe Thr Val Phe Leu Leu Val Val Leu Ala Thr Thr Val Gly Ser
 1               5                  10                  15

Phe Thr Leu Asp Arg Ala Ser Asp Gly Arg Asp Ala Ala Ala Asn Asp
             20                  25                  30

Lys Ala Thr Asp Leu Ile Ala Leu Thr Ala Arg Arg Asp Pro Cys Cys
         35                  40                  45

Ser Asn Pro Val Cys Thr Val His Asn Pro Gln Ile Cys Gly
     50                  55                  60

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence:MI Analog

<400> SEQUENCE: 102

Gly Arg Cys Cys His Pro Ala Cys Gly Gln Asn Thr Ser Cys
 1               5                  10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence:MI Analog

<400> SEQUENCE: 103

Gly Arg Cys Cys His Pro Ala Cys Gly Glu Asn Thr Ser Cys
 1               5                  10

<210> SEQ ID NO 104
<211> LENGTH: 14
<212> TYPE: PRT
<213> ORGANISM: Artificial Sequence
```

-continued

```
<220> FEATURE:
<223> OTHER INFORMATION: Description of Artificial Sequence:MI Analog

<400> SEQUENCE: 104

Gly Arg Cys Cys His Pro Ala Cys Gly Gln Gln Thr Ser Cys
  1               5                  10

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence:MI Analog

<400> SEQUENCE: 105

Gly Arg Cys Cys Asn Pro Ala Cys Gly Gln Asn Thr Ser Cys
  1               5                  10

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence:MI Analog

<400> SEQUENCE: 106

Gly Arg Cys Cys His Pro Ala Cys Gly Asn Asn Thr Ser Cys
  1               5                  10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence:MI Analog

<400> SEQUENCE: 107

Arg Cys Cys His Pro Ala Cys Gly Gln Gln Thr Ser Cys
  1               5                  10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence:MI Analog

<400> SEQUENCE: 108

Gly Arg Cys Cys His Pro Ala Cys Gly Gln Asn Thr Asp Cys
  1               5                  10

<210> SEQ ID NO 109
<211> LENGTH: 14
<212> TYPE: PRT
<213> ORGANISM: Artificial Sequence
<220> FEATURE:
<221> NAME/KEY: PEPTIDE
<222> LOCATION: (10)
<223> OTHER INFORMATION: Xaa at residue 10 is homo-Ser
<223> OTHER INFORMATION: Description of Artificial Sequence:MI Analog

<400> SEQUENCE: 109

Gly Arg Cys Cys His Pro Ala Cys Gly Xaa Asn Thr Ser Cys
  1               5                  10

<210> SEQ ID NO 110
<211> LENGTH: 13
```

```
<212> TYPE: PRT
<213> ORGANISM: Artificial Sequence
<220> FEATURE:
<223> OTHER INFORMATION: Description of Artificial Sequence:MI Analog

<400> SEQUENCE: 110

Glu Cys Cys His Pro Ala Cys Gly Gln Asn Thr Ser Cys
 1               5                  10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence:MI Analog

<400> SEQUENCE: 111

Cys Cys His Pro Ala Cys Gly Gln Asn Thr Ser Cys
 1               5                  10

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence:MI Analog

<400> SEQUENCE: 112

Gly Arg Cys Cys His Pro Ala Cys Gly Gln Asn Phe Ser Cys
 1               5                  10

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence:MI Analog

<400> SEQUENCE: 113

Gly Arg Cys Cys His Pro Ala Cys Gly Gln Asn Thr Lys Cys
 1               5                  10

<210> SEQ ID NO 114
<211> LENGTH: 14
<212> TYPE: PRT
<213> ORGANISM: Artificial Sequence
<220> FEATURE:
<223> OTHER INFORMATION: Description of Artificial Sequence:MI Analog

<400> SEQUENCE: 114

Gly Glu Cys Cys His Pro Ala Cys Gly Gln Asn Thr Ser Cys
 1               5                  10

<210> SEQ ID NO 115
<211> LENGTH: 14
<212> TYPE: PRT
<213> ORGANISM: Artificial Sequence
<220> FEATURE:
<221> NAME/KEY: PEPTIDE
<222> LOCATION: (4)..(14)
<223> OTHER INFORMATION: Glu4 and Lys14 form a lactam bridge
<223> OTHER INFORMATION: Description of Artificial Sequence:MI Analog

<400> SEQUENCE: 115

Gly Arg Cys Glu His Pro Ala Cys Gly Gln Asn Thr Ser Lys
 1               5                  10
```

```
<210> SEQ ID NO 116
<211> LENGTH: 14
<212> TYPE: PRT
<213> ORGANISM: Artificial Sequence
<220> FEATURE:
<221> NAME/KEY: PEPTIDE
<222> LOCATION: (4)..(14)
<223> OTHER INFORMATION: Glu4 and Lys14 form a lactam bridge
<223> OTHER INFORMATION: Description of Artificial Sequence:MI Analog

<400> SEQUENCE: 116

Gly Arg Cys Glu His Pro Ala Cys Gly Asn Asn Thr Ser Lys
  1               5                  10

<210> SEQ ID NO 117
<211> LENGTH: 14
<212> TYPE: PRT
<213> ORGANISM: Artificial Sequence
<220> FEATURE:
<221> NAME/KEY: PEPTIDE
<222> LOCATION: (4)..(14)
<223> OTHER INFORMATION: Asp4 and Lus14 form a lactam bridge
<223> OTHER INFORMATION: Description of Artificial Sequence:MI Analog

<400> SEQUENCE: 117

Gly Arg Cys Asp His Pro Ala Cys Gly Gln Asn Thr Ser Lys
  1               5                  10

<210> SEQ ID NO 118
<211> LENGTH: 14
<212> TYPE: PRT
<213> ORGANISM: Artificial Sequence
<220> FEATURE:
<221> NAME/KEY: PEPTIDE
<222> LOCATION: (4)..(14)
<223> OTHER INFORMATION: Asp4 and Lys14 form a lactam bridge
<223> OTHER INFORMATION: Description of Artificial Sequence:MI Analog

<400> SEQUENCE: 118

Gly Arg Cys Asp His Pro Ala Cys Gly Asn Asn Thr Ser Lys
  1               5                  10

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence:GI Analog

<400> SEQUENCE: 119

Glu Cys Cys Asn Pro Ala Cys Gly Gln His Thr Ser Cys
  1               5                  10

<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence:GI Analog

<400> SEQUENCE: 120

Glu Cys Cys Asn Pro Ala Cys Gly Asn His Thr Ser Cys
  1               5                  10

<210> SEQ ID NO 121
<211> LENGTH: 13
<212> TYPE: PRT
<213> ORGANISM: Artificial Sequence
<220> FEATURE:
```

```
<221> NAME/KEY: PEPTIDE
<222> LOCATION: (3)..(13)
<223> OTHER INFORMATION: Glu3 and Lys13 form a lactam bridge
<223> OTHER INFORMATION: Description of Artificial Sequence:GI Analog

<400> SEQUENCE: 121

Glu Cys Glu Asn Pro Ala Cys Gly Arg His Thr Ser Lys
 1               5                  10

<210> SEQ ID NO 122
<211> LENGTH: 13
<212> TYPE: PRT
<213> ORGANISM: Artificial Sequence
<220> FEATURE:
<221> NAME/KEY: PEPTIDE
<222> LOCATION: (3)..(13)
<223> OTHER INFORMATION: Glu3 and Lys13 form a lactam bridge
<223> OTHER INFORMATION: Description of Artificial Sequence:GI Analog

<400> SEQUENCE: 122

Glu Cys Glu Asn Pro Ala Cys Gly Gln His Thr Ser Lys
 1               5                  10

<210> SEQ ID NO 123
<211> LENGTH: 13
<212> TYPE: PRT
<213> ORGANISM: Artificial Sequence
<220> FEATURE:
<221> NAME/KEY: PEPTIDE
<222> LOCATION: (3)..(13)
<223> OTHER INFORMATION: Glu3 and Lys13 form a lactam bridge
<223> OTHER INFORMATION: Description of Artificial Sequence:GI Analog

<400> SEQUENCE: 123

Glu Cys Glu Asn Pro Ala Cys Gly Asn His Thr Ser Lys
 1               5                  10

<210> SEQ ID NO 124
<211> LENGTH: 13
<212> TYPE: PRT
<213> ORGANISM: Artificial Sequence
<220> FEATURE:
<221> NAME/KEY: PEPTIDE
<222> LOCATION: (3)..(13)
<223> OTHER INFORMATION: Asp3 and Lys13 form a lactam bridge
<223> OTHER INFORMATION: Description of Artificial Sequence:GI Analog

<400> SEQUENCE: 124

Glu Cys Asp Asn Pro Ala Cys Gly Gln His Thr Ser Lys
 1               5                  10

<210> SEQ ID NO 125
<211> LENGTH: 13
<212> TYPE: PRT
<213> ORGANISM: Artificial Sequence
<220> FEATURE:
<221> NAME/KEY: PEPTIDE
<222> LOCATION: (3)..(13)
<223> OTHER INFORMATION: Asp3 and Lys13 form a lactam bridge
<223> OTHER INFORMATION: Description of Artificial Sequence:GI Analog

<400> SEQUENCE: 125

Glu Cys Asp Asn Pro Ala Cys Gly Asn His Thr Ser Lys
 1               5                  10
```